United States Patent
Wang et al.

(10) Patent No.: US 12,384,786 B2
(45) Date of Patent: Aug. 12, 2025

(54) CYCLIC MOLECULES AS BRUTON'S TYROSINE KINASE INHIBITOR

(71) Applicants: MINGHUI PHARMACEUTICAL (SHANGHAI) LIMITED, China (CN); MINGHUI PHARMACEUTICAL (HANGZHOU) LIMITED, Zhejiang (CN)

(72) Inventors: Zhaoyin Wang, Shanghai (CN); Bing Yao, Shanghai (CN); Yuanshan Yao, Shanghai (CN); Ao Li, Shanghai (CN); Guoqing Cao, Shanghai (CN)

( * ) Notice: Subject to any disclaimer, the term of this patent is extended or adjusted under 35 U.S.C. 154(b) by 805 days.

(21) Appl. No.: 17/423,815

(22) PCT Filed: Jan. 16, 2020

(86) PCT No.: PCT/CN2020/072551
§ 371 (c)(1),
(2) Date: Jul. 16, 2021

(87) PCT Pub. No.: WO2020/147798
PCT Pub. Date: Jul. 23, 2020

(65) Prior Publication Data
US 2022/0081445 A1    Mar. 17, 2022

(30) Foreign Application Priority Data
Jan. 18, 2019    (CN) .......................... 201910049183.9

(51) Int. Cl.
*C07D 487/04*    (2006.01)
*A61P 35/00*    (2006.01)

(52) U.S. Cl.
CPC ............ *C07D 487/04* (2013.01); *A61P 35/00* (2018.01)

(58) Field of Classification Search
CPC ........ C07D 487/04; A61P 35/00; A61P 19/02; A61K 31/519
See application file for complete search history.

(56) References Cited

U.S. PATENT DOCUMENTS

| | | |
|---|---|---|
| 6,921,763 B2 | 7/2005 | Hirst et al. |
| 2011/0184001 A1 | 7/2011 | Honigberg et al. |
| 2014/0080844 A1 | 3/2014 | Chen et al. |
| 2018/0298008 A1* | 10/2018 | Guisot .................. A61K 31/538 |

FOREIGN PATENT DOCUMENTS

| | | | |
|---|---|---|---|
| CN | 105732638 A | 7/2016 | |
| CN | 107827892 A | 3/2018 | |
| WO | WO-0119829 A2 * | 3/2001 | ................. A61P 1/04 |
| WO | WO-2013010380 A1 * | 1/2013 | ......... A61K 31/4985 |

OTHER PUBLICATIONS

Zhang, S. Q.; et al. "Mechanisms of ibrutinib resistance in chronic lymphocytic leukaemia and non-Hodgkin lymphoma" 2015, British Journal of Haematology, vol. 170, pp. 445-456. (Year: 2015).*
Ma, J.; et al. "Characterization of ibrutinib-sensitive and -resistant mantle lymphoma cells" 2014, British Journal of Haematology, vol. 166, pp. 849-861. (Year: 2014).*
Bam, R.; et al. "Role of Bruton's tyrosine kinase (BTK) in growth and metastasis of INA6 myeloma cells" 2014, Blood Cancer Journal, vol. 4, e234. (Year: 2014).*
Hashimoto, S.; et al. "Identification of Bruton's Tyrosine Kinase (Btk) Gene Mutations and Characterization of the Derived Proteins in 35 X-Linked Agammaglobulinemia Families: A Nationwide Study of Btk Deficiency in Japan" 1996, Blood, vol. 88, pp. 561-573. (Year: 1996).*
Pan, Z.; et al. "Discovery of Selective Irreversible Inhibitors for Bruton's Tyrosine Kinase" 2007, ChemMedChem, vol. 2, pp. 58-61. (Year: 2007).*
Robak, T.; Robak, E. "Tyrosine kinase inhibitors as potential drugs for B-cell lymphoid malignancies and autoimmune disorders" 2012, Expert Opinion on Investigational Drugs, vol. 21, pp. 921-947. (Year: 2012).*
International Search Report mailed Apr. 10, 2020 corresponding to PCT/CN/2020/072551 filed Jan. 16, 2020; 7 pages.

* cited by examiner

*Primary Examiner* — Eric Olson
*Assistant Examiner* — Benjamin M Brandsen
(74) *Attorney, Agent, or Firm* — Mintz Levin Cohn Ferris Glovsky and Popeo, P.C.

(57) ABSTRACT

The present invention relates to a novel molecule with protein tyrosine kinase inhibitory activity, and the synthesis and usage thereof. Specifically, the present invention relates to compound by formula A, pharmaceutically acceptable salts, hydrates or solvates thereof, and the synthesis and usage thereof.

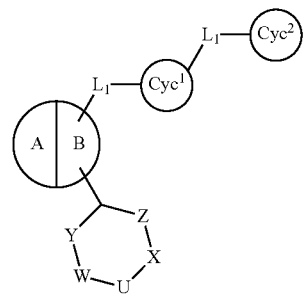

formula A

11 Claims, 1 Drawing Sheet

CYCLIC MOLECULES AS BRUTON'S TYROSINE KINASE INHIBITOR

FIELD OF THE INVENTION

The present invention relates to the field of small molecular medicine. Specifically, provided herein is a novel molecule of protein tyrosine kinase inhibitory activity, and the synthesis and application thereof.

BACKGROUND OF THE INVENTION

Protein kinases are the largest family of human enzymes, which covers more than 500 proteins. Bruton tyrosine kinase (Btk) is a member of the tyrosine kinases Tec family and a regulator of early B cell development and mature B cell activation, signal transduction and survival. Btk has become a new molecular target for the treatment of B-cell lymphoma, leukemia and autoimmune diseases. Therefore, there is an urgent need to provide more small molecule compounds of Btk inhibitory activity in the field.

BRIEF SUMMARY OF THE INVENTION

The purpose of the present invention is to provide a small molecular compound of Btk inhibitory activity.

In the first aspect of the present invention, a compound according to the Formula A:

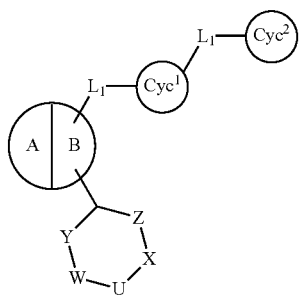

A or a pharmaceutically acceptable salt thereof is provided, wherein,

Ring A and ring B are fused to each other, and are independently selected from substituted or unsubstituted 5-15 membered heterocyclic ring or heteroaromatic ring;

$Cyc^1$ is selected from the group consisting of substituted or unsubstituted $C_1$-$C_6$ alkyl, substituted or unsubstituted $C_3$-$C_{10}$ cycloalkyl, substituted or unsubstituted $C_2$-$C_6$ alkenyl, substituted or unsubstituted $C_3$-$C_{10}$ cycloalkenyl, substituted or unsubstituted 5-15 membered heterocyclic group, substituted or unsubstituted 5-15 membered heteroaryl, substituted or unsubstituted $C_6$-$C_{10}$ aryl;

$Cyc^1$ is selected from the group consisting of substituted or unsubstituted $C_1$-$C_6$ alkyl, substituted or unsubstituted $C_3$-$C_{10}$ cycloalkyl, substituted or unsubstituted $C_2$-$C_6$ alkenyl, substituted or unsubstituted $C_3$-$C_{10}$ cycloalkenyl, substituted or unsubstituted 5-15 membered heterocyclic group, substituted or unsubstituted 5-15 membered heteroaryl, substituted or unsubstituted $C_6$-$C_{10}$ aryl;

$L_1$ and $L_2$ are selected independently from the group consisting of bond, N, O, S, —S(=O), —S(=O)$_2$, C(=O), or —C(O)NH—;

Z is $(CR^2R^3)_n$, n is 0, 1, 2, 3, 4, 5 or 6;

Y is $(CR^4R^5)_m$, m is 0, 1, 2, 3, 4, 5 or 6;

U is $(CR^6R^7)_r$, r is 0, 1, 2 or 3;

wherein, n, m, r are not 0 simultaneously;

$R^2$, $R^3$, $R^4$, $R^5$, $R^6$ and $R^7$ are selected independently from the group consisting of H, $NH_2$, OH, halogen, substituted or unsubstituted $C_1$-$C_6$ alkyl; or any two of $R^2$, $R^3$, $R^4$, $R^5$, $R^6$, $R^7$ and $R^8$ together with the adjacent carbon atom and the ring member atom between them form $C_3$-$C_8$ carbocyclic ring, or 4-8-membered heterocyclic ring, wherein, the heteroatom of the heterocyclic ring is selected from the group consisting of S, O, or $NR^f$; $R^f$ is H, $C_1$-$C_{10}$ alkyl, $C_3$-$C_{10}$ cycloalkyl, $C_6$-$C_{20}$ aryl, or $C_3$-$C_{14}$ heteroaryl; and at least one of $R^2$, $R^3$, $R^4$, $R^5$, $R^6$, $R^7$, $R^8$ and $R^9$ is OH or —[C($R^{10}$)($R^{11}$)]$_k$—OH;

W is selected independently from the group consisting of N, O, S, or bond;

X is —C($R^8R^9$)—;

$R^8$ is selected independently from the group consisting of H, substituted or unsubstituted $C_1$-$C_6$ alkyl, substituted or unsubstituted $C_3$-$C_{10}$ cycloalkyl, substituted or unsubstituted $C_6$-$C_{20}$ aryl, substituted or unsubstituted $C_3$-$C_{14}$ heteroaryl, $CO_2H$, $C(O)NR^f_2$;

$R^9$ is selected independently from the group consisting of H, OH or —[C($R^{10}$)($R^{11}$)]$_k$—OH;

or $R^8$ and $R^9$ jointly form =O;

and when $R^8$ is H, $R^9$ is OH or —[C($R^{10}$)($R^{11}$)]$_k$—OH;

$R^{10}$ and $R^{11}$ are selected independently from the group consisting of H, substituted or unsubstituted $C_1$-$C_6$ alkyl, substituted or unsubstituted $C_3$-$C_{10}$ cycloalkyl, substituted or unsubstituted $C_6$-$C_{10}$ aryl, substituted or unsubstituted $C_3$-$C_{14}$ heteroaryl; or $R^{10}$ and $R^{11}$ together with the connected adjacent carbon atom to form $C_3$-$C_8$ carbocyclic ring, or 4-8-membered heterocyclic ring, wherein, the heteroatom is selected from the group consisting of sulfur, oxygen or NR;

k is 1, 2, 3, 4, 5 or 6;

unless otherwise specified, the abovementioned heteroaromatic ring, heteroaryl, heterocyclic ring and heterocyclic group each independently contains 1-4 heteroatoms selected from the group consisting of N, O and S.

unless otherwise specified, "substituted" refers to being substituted by one or more (for example, 2, 3, 4, etc.) substituents selected from the group consisting of halogen, $C_1$-$C_6$ alkyl, halogenated $C_1$-$C_6$ alkyl, $C_1$-$C_6$ alkoxy, halogenated $C_1$-$C_6$ alkoxy, $C_3$-$C_8$ cycloalkyl, halogenated $C_3$-$C_8$ cycloalkyl, oxo, —CN, hydroxy, hydroxy-$C_1$-$C_6$ alkyl, —$NH_2$, carboxy, $C_6$-$C_{10}$ aryl, halogenated $C_6$-$C_{10}$ aryl, 5-10 membered heteroaryl with 1-3 heteroatoms selected from N, S, or O unsubstituted or substituted by substituent selected from the group consisting of: halogen, phenyl.

In a preferred embodiment, $L_1$-$Cyc^1$-$L_2$-$Cyc^2$ is:

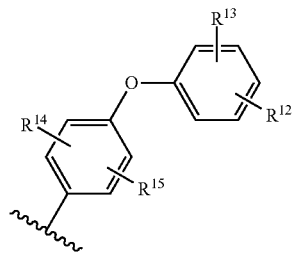

wherein, $R^{12}$, $R^{13}$, $R^{14}$ and $R^{15}$ are selected independently from the group consisting of H, halogen, substituted or unsubstituted $C_1$-$C_6$ alkyl, substituted or unsubstituted $C_1$-$C_6$ alkoxyl, substituted or unsubstituted $C_3$-$C_{10}$ cycloalkyl, substituted or unsubstituted $C_3$-$C_{10}$ heterocyclic alkyl, the heteroatoms are selected from N, O, S.

In a preferred embodiment, $L_1$-$Cyc^1$-$L_2$-$Cyc^2$ is

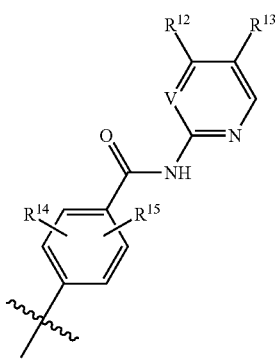

V is N or —$CR^{16}$—; wherein $R^{16}$ is selected from the group consisting of H, unsubstituted or halogenated $C_1$-$C_6$ alkyl, substituted or unsubstituted $C_3$-$C_{10}$ cycloalkyl.

In a preferred embodiment,

has a structure as followed:

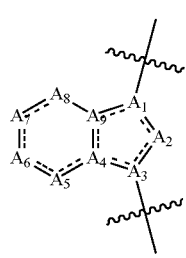

Wherein, the dotted line is bond or none; each $A_1$, $A_2$, $A_3$, $A_4$, $A_5$, $A_6$, $A_7$, $A_8$ and $A_9$ is independently selected from the group consisting of O, S, N, NH, CH or $CH_2$;

The wavy line represents linking joint;

And the substitution sites of the abovementioned groups comprise substituents, wherein, the substituents are defined as above.

In a preferred embodiment,

is selected from following structures:

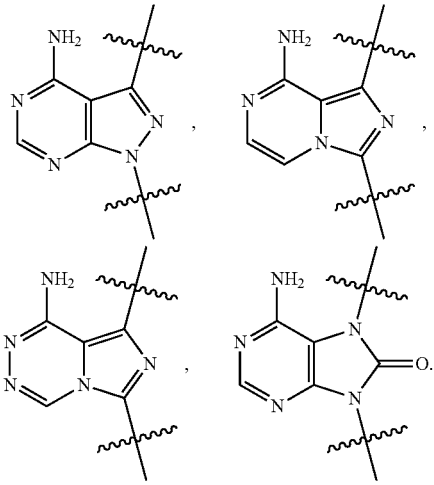

In a preferred embodiment, the compound has the following formula B structure:

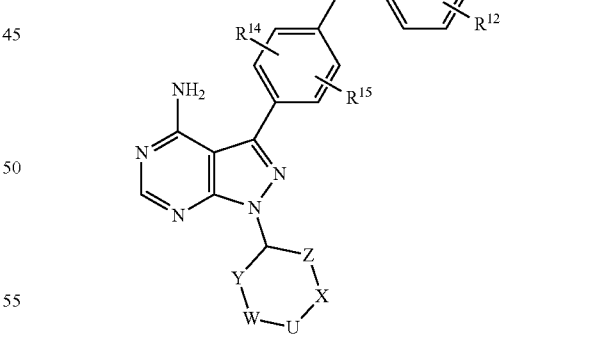

Wherein, $R^{12}$, $R^{13}$, $R^{14}$ and $R^{15}$ are independently selected from the group consisting of H, halogen, substituted or unsubstituted $C_1$-$C_6$ alkyl, substituted or unsubstituted $C_1$-$C_6$ alkoxy, substituted or unsubstituted $C_3$-$C_{10}$ cycloalkyl, substituted or unsubstituted 5-15 membered heterocyclic group.

In a preferred embodiment, the compound has the following formula C structure:

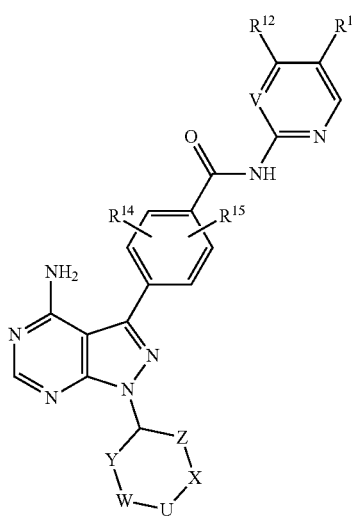

Wherein, V is N or —$CR^{16}$—;

$R^{12}$, $R^{13}$, $R^{14}$ and $R^{15}$ are independently selected from the group consisting of H, halogen, substituted or unsubstituted $C_1$-$C_6$ alkyl, substituted or unsubstituted $C_1$-$C_6$ alkoxy, substituted or unsubstituted $C_3$-$C_{10}$ cycloalkyl, substituted or unsubstituted 5-15 membered heterocyclic group;

$R^{16}$ is selected from the group consisting of H, unsubstituted or halogenated $C_1$-$C_6$ alkyl, substituted or unsubstituted $C_3$-$C_{10}$ cycloalkyl.

In a preferred embodiment,

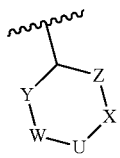

is selected from the group shown below:

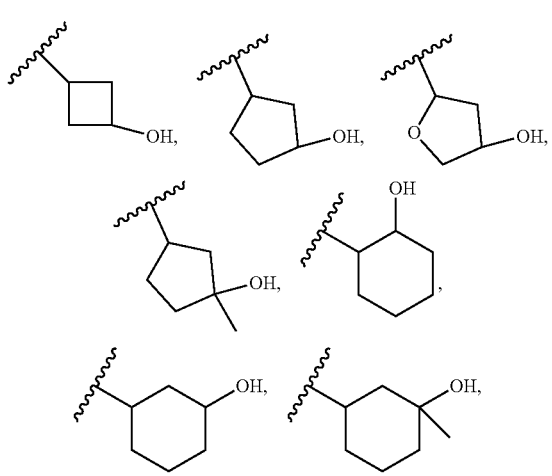

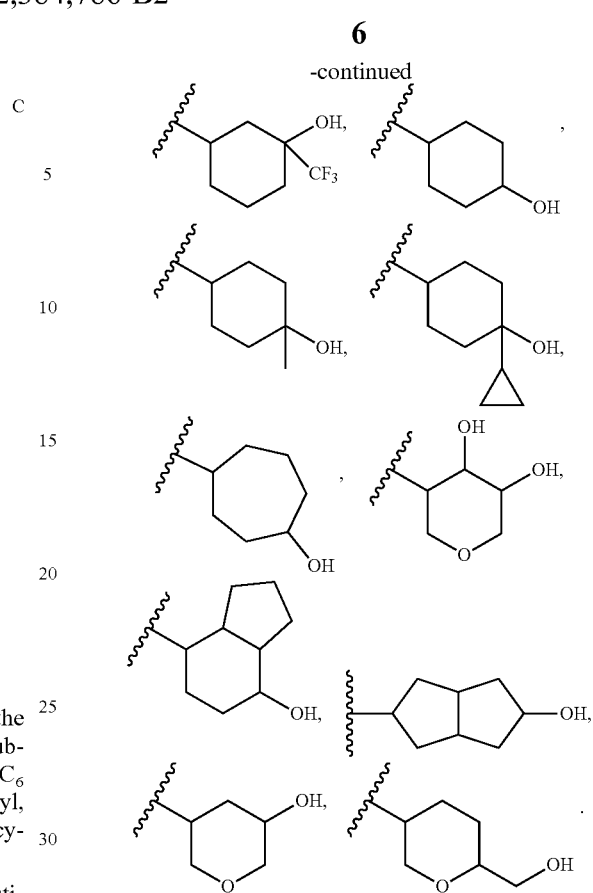

In a preferred embodiment,

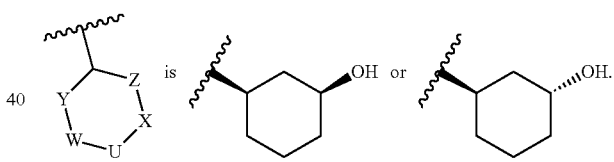

In a preferred embodiment,

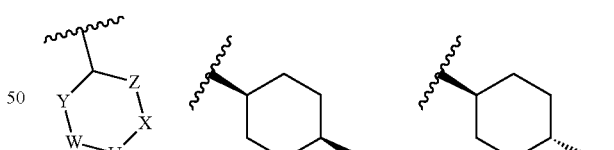

In a preferred embodiment,

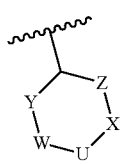

is substituted cyclohexyl or epoxypentanyl.

In a preferred embodiment, the compound has the following formula D, E or F structure:

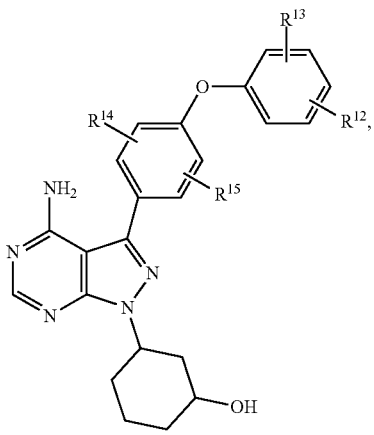

D

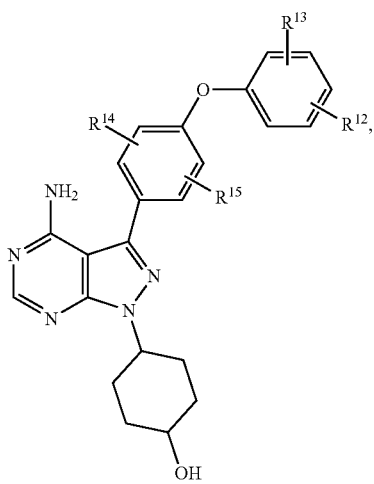

E

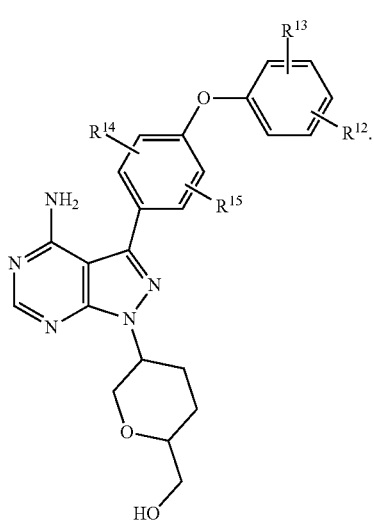

F

In a preferred embodiment, the compound is selected from the following group:

1) (1R,3R)-3-(4-amino-3-(4-phenoxyphenyl)-1H-pyrazolo[3,4-d]pyrimidin-1-yl) cyclohex-1-ol (Example 1)
2) (1S,3R)-3-(4-amino-3-(4-phenoxyphenyl)-1H-pyrazolo[3,4-d]pyrimidin-1-yl) cyclohex-1-ol (Example 2)
3) (1S,3R)-3-(4-amino-3-(4-phenoxyphenyl)-1H-pyrazolo[3,4-d]pyrimidin-1-yl)-1-methylcyclohexane-1-ol/(1R,3R)-3-(4-amino-3-(4-phenoxyphenyl)-1H-pyrazolo[3,4-d]pyrimidin-1-yl)-1-methylcyclohexane-1-ol (Example 3)
4) 3-(4-amino-3-(4-phenoxyphenyl)-1H-pyrazolo[3,4-d]pyrimidin-1-yl)-1-(trifluoromethyl)cyclohex-1-ol (Example 4)
5) 3-(4-amino-3-(4-phenoxyphenyl)-1H-pyrazolo[3,4-d]pyrimidin-1-yl)-1-methylcyclopentanol (Example 5)
6) 3-(4-amino-3-(4-phenoxyphenyl)-1H-pyrazolo[3,4-d]pyrimidin-1-yl)-1-methylcyclopentanol (Example 6)
7) 3-(4-amino-3-(4-phenoxyphenyl)-1H-pyrazolo[3,4-d]pyrimidin-1-yl)-1-(trifluoromethyl)cyclopentanol (Example 7)
8) (1S,4S)-4-(4-amino-3-(4-phenoxyphenyl)-1H-pyrazolo[3,4-d]pyrimidin-1-yl)cyclohexane-1-ol/(1R,4R)-4-(4-amino-3-(4-phenoxyphenyl)-1H-pyrazolo[3,4-d]pyrimidin-1-yl) cyclohexane-1-ol (Example 8)
9) (1S,4S)-4-(4-amino-3-(4-phenoxyphenyl)-1H-pyrazolo[3,4-d]pyrimidin-1-yl]-1-methylcyclohexane-1-ol/(1R,4R)-4(4-amino-3-(4-phenoxyphenyl)-1H-pyrazolo[3,4-d]pyrimidin-1-yl]-1-methylcyclohexane-1-ol (Example 9)
10) 4-(4-amino-3-(4-phenoxyphenyl)-1H-pyrazolo[3,4-d]pyrimidin-1-yl]-1-cyclopropylcyclohexane-1-ol (Example 10)
11) (1S,4S)-4-(4-amino-3-(4-(4-fluorophenoxy)phenyl)-1H-pyrazolo[3,4-d]pyrimidin-1-yl)cyclohex-1-ol/(1R,4R)-4-(4-amino-3-(4-(4-fluorophenoxy)phenyl)-1H-pyrazolo[3,4-d]pyrimidin-1-yl)cyclohex-1-ol (Example 11)
12) (1S,4S)-4-(4-amino-3-(4-(4-fluorophenoxy)phenyl)-1H-pyrazolo[3,4-d]pyrimidin-1-yl)-1-methylcyclohex-1-ol and (1R,4R)-4-(4-amino-3-(4-(4-fluorophenoxy)phenyl)-1H-pyrazolo[3,4-d]pyrimidin-1-yl)-1-methylcyclohex-1-ol (Example 12)
13) Cis-3-(4-amino-3-(4-(4-fluorophenoxy)phenyl)-1H-pyrazolo[3,4-d]pyrimidin-1-yl)cyclopentane-1-ol and trans-3-(4-amino-3-(4-(4-fluorophenoxy)phenyl)-1H-pyrazolo[3,4-d]pyrimidin-1-yl) cyclopentane-1-ol (Example 13)
14) (±)Cis-3-(4-amino-3-(4-(4-fluorophenoxy)phenyl)-1H-pyrazolo[3,4-d]pyrimidin-1-yl)-1-methylcyclopentan-1-ol/(±)Trans-3-(4-amino-3-(4-(4-fluorophenoxy)phenyl)-1H-pyrazolo[3,4-d]pyrimidin-1-yl)-1-methylcyclopentan-1-ol (Example 14)
15) (1R,3R)-3-(4-amino-3-(4-(3-fluorophenoxy)phenyl)-1H-pyrazolo[3,4-d]pyrimidin-1-yl) cyclohex-1-ol (Example 15)
16) (1R,3R)-3-(4-amino-3-(2-fluoro-4-phenoxyphenyl)-1H-pyrazolo[3,4-d]pyrimidin-1-yl)cyclohex-1-ol (Example 16)
17) (1R,3R)-3-(4-amino-3-(4-(3-fluorophenoxy)phenyl)-1H-pyrazolo[3,4-d]pyrimidin-1-yl)cyclohex-1-ol (Example 17)
18) (1R,3R)-3-(4-amino-3-(4-(2,6-difluorophenoxy)phenyl)-1H-pyrazolo[3,4-d]pyrimidin-1-yl)cyclohex-1-ol (example 18)
19) (1R,3R)-3-(4-amino-3-(4-(2-fluoro-3-methoxyphenoxy)phenyl)-1H-pyrazolo[3,4-d]pyrimidin-1-yl)cyclohex-1-ol (Example 19)
20) (1S,4S)-4-(4-amino-3-(4-(2-fluoro-3-methoxyphenoxy)phenyl)-1H-pyrazolo[3,4-d]pyrimidin-1-yl)cyclohex-1-ol (Example 20)
21) (1R,4R)-4-(4-amino-3-(4-(2-fluoro-3-methoxyphenoxy)phenyl)-1H-pyrazolo[3,4-d]pyrimidin-1-yl)cyclohex-1-ol (Example 21)

22) cis-3-(4-amino-3-(4-(2-fluoro-3-methoxyphenoxy)phenyl)-1H-pyrazolo[3,4-d]pyrimidin-1-yl) cyclopentane-1-ol (Example 22)
23) trans-3-(4-amino-3-(4-(2-fluoro-3-methoxyphenoxy)phenyl)-1H-pyrazolo[3,4-d]pyrimidin-1-yl)cyclopentane-1-ol (Example 23)
24) 5-(4-amino-3-(4-phenoxyphenyl)-1H-pyrazolo[3,4-d]pyrimidin-1-yl) tetrahydro-2H-pyran-3,4-diol (Example 24)
25) 3-(4-amino-3-(4-(3-fluorophenoxy)phenyl)-1H-pyrazolo[3,4-d]pyrimidin-1-yl)cyclopentane-1-ol (Example 25)
26) cis-3-(4-amino-3-(4-(2-fluoro-3-methoxyphenoxy)phenyl)-1H-pyrazolo[3,4-d]pyrimidin-1-yl)cyclohex-1-ol (Example 26)
27) 3-(4-amino-3-(4-(2-fluoro-3-methoxyphenoxy)phenyl)-1H-pyrazolo[3,4-d]pyrimidin-1-yl)cyclohexane-1,2-diol (Example 27)
28) 4-(4-amino-3-(4-(2-fluoro-3-methoxyphenoxy)phenyl)-1H-pyrazolo[3,4-d]pyrimidin-1-yl) cyclohexane-1,2-diol (Example 28)
30) (5-(4-amino-3-(4-(2-fluoro-3-methoxyphenoxy)phenyl)-1H-pyrazolo[3,4-d]pyrimidin-1-yl)tetrahydro-2H-pyran-2-yl)methanol (Example 30)
31) (1R,3R)-3-(4-amino-3-(4-(2-fluoro-3-(methoxy-d3)phenoxy)phenyl)-1H-pyrazolo[3,4-d]pyrimidin-1-yl)cyclohexanol (Example 31)
32) (1S,3S)-3-(4-amino-3-(4-(2-fluoro-3-methoxyphenoxy)phenyl)-1H-pyrazolo[3,4-d]pyrimidin-1-yl)cyclohexanol (Example 32)
33) 3-(4-(4-amino-1-((1R,3R)-3-hydroxycyclohexyl)-1H-pyrazolo[3,4-d]pyrimidin-3-yl)phenoxy)-2-fluorophenol (Example 33).

In the second aspect of the present invention, a pharmaceutical composition is provided, which comprising (1) the compound according to the first aspect of the present invention, or stereoisomers or tautomers thereof, or pharmaceutically acceptable salts, hydrates or solvates thereof; (2) a pharmaceutically acceptable carrier.

In the third aspect of the present invention, the use of the compound according to the first aspect of the present invention, or stereoisomers or tautomers thereof, or pharmaceutically acceptable salts, hydrates or solvates thereof, or the pharmaceutical composition according to the fourth aspect of the present invention is provided, wherein in the preparation of drugs for preventing and/or treating diseases which relates to BTK abnormal activity and BTK mutants (e.g. C481S) abnormal activity.

In a preferred embodiment, the diseases or disorders are selected from the group consisting of bladder cancer, brain tumor, breast cancer, uterine cancer, colorectal cancer, esophageal cancer, liver cancer, follicular lymphoma, melanoma, malignant hematologic disease, myeloma, ovarian cancer, non-small cell lung cancer, prostate cancer, small cell lung cancer, and B-cell derived lymphoid malignancy, B cell proliferative disorder: diffuse B cell lymphoma, follicular lymphoma, chronic lymphocytic lymphoma, chronic lymphocytic leukemia, B-cell prolymphocyte leukemia, lymphoplasmacytic lymphoma/Waldenstrom's macroglobulinemia, splenic marginal zone lymphoma, plasmacytic myeloma, plasmacytoma, extranodal marginal zone B-cell lymphoma, intranodal marginal zone B-cell lymphoma, mantle cell lymphoma Mediastinal (thymic) large B-cell lymphoma, intravascular large B-cell lymphoma, primary exudative lymphoma, Burkitt's lymphoma/leukemia or lymphomatoid granulomatosis.

In a preferred embodiment, the diseases or disorders are selected from the group consisting of autoimmune disease and inflammatory disease which comprises rheumatoid arthritis, psoriatic arthritis, osteoarthritis and juvenile arthritis; the hepatitis comprises autoimmune hepatitis; the cystitis comprises interstitial cystitis; the allergic reaction comprises allergy, type I hypersensitivity and allergic rhinitis; the bronchitis comprises bronchiolitis; the enteritis comprises colitis and proctitis; the dermatitis comprises atopic dermatitis, scleroderma and psoriasis; the myelitis includes acute disseminated encephalomyelitis; the gastritis comprises gastroenteritis; the nephritis comprises pyelonephritis; the rhinitis comprises sinusitis.

It should be understood that, in the present invention, each of the technical features specifically described above and below (such as those in the Examples) can be combined with each other, thereby constituting new or preferred technical solutions which are not necessarily specified one by one herein.

EMBODIMENTS FOR CARRYING OUT THE INVENTION

Figure 1:
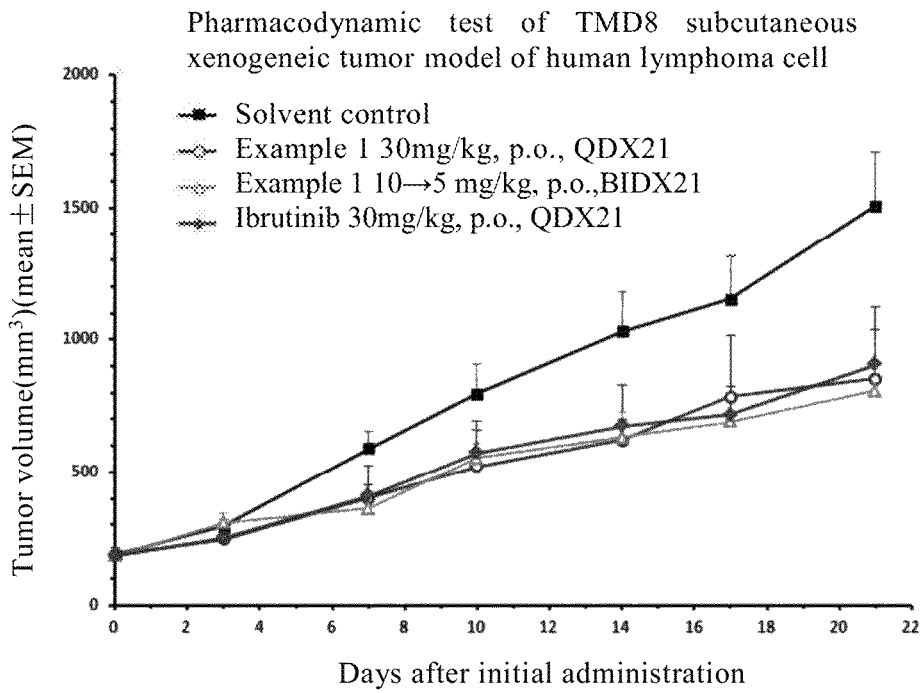
FIG. 1: the volumes of subcutaneous xenograft TMD8 tumor (mean SD) of the solvent control group and each treatment group during administration.

The inventor discovered a compound according to formula A after long-term and in-depth research. The compound has an unexpected inhibitory activity on BTK, especially BTK C4818S mutant and can be used to treat BTK mediated cancer, allergic diseases, autoimmune diseases, inflammatory diseases, etc, and in the treatment of B-cell lymphoma and leukemia, especially, cancer patients with drug resistance to existing drugs. The inventors have completed the present invention on this basis.

Terms

The abbreviations used herein have common meanings in the field of chemistry and biology.

Unless otherwise stated, the term "alkyl" itself or as part of another substituent refers to a straight chain (i.e. unbranched) or branched chain, or cyclic hydrocarbon group, or a combination thereof, which may be saturated, single or polyunsaturated, may include bivalent or polyvalent groups, with a specified amount of carbon atoms (i.e. $C_1$-$C_{10}$ means one to ten carbon atoms). Examples of saturated hydrocarbon groups include, but are not limited to, groups such as methyl, ethyl, n-propyl, isopropyl, n-butyl, t-butyl, isobutyl, s-butyl, cyclohexyl, cyclohexylmethyl, cyclopropylmethyl, etc., such as n-pentayl, n-hexyl, n-heptyl, n-octyl. Unsaturated alkyl is an alkyl group with one or more double or triple bonds. Examples of unsaturated alkyls include, but not limited to, vinyl, 2-propenyl, crotyl, 2-isopentenyl, 2-(butadiene), 2,4-pentylenyl, 3-(1,4-pentylenyl), acetylene, 1-propinyl, 3-propinyl, 3-butynyl, and advanced homologues and isomers. The hydrocarbon group defined as alkyl is called homoalkyl. The alkyl is optionally replaced by one or more halogen atoms.

The term "fluoroalkyl" means the alkyl group as defined above, wherein, one or more hydrogen atoms are replaced by the fluorine atom.

The term "alkylene" itself or as part of another substituent group refers to a divalent group derived from an alkyl group, for example, but not limited to, —CH$_2$CH$_2$CH$_2$CH$_2$—, —CH$_2$CH═CHCH$_2$—, —CH$_2$C≡CCH$_2$—, —CH$_2$CH$_2$CH(CH$_2$CH$_2$CH$_3$)CH$_2$—. Alkyl (or alkylidene) usually has 1 to 24 carbon atoms, and the group with 10 or less carbon atoms is preferred in the present invention. "Lower alkyl" or "lower alkylene" refers to an alkyl or alkylene with a shorter chain, usually having eight or fewer carbon atoms. The alkylene is selectively replaced by one or more halogen atoms.

The term "alkynyl" refers to a carbon chain containing at least one carbon carbon triple bond, which may be linear or branched, or a combination thereof. Examples of alkynyl include ethynyl, propinyl, 3-methyl-1-pentynyl, 2-heptynyl, etc. The alkynyl group is optionally substituted by one or more halogen atoms.

The term "cycloalkyl" refers to a monocyclic or bicyclic saturated carbon ring, each with 3 to 10 carbon atoms. "Fused analogues" of cycloalkyl group refer to the single ring fusing with aryl or heteroaryl group, in which the connecting site is in non-aromatic part. Examples of cycloalkyl and their analogues include cyclopropyl, cyclobutyl, cyclopentyl, cyclohexyl, tetrahydronaphthyl, decahydronaphthyl, dihydroindenyl, etc. The cycloalkyl is optionally replaced by one or more halogen atoms.

The term "alkoxy" refers to a linear or branched alkoxy group having a number of carbon atoms. C$_{1-6}$ alkoxy, for example, including methoxy, ethoxy, propoxy, isopropoxy, etc.

Unless otherwise specified, the term "heteroalkyl" itself or in combination with another term refers to a stable linear or branched chain, or cycloalkyl group, or a combination thereof, consisting of at least one carbon atom and at least one heteroatom selected from O, N, P, Si, S, wherein the nitrogen atom, phosphorus atom or sulfur atom may be selectively oxidized and the nitrogen atom may be selectively quaternized. Heteroatoms O, N, P, S and Si can be placed at any position in the heteroalkyl group or at the position where the alkyl group is connected with the rest of the molecule. Examples include, but not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CHO—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$ and —CN. At most two or three heteroatoms can be continuous. For example, —CH$_2$—CH$_2$—S—CH$_2$—CH$_2$— and —CH$_2$—S—CH$_2$—CH$_2$—NH—CH$_2$—. Similarly, the term "heteroalkylene" itself or in combination with other terms refers to divalent groups derived from heteroalkyl groups, such as, but not limited to, —CH$_2$—CH$_2$—S—CH$_2$—CH$_2$— and —CH$_2$—S—CH$_2$—CH$_2$—NH—CH$_2$—. For heteroalkylenes, heteroatoms may be at either or both ends of the chain (e.g., alkyleneoxy, alkylenedioxy, alkyleneamino, alkylenediamino, etc.). In addition, for the alkylene and heteroalkylene groups, the writing direction of the molecular formula of the connecting group does not indicate the orientation of the connecting group. For example, the formula —C(O)OR'— means —C(O)OR'— and —R'OC(O)—. As mentioned above, heteroalkyl groups used herein include those groups that are connected to the rest of the molecule by heteroatoms, such as —C(O)R', —C(O)NR', —NR'R', —OR', —SR' and/or —SO$_2$R'.

Where reference is made to "heteroalkyl" followed by specific heteroalkyl such as —NR'R", it should be understood that the terms heteroalkyl and —NR'R" are not repetitive or exclusive. Instead, these specific heteroalkyl groups are cited for clarity. Therefore, the term "heteroalkyl" should not be interpreted in this paper to exclude specific heteroalkyl such as —NR'R".

The term "cycloalkoxy" refers to a cycloalkoxy group as defined above bounds to an oxygen atom, such as cyclopropyloxy.

The term "fluoroalkoxy" refers to an alkoxy group as defined above in which one or more hydrogen atoms are replaced by fluorine.

The term "aryl" refers to a monocyclic or bicyclic aryl group only containing carbon atom. The "fused analogues" of aryl group refer to aryl group fusing to single ring cycloalkyl or single ring heterocyclic group of, in which the connection point is located in the aryl part. Examples of aryl and its fused ring analogues include phenyl, naphthyl, indanyl, indenyl, tetrahydronaphthyl, 2,3-dihydrobenzofuran, dihydrobenzopyran, 1,4-benzodioxyl, etc.

The term "heteroaryl" refers to a monocyclic or bicyclic aryl group containing at least one heteroatom selected from N, O and S. "fused analogues" of heteroaryl group refer to the heteroaryl group fusing to single ring cycloalkyl group or single ring heterocyclic group, in which the connection point is located in the aryl part. Examples of heteroaryl groups include pyrrolyl, isozolyl, isothiazolyl, pyrazolyl, pyridyl, oxazolyl, oxadiazole, thiazolyl, imidazolyl, triazolyl, tetrazolyl, furanyl, triazinyl, thiophenyl, pyrimidinyl, pyridazinyl, pyrazinyl, benzoxazolyl, benzothiazolyl, benzimidazolyl, benzofuranyl, BENZOTHIOPHENYL, Furano (2,3-b) pyridine, quinoline, indole, isoquinoline, etc.

The defined alkyl, aryl and heteroaryl groups are unsubstituted or substituted by at least one substituent selected from the group consisting of substituents.

The substituents are selected from the group consisting of halogen atom, alkyl group with 1 to 6 carbon atoms, alkoxy group with 1 to 6 carbon atoms, haloalkyl group with 1 to 6 carbon atoms, haloalkoxy group with 1 to 6 carbon atoms, cyano group, alkynyl group with 2 to 6 carbon atoms, alkanoyl group with 1 to 6 carbon atoms, cycloalkyl group with 3 to 7 ring atoms, heteroaryl group, aryl group Arylalkoxy, arylcarbonyl, aminocarbonyl with 7-10 carbon atoms, alkenyl with 2-5 carbon atoms, alkylthio with 1-6 carbon atoms, aminosulfinyl, aminosulfonyl, hydroxyl, —SF$_5$, hydroxyalkyl with 1-4 carbon atoms, nitro, amino, carboxyl, alkoxycarbonyl with 2-5 carbon atoms, alkoxyalkyl with 1-4 carbon atoms, alkylsulfonyl group with 1-4 carbon atoms, alkanoylamino group with 1-4 carbon atoms, alkanoyl (alkyl) amino group with 1-6 carbon atoms, alkanoylaminoalkyl group with 1-6 carbon atoms in both alkanoyl and alkyl parts, alkanoyl (alkyl) aminoalkyl group with 1-6 carbon atoms in both alkanoyl and alkyl parts, alkanoyl (alkyl) aminoalkyl group with 1-6 carbon atoms in both alkanoyl and alkyl parts, alkyl sulfonylamino group with 1 to 4 carbon atoms, monoalkyl amino carbonyl group or dialkylamino carbonyl group with 1 to 6 carbon atoms, monoalkyl amino sulphonyl group or dialkylamino sulphonyl group with 1 to 6 carbon atoms, monoalkyl amino sulphonyl group or dialkylamino sulphonyl group with 1 to 6 carbon atoms, aminoalkyl group with 1 to 4 carbon atoms monoalkyl or dialkylamino with 1 to 6 carbon atoms, monoalkyl or dialkylamino with 1 to 6 carbon atoms in each alkyl part, aryl with 7 to 10 carbon atoms, heteroaryl with 1 to 4 carbon atoms in the alkyl part, heteroarylalkoxy group with 1 to 4 carbon atoms in the alkyl part and alkyl sulfonamide group with 1 to 4 carbon atoms in alkoxy part.

As used herein, the term "heterocyclic" or "heterocyclic" or "heterocyclic alkyl" or "heterocyclic group" refers to a saturated, partially saturated or unsaturated group (but not aromatic) having a single ring or fused ring (including a bridged ring system and a spiro ring system) with 1 to 10 carbon atoms and 1 to 4 heteroatoms selected from nitrogen, sulfur or oxygen in the ring, One or more rings may be naphthenic, aryl or heteroaryl, as long as the connecting point passes through a nonaromatic ring. In one embodiment, the nitrogen and/or sulfur atoms of the heterocyclic group are selectively oxidized to provide N-oxide, sulfinyl and sulfonyl moieties" Examples of heterocyclic groups and their analogues include pyrrolidinyl, piperidinyl, piperazinyl, imidazolidinyl, 2,3-dihydrofuran (2,3-b) pyridyl, benzoxazinyl, tetrahydroquinolinyl, tetrahydroisoquinolinyl, dihydroindolyl, etc. The term also includes nonaromatic, partially unsaturated monocyclic rings, such as 2- or 4-pyridone or N-substituted-(1H,3H)-pyrimidin-2,4-diones (N-substituted uracils) linked by nitrogen atoms.

As used herein, the term "substituted heterocyclic" or "substituted heterocyclic alkyl" or "substituted heterocyclic group" refers to a heterocyclic group substituted by 1 to 5 (e.g., 1 to 3) substituents. The substituents are defined in the substituted cycloalkyl group.

Unless otherwise specified, the term "halogenated" or "halogen" itself or as part of another substituent refer to fluorine, chlorine, bromine or iodine atoms. In addition, the term "haloalkyl" refers to monohaloalkyl and Polyhaloalkyl. For example, the term "halogenated ($C_1$-$C_4$) alkyl" includes, but not limited to, trifluoromethyl, 2,2,2-trifluoroethyl, 4-chlorobutyl, 3-Bromopropyl, etc.

"Prodrug" refers to the substance converted into the parent drug in vivo. In some cases, prodrugs are often used because they are easier to administer than parent drugs. For example, prodrugs can be bioavailable by oral administration, while parent drugs cannot. In the pharmaceutical composition, the prodrug may also have a higher solubility than the parent drug. Examples of prodrugs, but not limited to, can be any of the compounds of formula I, which are applied in the form of esters (prodrugs) to promote transmembrane transport. Water solubility in the cell membrane is harmful to migration, and once in a water-soluble beneficial cell, the esters are then metabolized and hydrolyzed to the active substance carboxylic acid. Another example of prodrugs can be a short peptide (poly amino acid) bonded to an acid group, wherein, the peptide is metabolized to release the active portion.

Optical Isomers, Diastereomers, Geometric Isomers and Tautomers Since the compounds of the present invention contain one or more asymmetric centers, they can be used as racemates and racemic mixtures, single enantiomers, diastereomeric mixtures and single diastereomers. When referring to compounds of the invention or compounds of formula A, it should be understood that all these isomeric forms are included.

Some of the compounds described in this paper contain olefinic double bonds, including e and Z geometric isomers unless otherwise specified.

Some compounds of formula A may contain one or more ring systems, so cis- and trans isomers may exist. The present invention is intended to encompass all of these cis- and trans-isomers.

Some of the compounds described herein may have different sites connected with hydrogen atoms, which are called tautomers. Such examples can be ketones and their enol forms called ketone enol tautomers. A single tautomer and a mixture thereof are included in the compound of formula A The compound of formula A can be separated from diastereoisomeric pairs of the enantiomers, for example by fractional crystallization from a suitable solvent, such as methanol or ethyl acetate or their mixture. A pair of enantiomers thus obtained can be separated into individual stereoisomers by conventional methods, such as using optically active amines or acids as resolution reagents or in chiral HPLC columns.

Alternatively, any enantiomer of the compound of general formula A can be obtained by stereospecific synthesis using optically pure raw materials or reagents of known configuration.

In addition, compounds of formula A can also include a series of stable isotope labeled analogues. For example, one or more protons in the compound of formula A can be replaced by deuterium atoms, thus providing deuterated analogues with improved pharmacological activity.

Salt and Dosage Form

As used herein, the term "pharmaceutically acceptable salt" refers to a nontoxic acid or alkaline earth metal salt of a compound of general formula I. These salts can be prepared in situ during the final separation and purification of compounds of general formula I, or by reacting suitable organic or inorganic acids or bases with basic or acidic functional groups, respectively. Representative salts include, but are not limited to, acetate, adipate, alginate, citrate, aspartate, benzoate, benzenesulfonate, bisulfate, butyrate, camphorate, camphorsulfonate, diglucosate, cyclopentane propionate, dodecyl sulfate, ethylsulfonate, glucose heptanate, glycerophosphate, hemisulfate, heptanate Hexanoate, fumarate, hydrochloride, hydrobromate, hydroiodate, 2-hydroxyethanesulfonate, lactate, maleate, methanesulfonate, nicotinate, 2-naphthylsulfonate, oxalate, dihydroxynaphthalenate, pectinate, thiocyanate, 3-phenylpropionate, picrate, neopentyl, propionate, succinate, sulfate, tartrate, thiocyanate P-toluenesulfonate and undecanoate. In addition, nitrogenous basic groups can be quaternized by alkyl halides such as chlorides, bromides and iodides of methyl, ethyl, propyl and butyl groups; dialkyl sulfates, such as dimethyl, diethyl, dibutyl and dipentyl sulfates; Long chain halides such as decyl, lauryl, myristoyl and stearyl chlorides, bromides and iodides; arylalkyl halides such as benzyl and phenylethyl bromide. Thus, water-soluble or oil-soluble or dispersible products are obtained. Examples of acids that can be used to form pharmaceutically acceptable acid addition salts include inorganic acids such as hydrochloric acid, sulfuric acid and phosphoric acid, and organic acids such as oxalic acid, maleic acid, methanesulfonic acid, succinic acid and citric acid. Alkali addition salts can be prepared in situ at the time of final separation and purification of compounds of general formula I, or by reacting the carboxylic acid portion with suitable bases (such as pharmaceutically acceptable hydroxides of metal cations, carbonates or bicarbonates) or ammonia, or organic primary, secondary or tertiary amines, respectively. Pharmaceutically acceptable salts include, but are not limited to, alkali metal and alkaline earth metal cations, such as sodium, lithium, potassium, calcium, magnesium and aluminum salts, and nontoxic ammonium, quaternary ammonium and amine cations, including but not limited to: ammonium, tetramethylammonium, tetraethylammonium, methylamine, dimethylamine, trimethylamine, triethylamine, ethylamine, etc. Other representative organic amines used to form alkali addition salts include diethylamine, ethylenediamine, ethanolamine, diethanolamine, piperazine, etc.

It should be understood that, as used herein, reference to compounds of formula A also includes pharmaceutically acceptable salts.

The preparation for oral administration may also be a hard gelatin capsule in which the active ingredient is mixed with an inert solid diluent, such as calcium carbonate, calcium phosphate or kaolin, or a soft gelatin capsule in which the active ingredient is mixed with water or oil medium, such as peanut oil, liquid paraffin or olive oil.

The aqueous suspension contains an active substance mixed with an excipient suitable for preparing the aqueous suspension. Such excipients are suspension agents, such as sodium carboxymethyl cellulose, methyl cellulose, hydroxypropyl methyl cellulose, sodium alginate, polyvinylpyrrolidone, tragacanth gum and Arabic gum; The dispersant or wetting agent may be a naturally occurring phospholipid, such as lecithin, or a condensation product of alkylene oxide with fatty acids, such as polyoxyethylene stearate, or a condensation product of ethylene oxide with long-chain aliphatic alcohols, such as heptadecaethylene oxycetanol, Or a condensation product of ethylene oxide with a partial ester derived from fatty acid and hexitol, for example, polyoxyethylene sorbitol monooleate, or a condensation product of ethylene oxide with a partial ester derived from fatty acid and hexitol anhydride, for example, polyethylene dehydrated sorbitol monooleate. The aqueous suspension may also contain one or more preservatives, such as ethyl p-hydroxybenzoate or propyl p-hydroxybenzoate, one or more colorants, one or more flavorings, and one or more sweeteners, such as sucrose, saccharin or aspartame.

Oily suspensions can be prepared by suspending the active ingredients in vegetable oils, such as peanut oil, olive oil, sesame oil or coconut oil, or in mineral oils, such as liquid paraffin. Oily suspensions may contain thickeners such as beeswax, paraffin or cetanol. The sweetener can be added, and the taste correcting agent can be added to provide a delicious oral preparation. These compositions can be preserved by the addition of antioxidants such as ascorbic acid.

Dispersible powders and granules suitable for preparing aqueous suspensions by adding water provide active ingredients mixed with dispersants or wetting agents, suspensions and one or more preservatives. Suitable dispersants or wetting agents and suspending agents are shown by the examples already mentioned above. There may also be additional excipients such as sweeteners, flavourings and colorants.

The pharmaceutical composition of the invention can also be emulsion form of water in oil. The oil phase can be vegetable oil, such as olive oil or peanut oil, or mineral oil, such as liquid paraffin or a mixture of these. Suitable emulsifiers may be naturally occurring phospholipids, such as soybeans, lecithin, and esters or partial esters derived from fatty acids and hexitol anhydrides, such as sorbitol monooleates, and condensation products of the partial esters with ethylene oxide, such as polyoxyethylene dehydrated sorbitol monooleates. The emulsion may also contain sweeteners and correctors.

Syrups and elixirs can be formulated with sweeteners such as glycerol, propylene glycol, sorbitol or sucrose. Such preparations may also contain moderators, preservatives, flavourings and colorants. The pharmaceutical composition may be in the form of a sterile injectable aqueous or oily suspension. The suspension can be prepared by known technology using the suitable dispersant or wetting agent and suspension agent mentioned above. Sterile injectable preparations may also be sterile injectable solutions or suspensions prepared with nontoxic extragastrointestinal acceptable diluents or solvents, such as 1,3-butanediol. Acceptable carriers and solvents that can be used are water, Ringer's solution and isotonic sodium chloride solution. In addition, sterile, nonvolatile oils are commonly used as solvents or suspension media. Any mild nonvolatile oil used for this purpose can be used, including synthetic monoglycerides or diglycerides. In addition, fatty acids such as oleic acid can be used in the preparation of injections.

The compounds of the present invention can also be administered either in the nose or by inhalation, usually in the form of dry powder from a dry powder inhaler (alone, as a mixture, for example, a dry blend containing lactose, or as a mixed component particle, such as mixing with phosphatidylcholine), or from a pressurized container, pump, injector, Aerosol atomizer (using current to produce mist optimized I nebulizer) or aerosol sprayer, using or not using suitable propellants, such as 1,1,1,2-tetrafluoroethane or 1,1,1,2,3,3,3-hexafluoropropane. For intranasal use, powders may include bioadhesives, such as chitosan or cyclodextrin.

Pressurized containers, pumps, injectors, nebulizers or sprayers contain solutions or suspensions of the compounds of the invention. The solutions or suspensions contain, for example, ethanol, hydrated ethanol, or suitable alternative agents for dispersing, solubilizing, or extending the activity of release, as solvent pushing agents and optional surfactants, such as dehydrated sorbitol three oleate, oleic acid or lactic acid oligomer.

The drug product is micronized to a size suitable for inhalation delivery (usually less than 5 microns) prior to use in the form of a dry powder or suspension preparation.

It can be achieved by any suitable crushing method, such as spiral jet grinding, fluidized bed jet grinding, supercritical fluid processing to form nanoparticles, high pressure homogenization, or spray drying.

Capsules (e.g. prepared from gelatin or hydroxypropylmethylcellulose) for inhalers or insufflators, blisters and kits can be formulated into powders containing the compounds of the invention, suitable powders such as lactose or starch, and performance modifiers such as L-leucine, mannitol or magnesium stearate. Lactose may be in anhydrous or monohydrate form, preferably the latter. Other suitable excipients include dextran, glucose, maltose, sorbitol, xylitol, fructose, sucrose and trehalose.

A suitable solution formulation for use in an atomizer using an electrodynamic method to produce a fine mist may contain a compound of the invention from 10 g to 20 mg per start, with a start-up volume varying from 11 to 1001. Typical preparations may contain compounds of formula A, propylene glycol, sterile water, ethanol and sodium chloride. Alternative solvents that can be used to replace propylene glycol include glycerol and polyethylene glycol.

Suitable flavoring agents, such as menthol and left menthol, or sweeteners, such as saccharin or saccharin sodium, may be added to those preparations of the present invention for inhalation/intranasal administration.

Preparations for inhalation/intranasal administration can be formulated for immediate use and/or improved release, e.g., using poly (DL lactic glycolic acid) (PGLA). Improved release formulations include delayed release, sustained release, pulsed release, controlled release, targeted release and programmed release.

In the case of dry powder inhalers and aerosols, the dose unit is determined by a valve that provides a metering quantity. The units of the invention are usually arranged for dosing doses or "sprays" containing compounds of 0.001 to 10 mg compound A.

The total daily dose usually ranges from 0.001 to 10 mg and can be administered as a single dose or more commonly as a batch dose within a day.

The compound of formula A can also be used for rectal administration of drugs in the form of suppository. These compositions can be prepared by mixing the drug with a suitable non irritating excipient, which is solid at room temperature but liquid at rectal temperature and therefore melt in the rectum to release the drug. These substances are cocoa butter and polyethylene glycol.

For topical use, cream, ointment, gel, solution or suspension containing compound A are used. (For the purpose of the present application, topical application shall include mouthwash and gargle).

Dose levels of about 0.01 mg to about 140 mg/kg body weight per day are useful in the treatment of the above conditions, or about 0.5 mg to about 7 g per patient per day. For example, inflammation can be effectively treated by applying about 0.01 to 50 mg compound per kilogram of body weight per day, or by applying about 0.5 mg to 3.5 g compound per patient per day, preferably 2.5 mg to 1 g compound per person per day.

The amount of active ingredients that can be combined with the carrier material to produce a single dosage form will vary according to the host being treated and the specific mode of administration. For example, preparations for human oral administration may contain 0.5 mg to 5 g of an active agent, the active agent is compounded with a convenient amount of carrier material, and the carrier material may vary from about 5% to about 95% of the total composition. Dosage unit forms generally contain about 1 mg to about 500 mg of active ingredients, usually 25 mg, 50 mg, 100 mg, 200 mg, 300 mg, 400 mg, 500 mg, 600 mg, 800 mg or 1000 mg.

However, it should be understood that the specific dose level for any particular patient depends on a number of factors, including age, weight, general health, gender, diet, administration time, route of administration, excretion rate, drug combination, and the severity of the specific disease being treated.

Application

The compound of the invention can be used for treating diseases related to the abnormal activity of BTK and BTK mutants (such as C481S).

The present invention also relates to a method of treating a disease of a patient by administering a therapeutically effective amount of compound of formula A to the patient.

More specifically, the compound of the present invention can be used to treat diseases with abnormal cell growth and/or apoptosis disorder, such as mesothelioma, bladder cancer, pancreatic cancer, skin cancer, head or neck cancer, skin or intraocular melanoma, ovarian cancer, breast cancer, uterine cancer, endometrial fallopian tube cancer, cervical cancer, vaginal cancer, vulvar cancer, bone cancer, cervical cancer, colon cancer, rectal cancer, anal region cancer, gastric cancer, gastrointestinal cancer (stomach, colorectal and duodenum), chronic lymphocytic leukemia, esophageal cancer, small intestine cancer, endocrine system cancer, thyroid cancer, parathyroid cancer, adenocarcinoma, adrenal cancer, soft tissue cancer, urethral cancer, penile cancer, testicular cancer, hepatocellular carcinoma (liver cancer and bile duct), primary or secondary central nervous system tumor, primary or secondary brain tumor, Hodgkin's sarcoma, chronic or acute leukemia, chronic myeloid leukemia, lymphoblastic lymphoma, lymphoblastic leukemia, follicular lymphoma of T-cell or B-cell origin, melanoma, multiple myeloma, oral cancer, ovarian cancer, non-small cell lung cancer, prostate cancer, small cell lung cancer, renal and ureteral cancer, renal cell cancer, renal pelvis cancer, central nervous system tumor, Primary central nervous system lymphoma, non-Hodgkin's lymphoma, spinal axis tumor, brainstem glioma, pituitary adenoma, adrenocortical carcinoma, gallbladder carcinoma, splenic carcinoma, cholangiocarcinoma, fibrosarcoma, neuroblastoma, retinoblasitoma, or a combination thereof. In another embodiment, the present invention also includes method of treating cancers such as mesothelioma, bladder cancer, pancreatic cancer, skin cancer, head or neck cancer, skin or intraocular melanoma, breast cancer, uterine cancer, fallopian tube cancer, endometrial cancer, cervical cancer, vagina or vulvar cancer, bone cancer, ovarian cancer, cervical cancer, colon cancer, rectal cancer, anal cancer, gastric cancer, gastrointestinal cancer (stomach, colorectal and duodenum), chronic lymphocytic leukemia, esophageal cancer, small bowel cancer, endocrine system cancer, thyroid cancer, parathyroid cancer, adrenal cancer, soft tissue sarcoma, urethral cancer, penile cancer, testicular cancer, hepatocellular carcinoma (liver cancer and bile duct), primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, T-cell or B-cell-derived lymphoid malignancies, melanoma, multiple myeloma, oral cancer, ovarian cancer, non-small cell lung cancer, prostate cancer, small cell lung cancer, renal and ureteral cancer, renal cell cancer, renal pelvis cancer, in the central nervous system, primary central nervous system lymphoma, non Hodgkin's lymphoma, spinal axis tumor, brain stem glioma, pituitary adenoma, adrenocortical carcinoma, gallbladder carcinoma, splenic carcinoma, cholangiocarcinoma, fibrosarcoma, neuroblastoma, retinoblasitoma or a combination of one or more of the above cancers, or a combination thereof, the method also includes administering a therapeutically effective amount of compound of formula A.

The compound of formula A can also be used to treat autoimmune diseases and inflammatory diseases, such as, inflammatory bowel disease, arthritis, lupus, rheumatoid arthritis, psoriatic arthritis, osteoarthritis and juvenile arthritis, Steele's disease, diabetes, myasthenia gravis, Hashimoto's thyroiditis, oedal's thyroiditis, Graves's disease, Sjogren's syndrome, multiple sclerosis, GuiUain-Barre syndrome, acute disseminated encephalomyelitis, etc. Addison's disease, opsoclonus myoclonus syndrome, ankylosing spondylitis, antiphospholipid antibody syndrome, aplastic anemia, autoimmune hepatitis, abdominal disease, Goodpasture's syndrome, idiopathic thrombocytopenic purpura, optic neuritis, scleroderma Primary biliary cirrhosis, Reiter's syndrome, Takayasu's arteritis, temporal arteritis, warm autoimmune hemolytic anemia, Wegener's granulomatosis, psoriasis, hair loss, Behcet's disease, chronic fatigue Autonomic nervous disorder, endometriosis, interstitial cystitis, neuromyotonia, scleroderma, vulvar pain, transplantation, blood transfusion, allergic reaction, hypersensitivity, type I hypersensitivity, allergic conjunctivitis, allergic rhinitis, atopic dermatitis, asthma, appendicitis, blepharitis, bronchiolitis, bronchitis, bursitis, cervicitis, cholangitis, cholecystitis colitis, colitis, cystitis, lacrimal gland inflammation, dermatitis, dermatomyositis, encephalitis, endocarditis, endometritis, enteritis, enterocolitis, epicondylitis, epididymitis, fasciitis, fibrous histitis, gastritis, gastroenteritis, hepatitis, suppurative hidradenitis, laryngitis, mastitis, meningitis, myelitis, myocarditis, myositis, nephritis, ovaritis, orchitis, osteitis otitis, pancreatitis, mumps, pericarditis, peritonitis, pharyngitis, pleurisy, phlebitis, pneumonia, pneumonia, proctitis, prostatitis, pyelonephritis, rhinitis, salpingitis, sinusitis, stomatitis, synovitis, tendinitis, tonsillitis, uveitis, vaginitis, vasculitis or vulvitis.

In some embodiment, if the patient suffers from cancer, the method also includes administering anticancer agents to the subject in addition to the compound of formula A. In some embodiment, the anticancer agents are inhibitors of mitogen activated protein kinase signaling pathway, such as U0126, PD98059, PD184352, PD0325901, ARRY-142886, SB239063, SP600125, BAY 43-9006, wortmannin, and LY294002.

The present invention also relates to the pharmaceutical composition comprising at least a compound of formula A or at least one compound of formula A and one or more pharmaceutically acceptable excipients.

More specifically, the pharmaceutical compositions of the present invention are those suitable for oral, parenteral, nasal, percutaneous or transdermal, rectal, translingual, ocular or respiratory administration, especially tablets or lozenges, sublingual tablets, sachets, packets, gelatin capsules, glossettes, lozenges, suppository, cream, ointment, skin gel, drinkable or injectable ampoules.

The dosage can vary according to the patient's gender, age and weight, route of administration, nature of indication, or any related treatment. In one or more applications, the dosage range is 0.01 mg to 1 g every 24 hours.

In addition, the invention also relates to a combination of formula A and one or more anticancer agents selected from cytotoxic agents, mitotoxins, antimetabolites, proteasome inhibitors and kinase inhibitors, and to the use of such a combination in the preparation of drugs for the treatment of cancer.

The compound of the invention can also be used in combination with radiotherapy for treating cancer.

Compounds of formula (a) are also expected to be used as chemotherapeutic agents in combination with therapeutic agents, the therapeutic agents includes but not limited to angiogenesis inhibitors, antiproliferative agents, other kinase inhibitors, other receptor tyrosine kinase inhibitors, aurora kinase inhibitors, polo like kinase inhibitors, bcr-abl kinase inhibitors, growth factor inhibitors, COX-2 inhibitors, non steroidal anti-inflammatory drugs (NSAIDs), anti mitotic agents, alkylating agents, anti metabolites, intercalated antibiotics, platinum containing reagents, growth factor inhibitors, ionizing radiation, cell cycle inhibitors, enzymes, topoisomerase inhibitors, biological reaction regulator, immunomodulators, immune agents, antibodies, hormone therapy, vitamin A/deltoid alkaloids, proteasome inhibitors, HSP-90 inhibitors, histone deacetylase inhibitors (HDAC) inhibitors, purine analogues, pyrimidine analogues, MEK inhibitors, CDK inhibitors, ERBB2 receptor inhibitors, mTOR inhibitors, BCL inhibitors, MCL inhibitors and the combination thereof, PD1 antibodies, PDL1 antibodies, CTLA4 antibodies, IDO inhibitors, TDO inhibitors, A2a antagonists, arginase inhibitors, and other antitumor agents.

Angiogenesis inhibitors include, but are not limited to EGFR inhibitors, PDGFR inhibitors, VEGFR inhibitors, TTE2 inhibitors, IGFIR inhibitors, matrix metalloproteinase-2 (MMP-2) inhibitors, matrix metalloproteinase-9 (MMP-9) inhibitors, platelet reactive protein analogues, such as thrombospondin-1 and N—Ac-Sar-Gly-Val-D-alloIle-Thr-Nva-Ile-Arg-Pro-NHCH$_2$CH$_3$ or the salts thereof, and N—Ac-Sar-Gly-Val-D-alloIle-Thr-Nva-Ile-Arg-PrO—NHCH$_2$CH$_3$ analogues, such as N—Ac-GlyVal-D-AIle-Ser-GIn-Ile-Arg-ProNHCH$_2$CH$_3$ or the salts thereof.

Examples of EGFR inhibitors include, but are not limited to, iressa (gefitinib), tarceva (erlotinib or OSI-774), icotinib, cetuximab (cetuximab), EMD-7200, ABX-EGF, HR3, IgA antibody, TP-38 (IVAX), EGFR fusion protein, EGF vaccine, AZD9291, CO1686, anti EGFr immunoliposome and tykerb (rapatinib).

Examples of PDGFR inhibitors include, but are not limited to, CP-673, 451 and CP-868596.

Examples of VEGFR inhibitors include, but are not limited to, avastin (bevacizumab), sunitinib (SU11248), nexavar (sorafenib, BAY43-9006), CP-547632, acitinib (AG13736), apatinib, cabotinib, iressa (vandetanib, ZD-6474), AEE788, AZD-2171, VEGF trap, vatalanib (PTK-787, ZK-222584), macugen, M862, pazopanib (GW786034), BC-00016, ABT-869 and angiozyme.

Examples of thrombospondin analogues include, but are not limited to, ABT-510.

Examples of BCL inhibitors include, but are not limited to, obatoclax and navitoclax, ABT 199.

Examples of aurora kinase inhibitors include, but are not limited to, VX-680, AZD-1152, and MLN-8054. Examples of polo like kinase inhibitors include, but are not limited to, BI-2536.

Examples of BCR-ABL kinase inhibitors include, but are not limited to, glivec (imatinib), ponatinib, nilotinib and dasatinib (BMS354825).

Examples of platinum containing reagents include, but are not limited to, cisplatin, carboplatin, eplatin, lobaplatin, nedaplatin, eloxatin (oxaliplatin) or salplatin.

Examples of mTOR inhibitors include, but are not limited to, CCI-779, rapamycin, temsirolimus, everolimus, RAD001, INK-128 and ridaforolimus.

Examples of HSP-90 inhibitors include, but are not limited to, geldanamycin, radicicol, 17-AAG, KOS-953, 17-DMAG, CNF-101, CNF-1010, 17-AAG-nab, NCS-683664, mycograb, CNF-2024, PU3, PU24FC1, VER49009, IPI-504, SNX-2112 and STA-9090.

Examples of histone deacetylase inhibitors (HDAC) include, but are not limited to, suberoylanilide hydroxamic acid (SAHA), MS-275, valproic acid, TSA, LAQ-824, trapoxin, tubacin, tubastatin, ACY-1215 and depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387032, PD0332991 and AZD-5438.

Examples of COX-2 inhibitors include, but are not limited to, CELEBREX™ (celecoxib), parecoxib, deracoxib, ABT-963, MK-663 (etoricoxib), COX-189 (lumiracoxib), BMS347070, RS57067, NS-398, valdecoxib, parecoxib, rofecoxib, SD-8381, 4-methyl-2-(3,4-dimethylphenyl)-1-(4-aminosulfonyl-phenyl-1h-pyrrole, T-614, JTE-522, 5-2474, SVT-2016, CT-3, SC-58125 and Arcoxia (etoricoxib).

Examples of non-steroidal anti-inflammatory drugs (NSAIDs) include, but are not limited to, amigesic, dolobid, ibuprofen, orudis, relafen, feldene, aleve, diclofenac, indomethacin, clinoril, tolectin, etodolic acid (iodine value), toradol and daypro.

Examples of ERBB2 receptor inhibitors include, but are not limited to, CP-724-714, CI-1033, (carnetinib), Herceptin (trastuzumab), omitarg (2C4, petuzumab), TAK-165, GW-572016 (ionafarnib), GW-282974, EKB-569, PI-166, dHER2 (HER2 vaccine), APC8024 (HER2 vaccine), anti HER/2neu bispecific antibody, B7.her2IgG3, the three functional bispecific antibodies of AS HER2, monoclonal antibody AR-209 and monoclonal antibody 2B-1.

Examples of alkylating agents include, but are not limited to, nitrogen mustard N-oxide, cyclophosphamide, ifosfamide, trophosphamide, chlorambucil, melphalan, busulfan, dibromannitol, carboquone, thiotepa, ramustine, nimustine, temozolomide, AMD-473, altretamine, AP-5280, apaziquone, brostallicin, bendamustine, carmustine, estramustine, fotemustine, glufosfamide, KW-2170, malafosamide, mitolactol, and, carmustine (BCNU), lomustine (CCNU), busulfan, treosulfan, dacarbazine and temozolomide.

Examples of antimetabolites include, but are not limited to, methotrexate, 6-mercaptopurine nucleoside, purinethol, uracil analogues, such as 5-fluorouracil (5-FU) alone or in combination with folic acid, tegafur, UFT, deoxyfluridine, carmofur, cytosine arabinoside, enocitabine, S-I, alimta (pemetrexed disodium, ly231514, MTA), gemcitabine, fludarabine, 5-azacytidine, capecitabine, cladribine, clofarabine, decitabine, eflornithine, ethnylcytidine, cytosine arabinoside, hydroxyurea, TS-I, melphalan, nelarabine, nolatrexed, loratroc, ocfosate, disodium premetrexed, pentastatin, pelitrexol, raltitrexed, triapine, trimetrexate, arabinosyl adenine, vincristine, vinorelbine, mycophenolic acid, thiazolidine, ribavirin, EICAR, hydroxyurea and deferoxamine.

Examples of antibiotics include, but are not limited to, arubicin, actinomycin (e.g. actinomycin D), aminorubicin, annamycin, doxorubicin, bleomycin A, bleomycin B, daunoblastina, doxorubicin, elsamitrucin, epirubicin, glarubicin, idarubicin, mitomycin C, nemorubicin, zinostatin, peplomycin, pirarubicin, rebeccamycin, butyl ester, streptozocin, valrubicin, zinostatin and their combinations.

Examples of topoisomerase inhibitors include, but are not limited to, one or more reagents selected from the group consisting of arubicin, amonafide, belotecan, camptothecin, 10-hydroxycamptothecin, 9-aminocamptothecin, diflomotecan, Camptosar, edotecarin, ellence, etoposide, exatecan, gimatecan, lurtotecan, orathecin (Supergen), BN-80915, mitoxantrone, pirarubicin, pixantrone, rubitecan, sobuzoxane, SN-38, tafluposide and topotecan.

Examples of antibodies include, but are not limited to, rituximab, cetuximab, bevacizumab, trastuzimab, specific CD40 antibody and specific IGF1R antibody.

Examples of hormone therapy include, but are not limited to, exemestane (aromasin), leuprorelin acetate, anastrozole (arimidex), fosrelin (zoladex), goserelin, doxercalcifero, fadrozole, formestane, tamoxifen, citrate (tamoxifen), casodex, abarelix, trelstar, finasteride, fulvestrant, toremifene, raloxifene, lasofoxifene, letrozole, flutamide, bicalutamide, megestrol, mifepristone, nilutamide, dexamethasone, prednisone and other corticosteroids Examples of vitamin A/deltoids include, but are not limited to, seocalcitol (EB1089, cb1093), lexalcitrol (KH 1060), fenretinide, aliretinoin, bexarotene and LGD-1550.

Examples of plant alkaloids include, but are not limited to, vincristine, vinblastine, vindesine and vinorelbine.

Examples of proteasome inhibitors include, but are not limited to, bortezomib (Vanke), MGL32, NPI-0052, and PR-171.

Examples of immune agents include, but are not limited to, interferon and many other immune promoters. Interferon includes interferon α, interferon α-2a, interferon α-2b, interferon β, interferon γ-1a, interferon γ-1b (actimmune) or interferon γ-n1 and its combination. Other promoters include filgrastin, lentinan, sizofilan, theracys, ubenimex, WF-10, aldeslukin, alemtuzumab, BAM-002, decarbazine, daclizumab, denileukin, gemtuzumab, ozogamicin, ibritumomab, imiquimod, lenograstim, lentinan, melanoma vaccine (corixa company), molgramostim, OncoVAC-CL, sargaramostim, tasonermin, tecleukin, thymalasin, tositumumab, virulizin, Z-100, epatuzumab, mitumomab, oregovomab, pemtumomab (Y-muHMFG1), provenge (dendreon company), STING activator, IDO inhibitor, arginine metabolizing enzyme inhibitor, CTLA4 antibody ((cytotoxic lymphocyte antigen 4)) and reagents that can block CTLA4, PD1 antibody or PD-L1 and other immune checkpoint protein inhibitors or antibodies.

Examples of biological response regulators are agents that regulate the defense mechanisms or biological reactions of living organisms (such as the survival, growth or differentiation of tissue cells) to guide them to have anti-tumor activity. Such drugs include Krestin, lentinan, sizofrran, picibanil and ubenimex.

Examples of pyrimidine analogues include, but are not limited to, 5-fluorouracil, floxuridine, doxifluridine, ratitrexed, cytosine arabinoside (cytosine arabinoside C), cytosine arabinoside, fludarabine and gemcitabine.

Examples of purine analogues include, but are not limited to, purinethol and thioguanine.

Examples of immunomodulators include, but are not limited to, thalidomide and lenalidomide.

Examples of anti mitotic agents include, but are not limited to, paclitaxel, docetaxel, albumin paclitaxel (Abraxane), epothilone D (KOS-862) and ZK-EPO.

Synthesis

The compounds of the present invention are prepared according to the equation as followed.

Synthesis Procedures

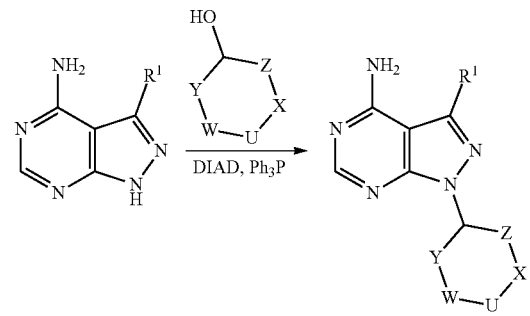

The compounds of the present invention could be prepared by chemical synthesis, the example thereof are as described as followed. It is to be understood that the sequence of the steps of the procedures could be changed, those specifically mentioned reagents, solvents and reaction conditions could be substituted, if necessary, the moiety prone to reaction could be protected and de-protected.

The following abbreviations have the meanings as shown below. DBU stands for 1,8-diazabicyclo[5.4.0]undecane-7-ene; DIBAL stands for diisobutyl aluminum hydride; DIEA stands for diisopropylethylamine; DMAP stands for N,N-dimethylaminopyridine; DME stands for 1,2-dimethoxyethane; DMF stands for N, N-dimethylformamide; DMPE stands for 1,2-bis(dimethylphosphino)ethane; DMSO stands for dimethyl sulfoxide; DPPB stands for 1,4-bis(diphenylphosphino)butane; dppe stands for 1,2-bis(diphenylphosphino)ethane; dppf stands for 1,1'-bis(diphenylphosphino) ferrocene; dppm stands for 1,1'-bis(diphenylphosphino) methane; DIAD stands for diisopropyl azodicarboxylate; EDCI stands for 1-(3-dimethylaminopropyl)-3-ethylcarbodiimide; HATU stands for 2-(7-aza-1H-benzotriazol-1-yl)-1,1,3,3-tetramethylurea hexafluorophosphate; HMPA stands for hexamethylphosphoramide; IPA stands for isopropanol; LDA is diisopropylaminolithium; LHMDS refers to bis(trimethylsilyl)aminolithium; LAH stands for lithium aluminum hydride; NCS is N-chlorosuccinimide; PyBOP refers to benzotriazole-1-yl-oxytripyrrole alkyl phosphate benzotriazole hexafluorophosphate; TDA-I is tris (2-(2-methoxyethoxy)ethyl)amine; DCM is dichloromethane; TEA stands for triethylamine, TFA is trifluoroacetic acid; THF is tetrahydrofuran; NCS is N-chlorosuccinimide; NMM stands for N-methylmorpholine; NMP is N-methylpyrrolidone; PPh$_3$ stands for triphenylphosphine and rt stands for room temperature.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions.

Example 1

(1R,3R)-3-(4-amino-3-(4-phenoxyphenyl)-1h-pyrazole[3,4-d]pyrimidin-1-yl)cyclohex-1-ol

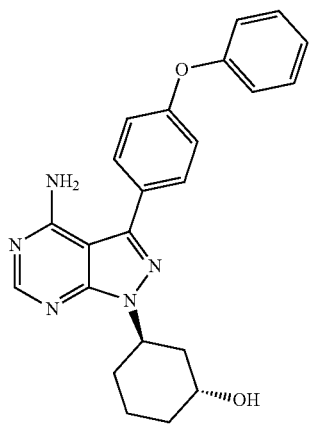 [SMILES: Nc1ncnc2c1c(-c1ccc(Oc3ccccc3)cc1)nn2[C@@H]1CCC[C@@H](O)C1]

Step 1: (1R, 3S)-3-hydroxycyclohexyl acetate

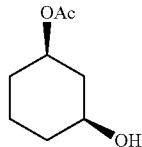 [SMILES: CC(=O)O[C@@H]1CCC[C@H](O)C1]

Under N$_2$, to a dried 100 mL two-necked-flask was added cis-1,3-cyclohexanediol (1.00 g, 8.61 mmol) and *Candida antarctica* lipase B (CALB) (180 mg). To another 50 mL two-necked-flask was added 4-chlorophenyl acetate (2.20 g, 12.91 mmol) and 30 mL toluene. After degassed for 5 min with N$_2$, toluene solution was added into the two-necked-flask. The resulting solution was stirred overnight at room temperature, and the reaction was monitored by TLC. The reaction was finished after 8 h, and the solvent was removed, the crude product was purified with silica gel column (petroleum ether:ethyl acetate=3:1) to afford 1.2 g product, yield 88%.

$^1$H NMR (400 MHz, CDCl$_3$): δ 4.78-4.71 (m, 1H), 3.74-3.67 (m, 1H), 2.25-2.21 (m, 1H), 2.05 (s, 3H), 1.92-1.89 (m, 2H), 1.83-1.80 (m, 2H), 1.44-1.23 (m, 4H).

Step 2: Optical Activity Test: (1S, 3R)-3-acetoxycyclohexyl(R)-3,3,3-trifluoro-2-methoxy-2-phenylpropionate

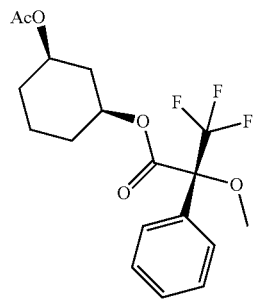 [SMILES: CO[C@@](C(=O)O[C@H]1CCC[C@@H](OC(C)=O)C1)(c1ccccc1)C(F)(F)F]

To a 25 mL flask was added (1R, 3S)-3-hydroxycyclohexyl acetate (15 mg, 0.10 mmol), pyridine (15 mg, 0.19 mmol) and 5 mL dichloromethane (DCM). The mixture was added (S)-3,3,3-trifluoro-2-methoxy-2-phenylpropionyl chloride (24 mg, 0.10 mmol) in 2 mL DCM under ice bath, and monitored by TLC. When the starting material was consumed, the reaction was purified with pre-TLC (petroleum ether:ethyl acetate=3:1) to afford 35 mg product, yield 99%.

$^1$H NMR (400 MHz, Acetone-d$_6$): δ7.56-7.54 (m, 2H), 7.49-7.46 (m, 3H), 5.13-5.06 (m, 1H), 4.81-4.73 (m, 1H), 3.57 (s, 3H), 2.30-2.25 (m, 1H), 2.08 (m, 1H), 1.93 (s, 3H), 1.90-1.84 (m, 2H), 1.54-1.42 (m, 3H), 1.40-1.29 (m, 1H).

$^{19}$F NMR (400 MHz, Acetone-d$_6$): δ −72.71 (s).

Step 3: cyclohexyl (1R, 3R)-3-(3-(4-phenoxyphenyl)-4-((triphenyl-5-phosphinidene) amino)-1H-pyrazolo[3,4-d]pyrimidin-1-yl)cyclohexyl acetate and (1R, 3R)-3-(4-amino-3-(4-phenoxyphenyl)-1H-pyrazolo[3,4-d]pyrimidin-1-yl)acetate

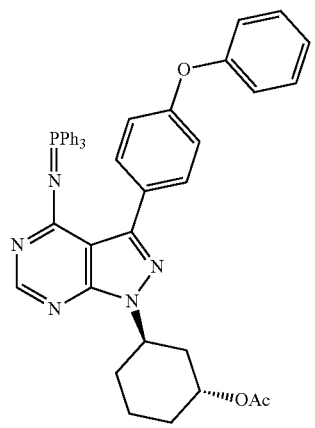
&

-continued

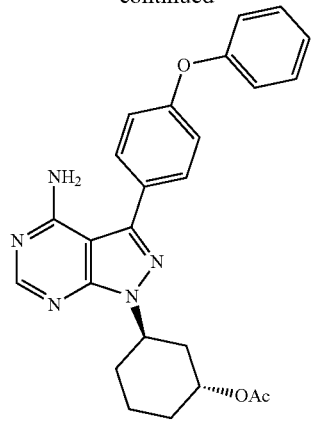

To a dried 250 mL three necked flask was added PPh₃ (12.44 g, 47.41 mmol) and 150 mL ultra dry THF, and placed in ice bath. After cooled to 0° C., diisopropyl azodicarboxylate (9.59 g, 47.41 mmol) was added dropwise into the system. After the addition, the mixture was stirred for another 40 min. White solid was precipitated and the mixture was stirred for another 10 min. The resulting solution was added successively with 3-(4-phenoxyphenyl)-1H-pyrazolo[3,4-d]pyrimidin-4-amine (6.04 g, 19.91 mmol) and (1R, 3S)-3-hydroxycyclohexyl acetate (3.00 g, 18.96 mmol). The reaction system turned to clear amber after addition. The reacting solution was stirred overnight, and TLC showed that the reaction was completed. 5 mL saturated ammonium chloride was added to quench the reaction. THF was removed, and 100 mL DCM and 50 mL brine were added to separate. DCM (50 mL×2) were used to extract. The combined organic phase was dried with anhydrous sodium sulfate. After filtration, the filtrate was mixed with silica gel. The mixture was purified with silica gel column (petroleum ether (containing 10% dichloromethane):ethyl acetate=100:1-100:2) to afford 3.00 g (1R, 3R)-3-(3-(4-phenoxyphenyl)-4-(triphenyl-5-phosphine)amino)-1H-pyrazo[3,4-d]pyrimidine-1-yl)cyclohexyl acetate, yield 20%; dichloromethane:methanol=100:1-100:2 were used to afford 3.40 g (1R, 3R)-3-(4-amino-3-(4-phenoxyphenyl)-1H-pyrazolo[3,4-d]pyrimidin-1-yl)cyclohexyl acetate, yield 40%.

(1R,3R)-3-(3-(4-phenoxyphenyl)-4-((triphenyl-5-phosphino)amino)-1H-pyrazolo[3,4-d]pyrimidin-1-yl)

¹H NMR (400 MHz, CDCl₃): δ 8.43-8.40 (d, 2H), 8.07 (s, 1H), 7.81-7.78 (m, 6H), 7.52-7.50 (m, 3H), 7.43-7.37 (m, 8H), 7.13-7.07 (m, 5H), 5.35 (m, 1H), 5.12-5.08 (m, 1H), 2.57-2.50 (m, 1H), 2.19-2.15 (m, 1H), 2.19 (s, 3H), 1.9-1.98 (m, 1H), 1.93-1.90 (m, 1H), 1.84-1.74 (m, 1H), 1.66-1.61 (m, 1H), 1.43-1.40 (m, 1H).

MS ESI: m/z=704, [M+H]⁺.

(1R,3R)-3-(4-amino-3-(4-phenoxyphenyl)-1H-pyrazo[3,4-d]pyrimidine-1-yl)cyclohexyl acetate ¹H NMR (400 MHz, CDCl₃): δ 8.39 (s, 1H), 7.67-7.64 (m, 2H), 7.41-7.37 (m, 2H), 7.17-7.14 (m, 3H), 7.09-7.07 (m, 2H), 5.52 (brs, 2H), 5.35-5.30 (m, 1H), 5.18-5.10 (m, 1H), 2.51-2.44 (m, 1H), 2.23-2.20 (m, 1H), 2.13 (s, 3H), 2.11-2.08 (m, 2H), 1.97-1.77 (m, 4H), 1.66-1.58 (m, 1H).

MS ESI: m/z=444, [M+H]⁺.

Step 4: cyclohexyl (1R, 3R)-3-(4-amino-3-(4-phenoxyphenyl)-1H-pyrazolo[3,4-d]pyrimidin-1-yl) acetate

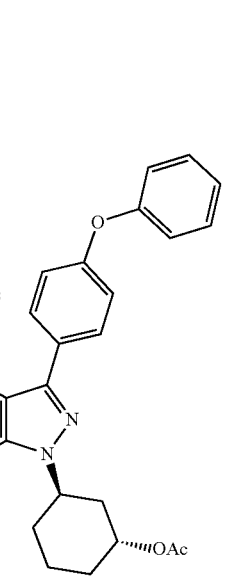

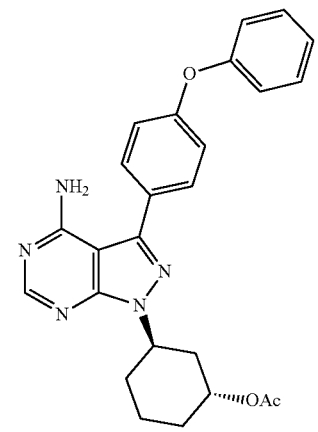

To a dried 25 mL flask was added (1R, 3R)-3-(3-(4-phenoxyphenyl)-4-((triphenyl-5-phosphine)amino)-1H-pyrazolo[3,4-d]pyrimidin-1-yl) (0.30 g, 0.43 mmol) and 5 mL mixing solution (acetic acid/water, v/v=1/1). The mixture was heated to reflux, and monitored by TLC. After raw material was consumed, the mixture was extracted with DCM (10 mL×3). The combined organic phase was purified with silica gel column (dichloromethane:methanol=100:1~100:2) to afford 180 mg product, yield 95%.

¹H NMR (400 MHz, CDCl₃): δ 8.39 (s, 1H), 7.67-7.64 (m, 2H), 7.41-7.37 (m, 2H), 7.17-7.14 (m, 3H), 7.09-7.07 (m, 2H), 5.52 (brs, 2H), 5.35-5.30 (m, 1H), 5.18-5.10 (m, 1H), 2.51-2.44 (m, 1H), 2.23-2.20 (m, 1H), 2.13 (s, 3H), 2.11-2.08 (m, 2H), 1.97-1.77 (m, 4H), 1.66-1.58 (m, 1H).

MS ESI: m/z=444, [M+H]⁺.

Step 5: (1R,3R)-3-(4-amino-3-(4-phenoxyphenyl)-1H-pyrazole[3,4-d]pyrimidin-1-yl)cyclohex-1-ol

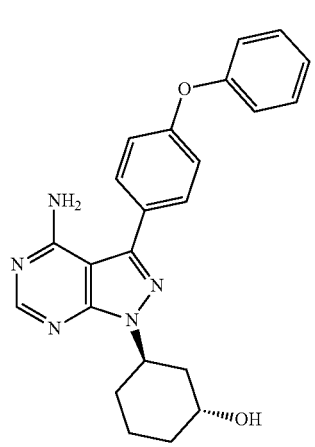 [SMILES: Nc1ncnc2c1c(-c1ccc(Oc3ccccc3)cc1)nn2[C@@H]1CCC[C@@H](O)C1]

To a dried 50 mL flask was added (1R, 3R)-3-(4-amino-3-(4-phenoxyphenyl)-1H-pyrazolo[3,4-d]pyrimidin-1-yl)cyclohexyl acetate (1.50 g, 3.38 mmol) and 30 mL MeOH. Anhydrous LiOH (0.25 g, 10.28 mmol) was added by stirring and stirred at room temperature overnight. TLC showed that the reaction was over. The reaction system was filtrated to remove LiOH and mixed with silica gel. The resulting solution was purified with silica gel column to afford 1.3 g product, yield 96%.

$^1$H NMR (400 MHz, CDCl$_3$): δ 8.36 (s, 1H), 7.67-7.63 (m, 2H), 7.41-7.37 (m, 2H), 7.19-7.14 (m, 3H), 7.09-7.07 (m, 2H), 5.67 (brs, 2H), 5.28-5.23 (m, 1H), 4.40 (m, 1H), 2.41-2.34 (m, 1H), 2.15-2.07 (m, 4H), 1.84-1.73 (m, 2H), 1.69-1.61 (m, 1H).

MS ESI: m/z=402, [M+H]$^+$.

Example 2

(1S, 3R)-3-(4-amino-3-(4-phenoxyphenyl)-1H-pyrazolo[3,4-d]pyrimidin-1-yl) cyclohex-1-ol

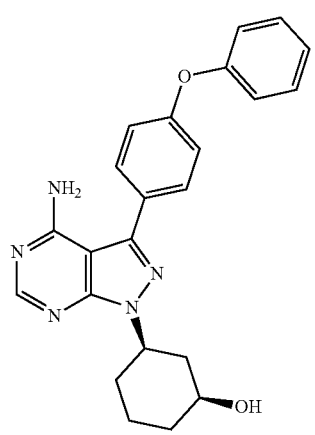 [SMILES: Nc1ncnc2c1c(-c1ccc(Oc3ccccc3)cc1)nn2[C@@H]1CCC[C@H](O)C1]

Step 1: cyclohexyl (1S, 3R)-3-(4-amino-3-(4-phenoxyphenyl)-1H-pyrazolo[3,4-d]pyrimidin-1-yl) benzoate

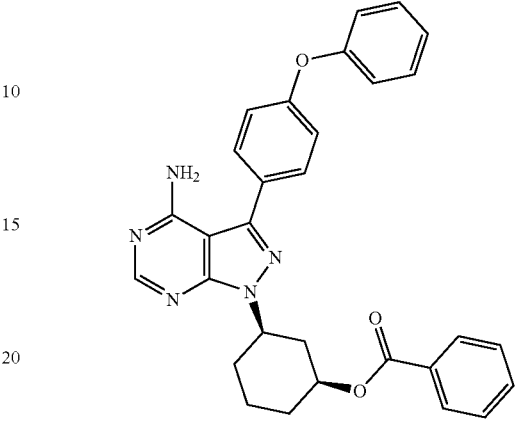

To a dried 25 mL flask was added PPh$_3$ (131 mg, 0.50 mmol) and 10 mL THF. The mixture was stirred to clear, and diisopropyl azodicarboxylate (101 mg, 0.50 mmol) was added dropwise into the flask under ice bath. The resulting solution was kept under 5° C. to react for 1 h. White solid was precipitated. After further stirred for 10 min. the mixture of benzoic acid (61 mg, 0.50 mmol) and (1R, 3R)-3-(4-amino-3-(4-phenoxyphenyl)-1h-pyrazole[3,4-d]pyrimidin-1-yl)cyclohex-1-ol (100 mg, 0.25 mmol) in THF was added dropwise into the reaction system, then ice bath was removed. The reacting solution was warmed to room temperature and reacted for 2 h, TLC showed that the reaction was finished. Silica gel was added, spin-dried, and purified with silica gel column (DCM:MeOH=100:1-100:2) to afford 110 mg product, yield 87%.

$^1$H NMR (400 MHz, Acetone-d$_6$): δ 8.27 (s, 1H), 8.05-8.03 (m, 2H), 7.78-7.74 (m, 2H), 7.64-7.61 (m, 1H), 7.52-7.48 (m, 2H), 7.46-7.42 (m, 2H), 7.21-7.17 (m, 3H), 7.13-7.11 (m, 2H), 6.38 (brs, 2H), 5.25-5.17 (m, 1H), 5.04-4.96 (m, 1H), 2.50-2.45 (m, 1H), 2.42-2.30 (m, 1H), 2.28-2.20 (m, 1H), 2.18-2.11 (m, 1H), 1.76-1.66 (m, 4H).

MS ESI: m/z=506, [M+H]$^+$.

Step 2: (1S, 3R)-3-(4-amino-3-(4-phenoxyphenyl)-1H-pyrazolo[3,4-d]pyrimidin-1-yl)cyclohex-1-ol To a dried 25 mL flask was added cyclohexyl (1S, 3R)-3-(4-amino-3-(4-phenoxyphenyl)-1H-pyrazolo[3,4-d]pyrimidin-1-yl)benzoate (100 mg, 0.20 mmol) and 5 mL methanol. Anhydrous lithium hydroxide (14 mg, 0.59 mmol) was added in batches, then mixture was stirred overnight. TLC showed that the reaction was finished. The mixture was filtrated to remove lithium hydroxide and mixed with silica gel, spin-dried, and purified with silica gel column (DCM:MeOH=100:2-100:3) to afford 75 mg product, yield 94%.

$^1$H NMR (400 MHz, CDCl$_3$): δ 8.38 (s, 1H), 7.67-7.64 (m, 2H), 7.41-7.37 (m, 2H), 7.17-7.14 (m, 3H), 7.09-7.07 (m, 2H), 5.47 (brs, 2H), 4.94-4.87 (m, 1H), 3.91-3.86 (m, 1H), 2.37-2.33 (m, 1H), 2.21-2.12 (m, 2H), 2.03-1.6 (m, 4H), 1.52-1.44 (m, 1H).

MS ESI: m/z=402, [M+H]$^+$.

Example 3

(1S,3R)-3-(4-amino-3-(4-phenoxyphenyl)-1H-pyrazolo[3,4-d]pyrimidin-1-yl)-1-methylcyclohexane-1-ol and (1R, 3R)-3-(4-amino-3-(4-phenoxyphenyl)-1H-pyrazolo[3,4-d]pyrimidin-1-yl)-1-methylcyclohexane-1-ol

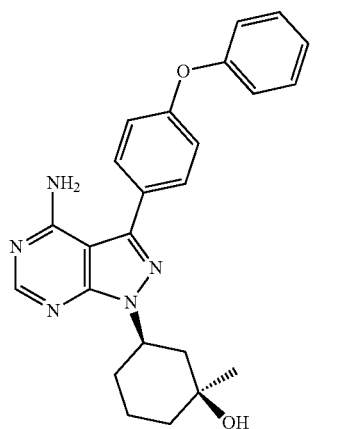

&

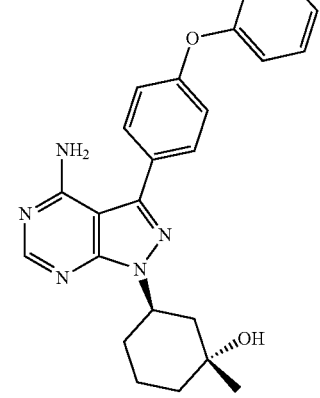

Step 1: (R)-3-(4-amino-3-(4-phenoxyphenyl)-1H-pyrazolo[3,4-d]pyrimidin-1-yl)cyclohex-1-one

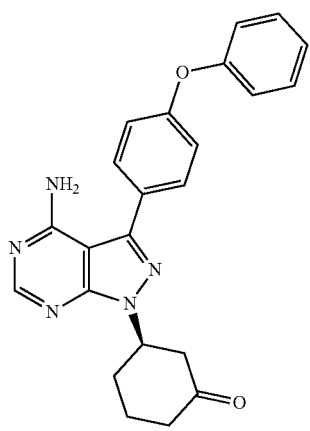 [SMILES: Nc1ncnc2c1c(-c1ccc(Oc3ccccc3)cc1)nn2[C@@H]1CCCC(=O)C1]

To a dried 25 mL flask was added (1R, 3R)-3-(4-amino-3-(4-phenoxyphenyl)-1h-pyrazole [3,4-d]pyrimidin-1-yl) cyclohex-1-ol (0.30 g, 0.68 mmol) and 5 mL ultra dry dichloromethane. The flask was placed in ice bath and Dess-Martin reagent (0.43 g, 1.02 mmol) was added. The mixture was stirred overnight and monitored with TLC. 0.5 Equivalent Dess-Martin reagent was added if the ingredient wasn't consumed. When the reaction was finished, the resulting solution was filtrated to remove white insoluble matter and mixed with silica gel. Silica gel column (DCM: MeOH=100:1) was used to purify to afford 230 mg product, yield 85%.

$^1$H NMR (400 MHz, Acetone-$d_6$): δ8.26 (s, 1H), 7.76-7.74 (m, 2H), 7.46-7.42 (m, 2H), 7.21-7.11 (m, 5H), 6.40 (brs, 2H), 5.28-5.21 (m, 1H), 3.18-3.09 (m, 1H), 2.76-2.72 (m, 1H), 2.57-2.49 (m, 1H), 2.42-2.33 (m, 2H), 2.25-2.08 (m, 2H), 1.91-1.80 (m, 1H).

MS ESI: m/z=400, [M+H]$^+$.

Step 2: (1S,3R)-3-(4-amino-3-(4-phenoxyphenyl)-1H-pyrazolo[3,4-d]pyrimidin-1-yl)-1-methylcyclohexane-1-ol and (1R, 3R)-3-(4-amino-3-(4-phenoxyphenyl)-1H-pyrazolo[3,4-d]pyrimidin-1-yl)-1-methylcyclohexane-1-ol

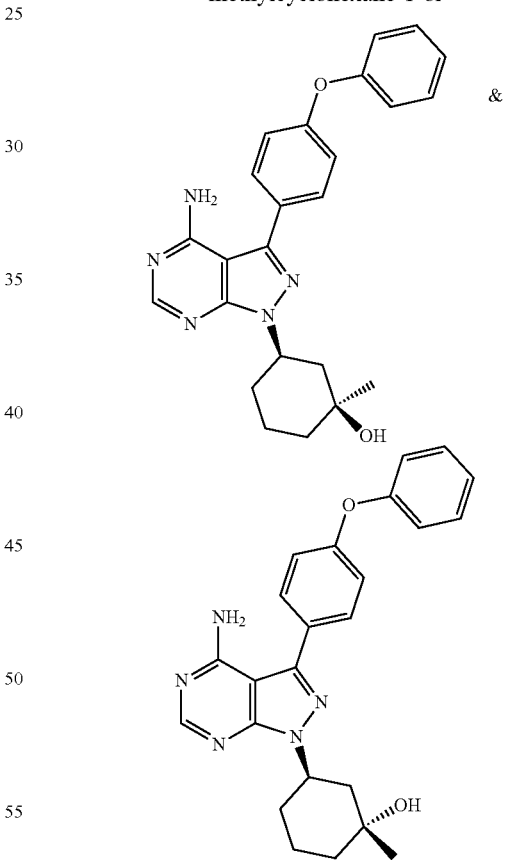

To a dried 25 mL flask was added anhydrous cerium chloride (0.35 g, 1.41 mmol) and 5 mL ultra dry THF under the protection of N$_2$. The mixture was stirred for 2 h at room temperature. The flask was placed in bath of dry ice-ethanol bath to cool to about −70° C., added slowly with 1M ether solution of methyl lithium (1.41 ml, 1.41 mmol). After reacted for 90 min at the temperature, the reaction system was added with 2 mL ultra dry THF solution of (R)-3-(4-amino-3-(4-phenoxyphenyl)-1H-pyrazolo[3,4-d]pyrimidin- 1-yl)cyclohex-1-one (0.12 g, 0.35 mmol) and then continued to react for 6 h. TLC showed that the reaction was finished. The solution was mixed with silica gel, spin-dried, and purified with silica gel column to successively afford 50 mg Example 3A: (1s, 3R)-3-(4-amino-3-(4-phenoxyphenyl)-1H-pyrazolo[3,4-d]pyrimidin-1-yl)-1-methylcyclohexane-1-ol; 50 mg Example 3B: (1R, 3R)-3-(4-amino-3-(4-phenoxyphenyl)-1H-pyrazolo[3,4-d]pyrimidin-1-yl)-1-methylcyclohexane-1-ol, total yield: 68%.

Example 3A $^1$H NMR (400 MHz, Acetone-d$_6$): δ 8.25 (s, 1H), 7.76-7.74 (m, 2H), 7.46-7.42 (m, 2H), 7.21-7.16 (m, 3H), 7.13-7.11 (m, 2H), 6.36 (brs, 2H), 4.97-4.89 (m, 1H), 3.96 (brs, 1H), 2.29-2.23 (m, 1H), 2.01-1.86 (m, 4H), 1.74-1.71 (m, 1H), 1.62-1.56 (m, 2H), 1.35 (s, 3H).

MS ESI: m/z=416.2, [M+H]$^+$.

Example 3B $^1$H NMR (400 MHz, Acetone-d$_6$): δ 8.24 (s, 1H), 7.76-7.74 (m, 2H), 7.46-7.42 (m, 2H), 7.21-7.15 (m, 3H), 7.13-7.11 (m, 2H), 6.32 (brs, 2H), 5.27-5.19 (m, 1H), 3.49 (brs, 1H), 2.18-2.12 (m, 1H), 1.98-1.91 (m, 4H), 1.72-1.69 (m, 2H), 1.49-1.41 (m, 1H), 1.29 (s, 3H).

MS ESI: m/z=416.2, [M+H]$^+$.

Example 4

3-(4-amino-3-(4-phenoxyphenyl)-1H-pyrazolo[3,4-d]pyrimidin-1-yl)-1-(trifluoromethyl)cyclohex-1-ol

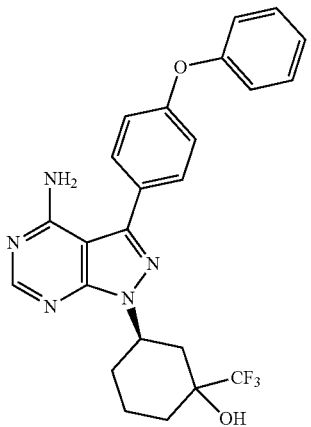 [SMILES: Nc1ncnc2c1c(-c1ccc(Oc3ccccc3)cc1)nn2[C@@H]1CCCC(O)(C(F)(F)F)C1]

To a dried 25 mL flask was added (R)-3-(4-amino-3-(4-phenoxyphenyl)-1H-pyrazolo[3,4-d]pyrimidin-1-yl)cyclohex-1-one (30 mg, 0.09 mmol), trifluoromethyltrimethylsilane (13 mg, 0.09 mmol) and 2 mL THF. The mixture was stirred at room temperature, and 3 mg cesium fluoride (13 mg, 0.09 mmol) was added. After stirred for 3 h at room temperature, 2 mL 4 N HCl was added and stirred for 2 h, then 5 mL H$_2$O was added and extracted with DCM (5 mL×2). The combined organic phase was dried with anhydrous sodium sulfate, and the mixed with silica gel. purified by silica gel column (DCM:MeOH=100:1-100:2) to afford 10 mg product, yield 21%.

$^1$H NMR (400 MHz, CDCl$_3$): δ 8.47 (s, 1H), 8.08 (brs, 1H), 7.71-7.70 (m, 2H), 7.47-7.38 (m, 2H), 7.21-7.08 (m, 5H), 5.66 (brs, 2H), 5.47 (s, 1H), 2.42-2.41 (m, 2H), 2.1-2.0 (m, 3H), 1.9-1.85 (m, 2H), 1.75-1.72 (m, 1H).

MS ESI: m/z=470.17, [M+H]$^+$.

Example 5

3-(4-amino-3-(4-phenoxyphenyl)-1H-pyrazolo[3,4-d]pyrimidin-1-yl)-1-methylcyclopentanol

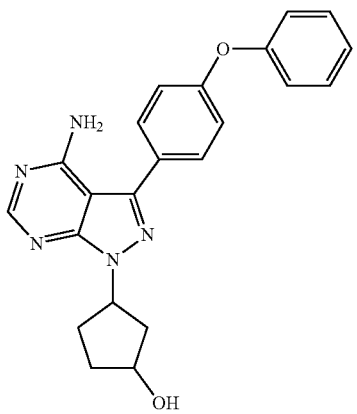 [SMILES: Nc1ncnc2c1c(-c1ccc(Oc3ccccc3)cc1)nn2C1CCC(O)C1]

3-(4-Phenoxyphenyl)-1H-pyrazolo[3,4-d]pyrimidin-4-amine (600 mg, 2.00 mmol) and 1,3-cyclopentanediol (200 mg, 2.00 mmol), and PPh$_3$ (924 mg, 3.50 mmol) were dissolved in 20 mL anhydrous THF. The mixture was stirred in ice bath and isopropyl azodicarboxylate (712 mg, 3.50 mmol) was added dropwise. After addition, the resulting solution further stirred for 1 h in ice bath, TLC showed that the raw material was consumed. The reacting solution was concentrated and purified through silica gel column (DCM: MeOH=20:1) to afford 500 mg product, yield 64%.

$^1$H NMR (400 MHz, DMSO-d$_6$): δ8.24 (s, 1H), 7.68-7.66 (m, 2H), 7.46-7.42 (m, 2H), 7.21-7.12 (m, 5H), 5.22-5.14 (m, 1H), 4.94 (d, 1H), 4.24-4.20 (m, 1H), 2.43-2.36 (m, 1H), 2.21-2.14 (m, 1H), 2.08-2.00 (m, 2H), 1.92-1.84 (m, 1H), 1.82-1.74 (m, 1H).

MS ESI: m/z=388.1, [M+H]$^+$.

Example 6

3-(4-amino-3-(4-phenoxyphenyl)-1H-pyrazolo[3,4-d]pyrimidin-1-yl)-1-methylcyclopentanol

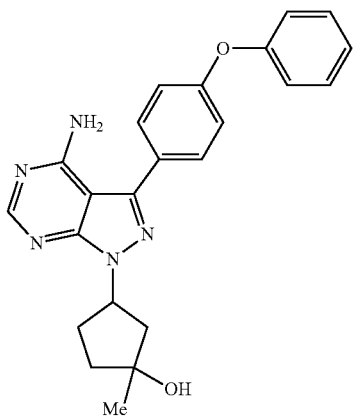 [SMILES: CC1(O)CCC(n2nc(-c3ccc(Oc4ccccc4)cc3)c3c(N)ncnc32)C1]

Step 1: 3-(4-amino-3-(4-phenoxyphenyl)-1H-pyrazolo[3,4-d]pyrimidin-1-yl)cyclopentanone

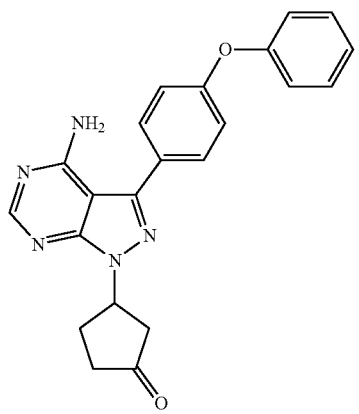 [SMILES: Nc1ncnc2c1c(-c1ccc(Oc3ccccc3)cc1)nn2C1CCC(=O)C1]

The example 5 compound was dissolved in 15 mL DCM. Dess-Martin Oxidant (548 mg, 1.29 mmol) was added into the reaction system and stirred for 2 h, then Dess-Martin Oxidant (273 mg. 0.64 mmol) was added. The reaction was monitored by TLC. After raw material was consumed, 5 mL saturated sodium bicarbonate solution was added to quench the reaction. The mixture was separated and extracted with DCM (20 mL×1). The combined organic phase was dried and filtrated. After concentration, the residue was purified with silica gel column to afford 500 mg product, yield 100%.

MS ESI: m/z=386.1, [M+H]$^+$.

Step 2: 3-(4-amino-3-(4-phenoxyphenyl)-1H-pyrazolo[3,4-d]pyrimidin-1-yl)-1-methylcyclopentanol

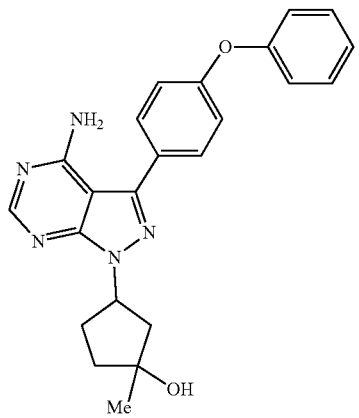 [SMILES: CC1(O)CCC(n2nc(-c3ccc(Oc4ccccc4)cc3)c3c(N)ncnc32)C1]

To a dried 25 mL two-necked-flask was added anhydrous cerium chloride (153 mg, 0.62 mmol) and 10 mL ultra dry THF. The mixture was stirred for 1 h at room temperature. The reaction system was placed in dry ice-ethanol bath to cool to −75° C. and then ethyl ether solution of methyl lithium (1.33 m, 0.48 ml, 0.62 mmol) was added dropwise. The resulting solution was further stirred for 1 h before the dropwise addition of 3-(4-amino-3-(4-phenoxyphenyl)-1H-pyrazolo[3,4-d]pyrimidin-1-yl)cyclopentanone in THF (40 mg, 0.1 mmol/0.5 ml THF). After addition, the reacting solution was further reacted for 1.5 h, and TLC showed that new ingredient was generated. 10 mL saturated ammonium chloride was added to quench the reaction, and extracted with ethyl acetate (20 mL×1). The organic phase was dried with anhydrous sodium sulfate and filtrated. After concentration, the residue was purified with silica gel column to afford 6 mg product, yield 15%.

$^1$H NMR (400 MHz, CDCl$_3$): δ 8.36 (s, 1H), 7.65 (m, 2H), 7.41-7.37 (m, 2H), 7.19-7.14 (m, 3H), 7.08 (m, 2H), 5.71-5.63 (m, 1H), 5.60 (brs, 2H), 2.52-2.45 (m, 1H), 2.42-2.37 (m, 1H), 2.28-2.11 (m, 4H), 1.52 (s, 3H).

MS ESI: m/z=402.1, [M+H]$^+$.

Example 7

3-(4-amino-3-(4-phenoxyphenyl)-1H-pyrazolo[3,4-d]pyrimidin-1-yl)-1-(trifluoromethyl) Cyclopentanol To a flask was added 3-(4-amino-3-(4-phenoxyphenyl)-1H-pyrazolo[3,4-d]pyrimidin-1-yl) cyclopentanone (39 mg, 0.10 mmol), cesium fluoride (0.15 mg), trifluoromethyltrimethylsilane (15 mg, 0.10 mmol) and 1 mL ultra dry THF. The colorless solution turned to orange, and was stirred for 3 h at room temperature. The mixture was added with 4 N hydrochloric acid aqueous solution (0.06 ml) and continued to stir for 2 h. TLC and LCMS jointly showed that the reaction was completed. The reacting solution was quenched with 2 mL H$_2$O and extracted with EtOAc (ethyl acetate) (5 mL×3). The combined organic phase was dried with anhydrous sodium sulfate and filtrated. After concentration, the residue was purified with silica gel column to afford 10 mg product, yield 22%.

$^1$H NMR (400 MHz, CDCl$_3$): δ 8.36 (s, 1H), 7.63 (m, 2H), 7.42-7.37 (m, 2H), 7.20-7.17 (m, 1H), 7.16-7.13 (m, 2H), 7.10-7.07 (m, 2H), 5.70 (brs, 2H), 5.55-5.50 (m, 1H), 2.76-2.69 (m, 1H), 2.56-2.49 (m, 1H), 2.40 (m, 1H), 2.36-2.30 (m, 1H), 2.15-2.11 (m, 2H).

MS ESI: m/z=456.1, [M+H]$^+$.

Example 8

(1s,4S)-4-(4-amino-3-(4-phenoxyphenyl)-1H-pyrazolo[3,4-d]pyrimidin-1-yl)cyclohexane-1-ol and (1R,4R)-4-(4-amino-3-(4-phenoxyphenyl)-1H-pyrazolo[3,4-d]pyrimidin-1-yl)cyclohexane-1-ol

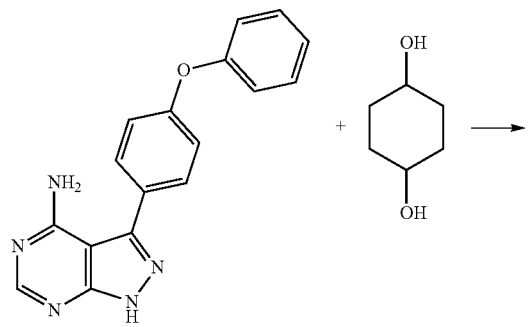

To a dried 50 mL two-necked-flask was added PPh₃ (0.52 g, 1.98 mmol) and 15 mL ultra dry THF, and cooled in icy ethanol bath. Then diisopropyl azodicarboxylate (0.40 g, 0.39 ml, 1.98 mmol) was added dropwise into the system. The reacting solution was stirred for 30 min under same temperature until the reaction system turned into white precipitate. 3-(4-phenoxyphenyl)-1H-pyrazolo[3,4-d]pyrimidin-4-amine (0.30 g, 0.99 mmol) and 1,4-cyclohexanediol (cis:trans=1:0.7, NMR) (114 mg, 0.99 mmol) in 10 mL THF were added into the resulting solution to react for 30 min, and TLC showed that 1,4-cyclohexanediol was consumed. 20 mL Saturated ammonium chloride was added into the solution. Most THF was removed and extracted with DCM (20 mL×3). The combined organic phase was washed with brine (50 mL×1) and dried with anhydrous sodium sulfate. Silica gel was added after filtration. The mixture was purified with silica gel column (MeOH/DCM) to afford 10 mg example 8A (1s, 4S)-4-(4-amino-3-(4-phenoxyphenyl)-1H-pyrazolo[3,4-d]pyrimidin-1-yl) cyclohexane-1-ol, yield 22% (1% MeOH) and 30 mg example 8B(1R, 4R)-4-(4-amino-3-(4-phenoxyphenyl)-1H-pyrazolo[3,4-d]pyrimidin-1-yl) cyclohexane-1-ol, yield 10% (2% MeOH).

Example 8A $^1$H NMR (400 MHz, CDCl₃): δ 8.38 (s, 1H), 7.67-7.63 (m, 2H), 7.40-7.39 (m, 2H), 7.19-7.07 (m, 5H), 5.46 (brs, 2H), 4.84-4.76 (m, 1H), 3.86-3.79 (m, 1H), 2.28-2.05 (m, 6H), 1.57-1.56 (m, 2H).

MS ESI: m/z=402, [M+H]⁺.

Example 8B $^1$H NMR (400 MHz, CDCl₃): δ 8.43 (s, 1H), 7.48-7.41 (m, 2H), 7.40-7.39 (m, 2H), 7.28-7.27 (m, 1H), 7.24-7.16 (m, 4H), 5.24 (brs, 2H), 4.22-4.16 (m, 1H), 3.91-3.86 (m, 1H), 2.45-2.35 (m, 2H), 2.14-2.11 (m, 2H), 1.95-1.92 (m, 2H), 1.40-1.31 (m, 2H).

MS ESI: m/z=402, [M+H]⁺.

Example 9

(1s,4S)-4-(4-amino-3-(4-phenoxyphenyl)-1H-pyrazolo[3,4-d]pyrimidin-1-yl]-1-methylcyclohexane-1-ol and (1R,4R)-4-(4-amino-3-(4-phenoxyphenyl)-1H-pyrazolo[3,4-d]pyrimidin-1-yl]-1-methylcyclohexane-1-ol

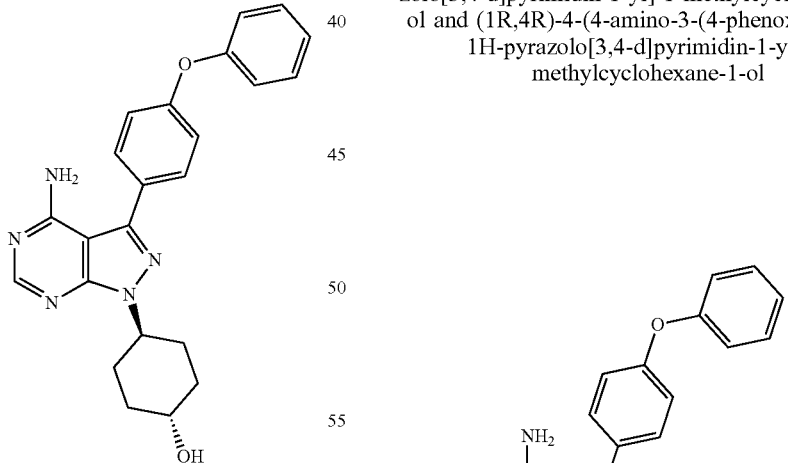

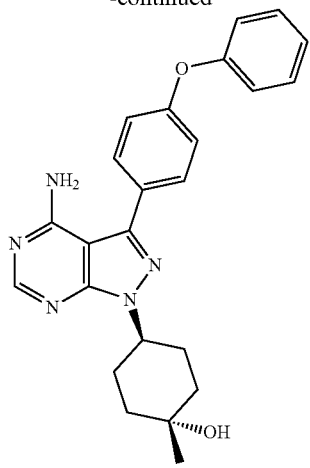

Step 1: 4-(4-amino-3-(4-phenoxyphenyl)-1H-pyrazolo[3,4-d]pyrimidin-1-yl]cyclohexanone-1-one

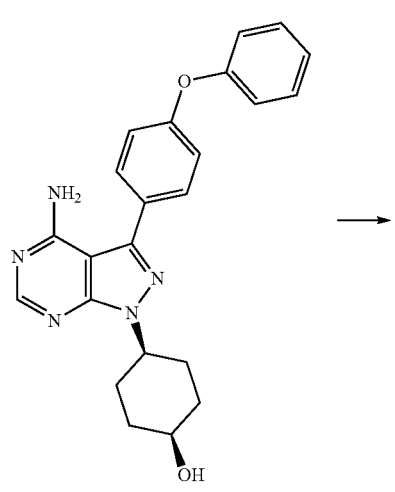

To a dried 25 mL flask was added (1s, 4S)-4-(4-amino-3-(4-phenoxyphenyl)-1H-pyrazolo[3,4-d]pyrimidin-1-yl) cyclohexane-1-ol (0.20 g, 0.45 mmol) and 3 mL anhydrous DCM under Ar. The flask was placed in ice-ethanol bath. 3 mL Dess-Martin reagent (0.23 g, 0.53 mmol) in DCM was added dropwise into the flask under stirring and further stirred for another 5 h after that. TLC showed that the reaction was completed. Moderate silica gel was added into the reaction system. The mixture was purified with silica gel column (DCM:MeOH=100:1) to afford 150 mg product, yield 83%.

Step 2: (1S,4S)-4-(4-amino-3-(4-phenoxyphenyl)-1H-pyrazolo[3,4-d]pyrimidin-1-yl]-1-methylcyclohexane-1-ol and (1R,4R)-4-(4-amino-3-(4-phenoxyphenyl)-1H-pyrazolo[3,4-d]pyrimidin-1-yl]-1-methylcyclohexane-1-ol

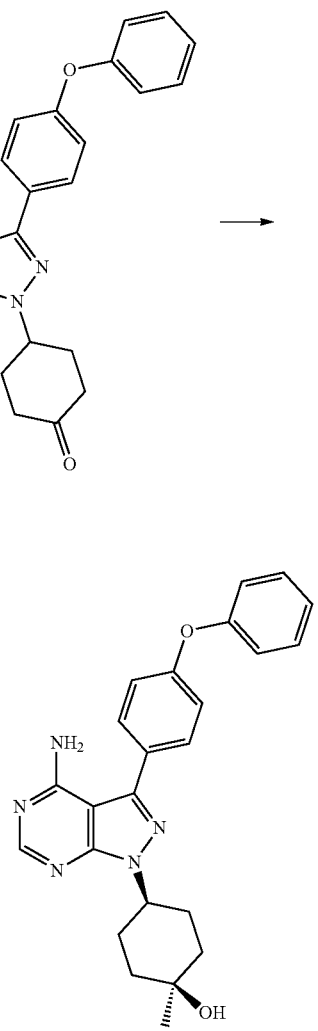

-continued

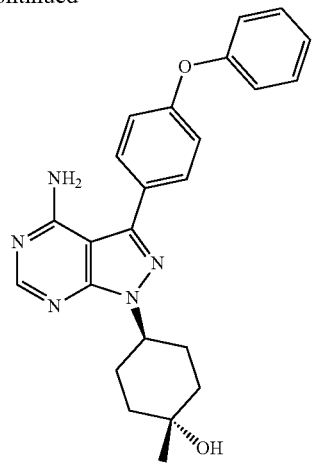

To a dried 25 mL flask was added anhydrous cerium chloride (0.29 g, 1.18 mmol) and 2 mL anhydrous THF under the protection of Ar. The mixture was stirred for 1 h at room temperature, then placed in dry ice-ethanol bath to cool to about −75° C. The resulting solution was mixed slowly with 1M of methyl lithium (1.18 mL, 1.18 mmol) in ether. After reacted for 2 h at −75° C., the reaction system was mixed with 5 mL THF solution of 4-(4-amino-3-(4-phenoxyphenyl)-1H-pyrazolo[3,4-d]pyrimidin-1-yl]cyclohexanone-1-one (100 mg, 0.30 mmol) and continued to react for 15 min. The dry ice-ethanol bath was removed, and mixture was continued to react for 1 h (naturally warmed to room temperature). TLC showed that the reaction was finished. The reacting solution was mixed with 15 mL 0.5N HCl aqueous solution and extracted with DCM (10 mL×3). The combined organic phase was washed with saturated sodium bicarbonate (10 mL×2), H₂O (20 mL×2) and brine (20 mL×1) and then dried with anhydrous sodium sulfate. After filtered and concentrated, the residue was purified with silica gel column (DCM:MeOH=100:1~100:2) to afford 50 mg Example 9A: (1s,4s)-4-(4-amino-3-(4-phenoxyphenyl)-1H-pyrazolo[3,4-d]pyrimidin-1-yl]-1-methylcyclohexane-1-ol, yield 42%; 50 mg Example 9B: (1r,4r)-4 (4-amino-3-(4-phenoxyphenyl)-1H-pyrazolo[3,4-d]pyrimidin-1-yl]-1-methylcyclohexane-1-ol, yield: 42%.

Example 9A $^{1}$H NMR (400 MHz, CDCl$_{3}$): δ 8.37 (s, 1H), 7.66 (d, J=8.6 Hz, 2H), 7.39 (t, J=8.0 Hz, 2H), 7.16 (dd, J=12.2 Hz, 8.0 Hz, 3H), 7.08 (d, J=7.7 Hz, 2H), 5.49 (brs, 2H), 4.79-4.72 (m, 1H), 2.55-2.45 (m, 2H), 1.94-1.79 (m, 4H), 1.75-1.67 (m, 2H), 1.32 (s, 3H).

MS ESI: m/z=416, [M+H]$^{+}$.

Example 9B $^{1}$H NMR (400 MHz, CDCl$_{3}$): δ 8.37 (s, 1H), 7.65 (d, J=8.7 Hz, 2H), 7.39 (dd, J=8.5, 7.5 Hz, 2H), 7.21-7.12 (m, 3H), 7.08 (dd, J=8.6, 1.0 Hz, 2H), 5.53 (s, 2H), 4.91-4.76 (m, 1H), 2.33-2.18 (m, 2H), 2.09-2.01 (m, 2H), 1.92 (d, J=12.8 Hz, 2H), 1.77 (dd, J=13.1, 3.8 Hz, 2H), 1.43 (s, 3H).

MS ESI: m/z=416, [M+H]$^{+}$.

Example 10

4-(4-amino-3-(4-phenoxyphenyl)-1H-pyrazolo[3,4-d]pyrimidin-1-yl]-1-cyclopropylcyclohexane-1-ol

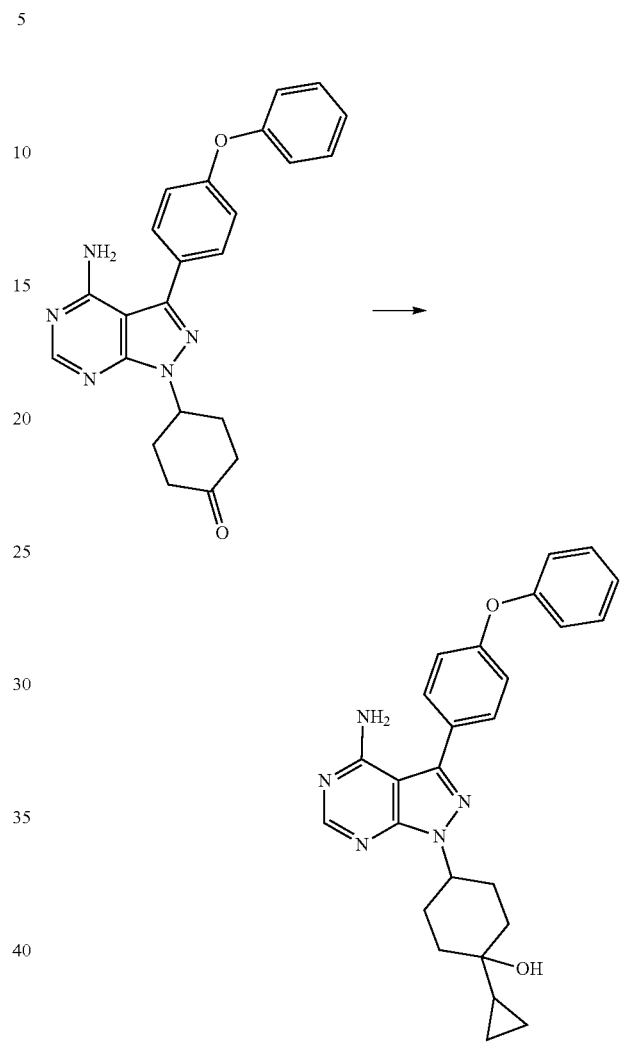

To a dried 50 mL two-necked-flask was added intermediate 4-(4-amino-3-(4-phenoxyphenyl)-1H-pyrazolo[3,4-d]pyrimidin-1-yl]cyclohex-1-one (0.30 g, 0.75 mmol) and 30 mL anhydrous THF under Ar. The reaction flask was placed in ice-ethanol bath to cool to about −10° C. Then 1M cyclopropyl magnesium bromide (7.51 ml, 7.51 mmol) in THF was added dropwise into the system. After addition, the ice-ethanol bath was removed to naturally warm to room temperature. The resulting solution was continued to react overnight. TLC showed that the reaction was completed. 10 mL 0.5N HCl aqueous solution was added to the solution and extracted with DCM (10 mL×3). The combined organic phase and washed with saturated sodium bicarbonate (10 mL×3), H₂O (10 mL×3) and brine (20 mL×1) and then dried with anhydrous sodium sulfate. After filtration and concentration, the residue was purified with silica gel column (DCM:MeOH=100:1~100:2) to afford 250 mg product, yield 65%.

$^{1}$H NMR (400 MHz, CDCl$_{3}$): δ 8.35 (s, 1H), 7.65 (m, 2H), 7.45-7.32 (m, 2H), 7.19-7.04 (m, 5H), 5.70 (brs, 2H), 4.98-4.84 (m, 0.3H), 4.77 (m, 0.7H), 2.67-2.44 (m, 1.6H), 2.44-2.32 (m, 0.75H), 2.18-1.53 (m, 6H), 1.06-0.84 (m, 1H), 0.40 (d, J=6.9 Hz, 4H).

MS ESI: m/z=442, [M+H]$^{+}$.

Example 11

(1s,4S)-4-(4-amino-3-(4-(4-fluorophenoxy)phenyl)-1H-pyrazolo[3,4-d]pyrimidin-1-yl)cyclohex-1-ol and (1R,4R)-4-(4-amino-3-(4-(4-fluorophenoxy)phenyl)-1H-pyrazolo[3,4-d]pyrimidin-1-yl) cyclohex-1-ol

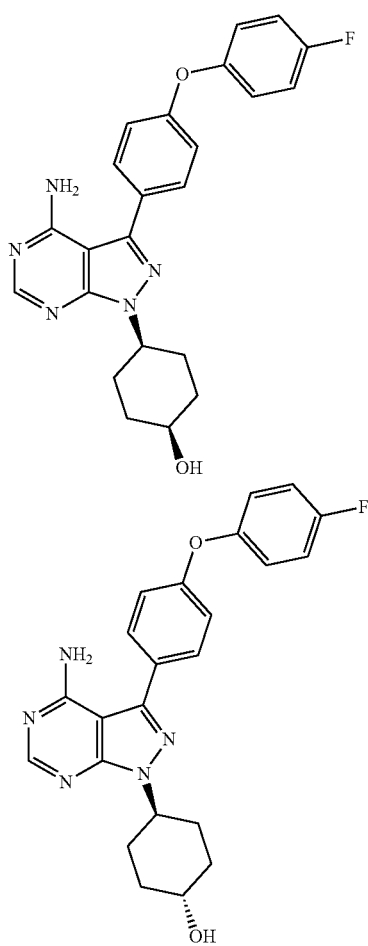

Step 1: 1-bromo-4-(4-fluorophenoxy) benzene

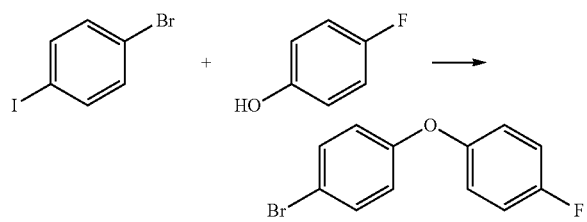

To a dried 500 mL three-necked-flask bromoiodobenzene (30.00 g, 106.04 mmol), 4-fluorophenol (17.83 g, 159.06 mmol), cesium carbonate (69.10 g, 212.08 mmol), dimethylaminoacetic acid (0.82 g, 7.95 mmol), cuprous iodide (0.40 g, 2.12 mmol) and 350 mL 1,4-dioxane were added successively under Ar. The mixture was warmed to 90° C. to react for 8 h, and TLC showed that the reaction was completed. 200 mL $H_2O$ was added to the solution, separated and extracted with EtOAc (50 mL×3). The combined organic phase was washed with saturated brine (300 mL×1) and dried with anhydrous sodium sulfate. After filtration, the resulting solution was mixed with silica gel and purified with silica gel column (petroleum ether) to afford 21.00 g product, yield 73%.

$^1$H NMR (400 MHz, $CDCl_3$): δ 7.42 (d, J=9.0 Hz, 2H), 7.08-7.00 (m, 2H), 7.00-6.93 (m, 2H), 6.84 (d, J=9.0 Hz, 2H).

Step 2: (4-(4-fluorophenoxy)phenyl)boric Acid

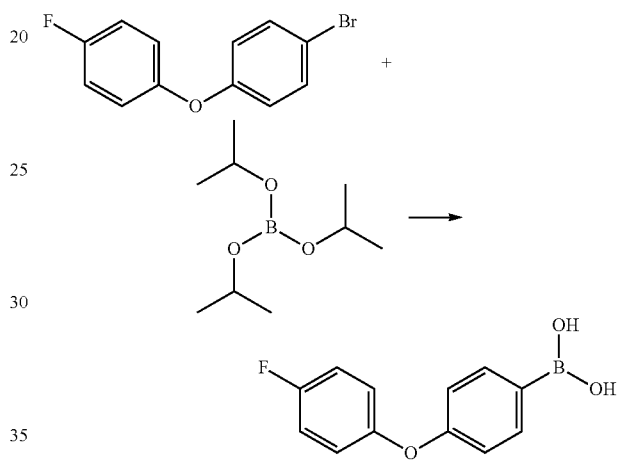

To a dried 250 mL two-necked-flask was added intermediate 1-bromo-4-(4 fluorophenoxy)benzene (2.00 g, 7.49 mmol) and 100 mL anhydrous THF, and cooled in dry ice-ethanol bath. The reaction system was mixed slowly with 2.4M n-butyl lithium in n-hexane (4.06 ml, 9.73 mmol) and continued to stir for 40 min. Triisopropoxyboron was added dropwise into the system. TLC showed that the reaction was completed. The reacting solution was slowly poured into 100 mL saturated ammonium chloride solution and extracted with EtOAc (50 mL×3). The combined organic phase and washed with saturated brine (100 mL×1) and dried with anhydrous sodium sulfate. After filtration and concentration, the residue was purified with silica gel column (petroleum ether:ethyl acetate=97:3~55:45) to afford 1.5 g product, yield 86%.

$^1$H NMR (400 MHz, $CDCl_3$): δ 8.16 (d, J=8.6 Hz, 2H), 7.10-6.94 (m, 8H).

Step 3: 3-(4-(4-fluorophenoxy)phenyl)-1H-pyrazolo[3,4-d]pyrimidin-4-amine

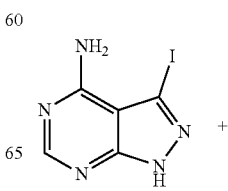

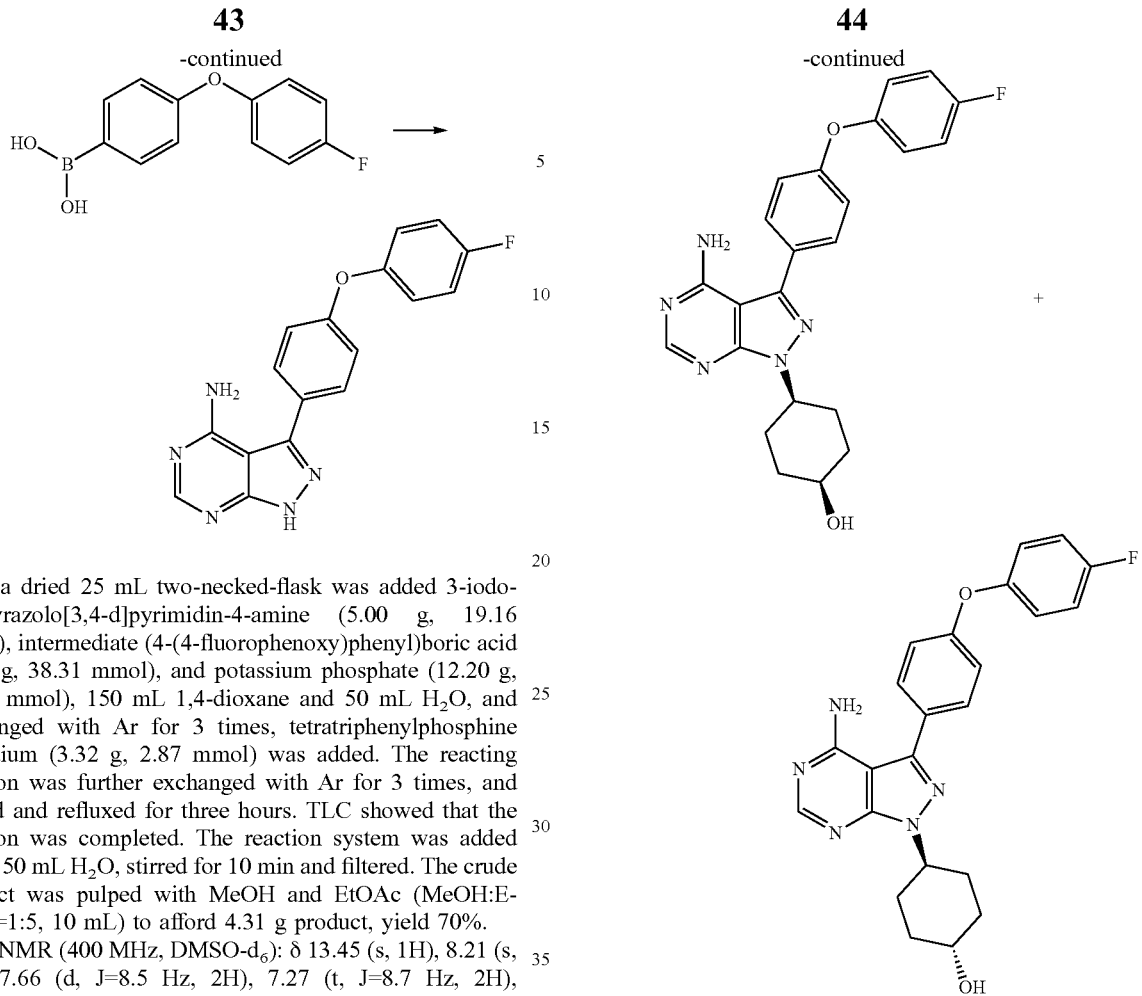

To a dried 25 mL two-necked-flask was added 3-iodo-1H-pyrazolo[3,4-d]pyrimidin-4-amine (5.00 g, 19.16 mmol), intermediate (4-(4-fluorophenoxy)phenyl)boric acid (8.89 g, 38.31 mmol), and potassium phosphate (12.20 g, 57.47 mmol), 150 mL 1,4-dioxane and 50 mL H₂O, and exchanged with Ar for 3 times, tetratriphenylphosphine palladium (3.32 g, 2.87 mmol) was added. The reacting solution was further exchanged with Ar for 3 times, and heated and refluxed for three hours. TLC showed that the reaction was completed. The reaction system was added with 150 mL H₂O, stirred for 10 min and filtered. The crude product was pulped with MeOH and EtOAc (MeOH:EtOAc=1:5, 10 mL) to afford 4.31 g product, yield 70%.

$^1$H NMR (400 MHz, DMSO-$d_6$): δ 13.45 (s, 1H), 8.21 (s, 1H), 7.66 (d, J=8.5 Hz, 2H), 7.27 (t, J=8.7 Hz, 2H), 7.21-7.16 (m, 2H), 7.13 (d, J=8.5 Hz, 2H), 6.74 (brs, 2H). MS ESI: m/z=322, [M+H]$^+$.

Step 4: (1S, 4S)-4-(4-amino-3-(4-(4-fluorophenoxy)phenyl)-1H-pyrazolo[3,4-d]pyrimidin-1-yl)cyclohex-1-ol and (1R,4R)-4-(4-amino-3-(4-(4-fluorophenoxy)phenyl)-1H-pyrazolo[3,4-d]pyrimidin-1-yl)cyclohex-1-ol

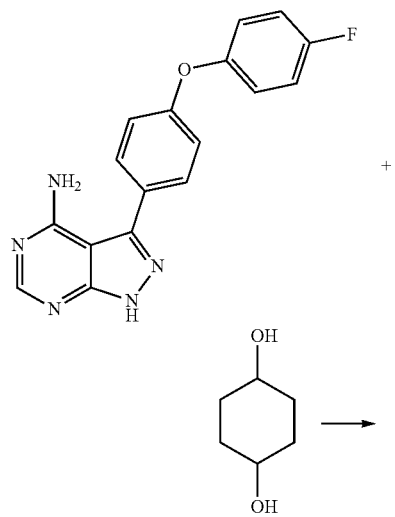

To a dried 100 mL two-necked-flask was added intermediate 3-(4-(4-fluorophenoxy)phenyl)-1H-pyrazolo[3,4-d]pyrimidin-4-amine (1.00 g, 3.11 mmol), 1,4-cyclohexanediol (cis:trans=1:0.7, NMR content) (0.72 g, 6.22 mmol), PPh₃ (1.63 g, 6.22 mmol) and 40 mL anhydrous THF, and cooled in icy ethanol bath. Diisopropyl azodicarboxylate (1.26 g, 6.22 mmol) was added slowly into the mixture and stirred overnight. TLC and LCMS showed that the reaction was completed. The reacting solution was added with 20 mL saturated ammonium chloride solution to remove most of THF. The resulting solution was added with 20 mL H₂O and extracted with DCM (30 mL×3). The combined organic phase was washed with brine (50 mL×1), and dried with anhydrous sodium sulfate. After filtration, the reaction system was mixed with silica gel, and purified on silica gel column to afford 700 mg example 11A (1s,4s)-4-(4-amino-3-(4-(4-fluorophenoxy)phenyl)-1H-pyrazolo[3,4-d]pyrimidin-1-yl)cyclohex-1-ol, yield 53%; and 100 mg example 11B (1r,4r)-4-(4-amino-3-(4-(4-fluorophenoxy)phenyl)-1H-pyrazolo[3,4-d]pyrimidin-1-yl)cyclohex-1-ol 100 mg, yield 8%.

Example 11A $^1$H NMR (400 MHz, CDCl₃): δ 8.34 (s, 1H), 7.66 (d, J=8.7 Hz, 2H), 7.10-7.06 (m, 6H), 5.90 (brs, 2H), 4.83-4.78 (m, 1H), 4.12 (m, 1H), 2.55-2.49 (m, 2H), 2.01 (m, 2H), 2.42-2.41 (m, 2H), 2.04-1.99 (m, 2H).
MS ESI: m/z=420, [M+H]$^+$.

Example 11B $^1$H NMR (400 MHz, CDCl$_3$): δ 8.38 (s, 1H), 7.64 (d, J=8.7 Hz, 2H), 7.12-7.05 (m, 6H), 5.45 (brs, 2H), 4.82-4.76 (m, 1H), 3.86-3.75 (m, 2H), 2.27-2.05 (m, 7H).

MS ESI: m/z=420, [M+H]$^+$.

Example 12

(1s,4S)-4-(4-amino-3-(4-(4-fluorophenoxy)phenyl)-1H-pyrazolo[3,4-d]pyrimidin-1-yl)-1-methylcyclohex-1-ol and (1R,4R)-4-(4-amino-3-(4-(4-fluorophenoxy)phenyl)-1H-pyrazolo 3,4-d]pyrimidin-1-yl)-1-methylcyclohex-1-ol

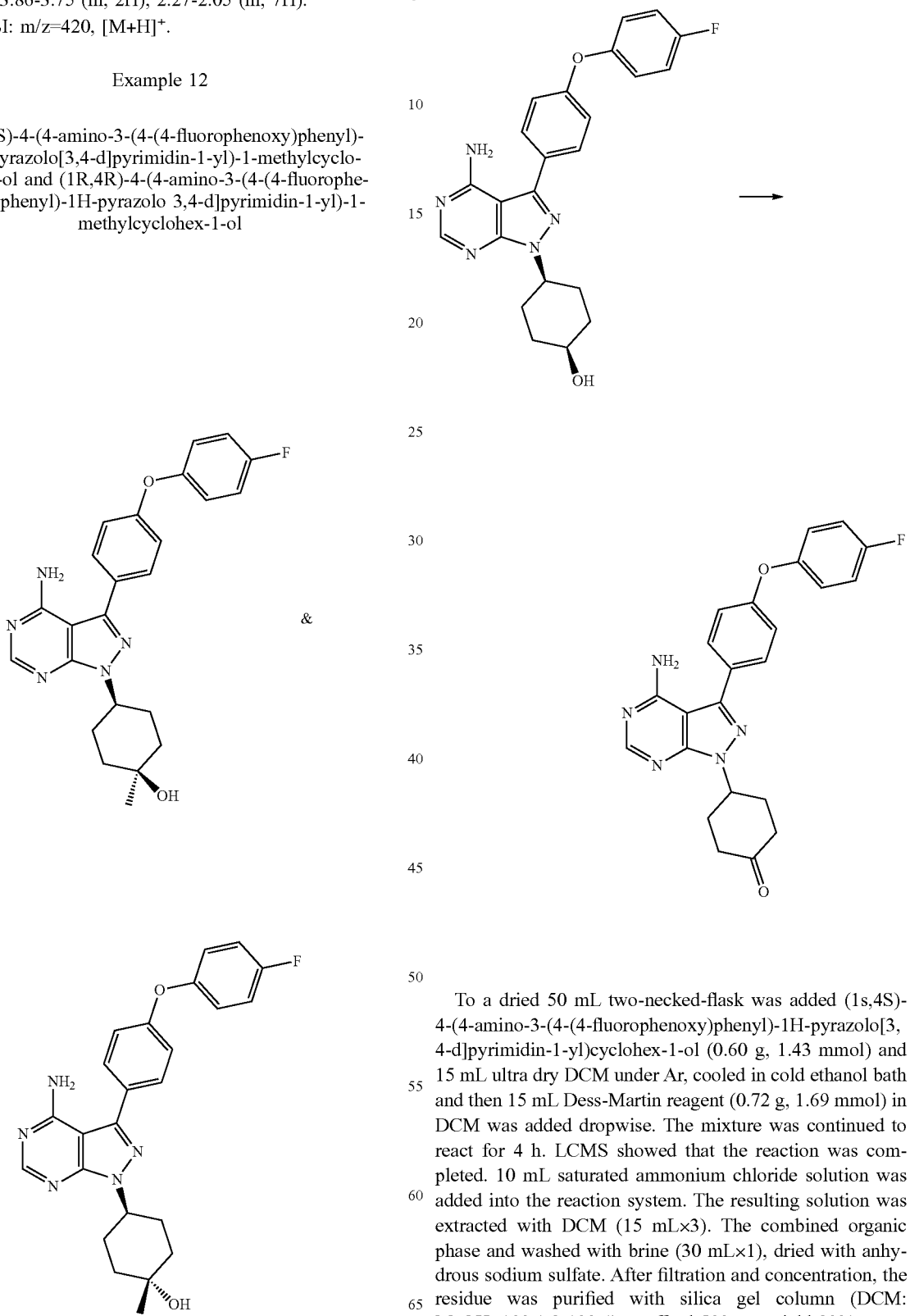

Step 1: 4-(4-amino-3-(4-fluorophenoxy)phenyl)-1H-pyrazolo[3,4-d]pyrimidin-1-yl)cyclohex-1-one To a dried 50 mL two-necked-flask was added (1s,4S)-4-(4-amino-3-(4-(4-fluorophenoxy)phenyl)-1H-pyrazolo[3,4-d]pyrimidin-1-yl)cyclohex-1-ol (0.60 g, 1.43 mmol) and 15 mL ultra dry DCM under Ar, cooled in cold ethanol bath and then 15 mL Dess-Martin reagent (0.72 g, 1.69 mmol) in DCM was added dropwise. The mixture was continued to react for 4 h. LCMS showed that the reaction was completed. 10 mL saturated ammonium chloride solution was added into the reaction system. The resulting solution was extracted with DCM (15 mL×3). The combined organic phase and washed with brine (30 mL×1), dried with anhydrous sodium sulfate. After filtration and concentration, the residue was purified with silica gel column (DCM:MeOH=100:1.2-100:4) to afford 500 mg, yield 83%.

MS ESI: m/z=418, [M+H]$^+$.

Step 2: (1s,4s)-4-(4-amino-3-(4-(4-fluorophenoxy) phenyl)-1H-pyrazolo[3,4-d]pyrimidin-1-yl)-1-methylcyclohex-1-ol and (1R, 4R)-4-(4-amino-3-(4-(4-fluorophenoxy) phenyl)-1H-pyrazolo[3,4-d]pyrimidin-1-yl)-1-methylcyclohex-1-ol

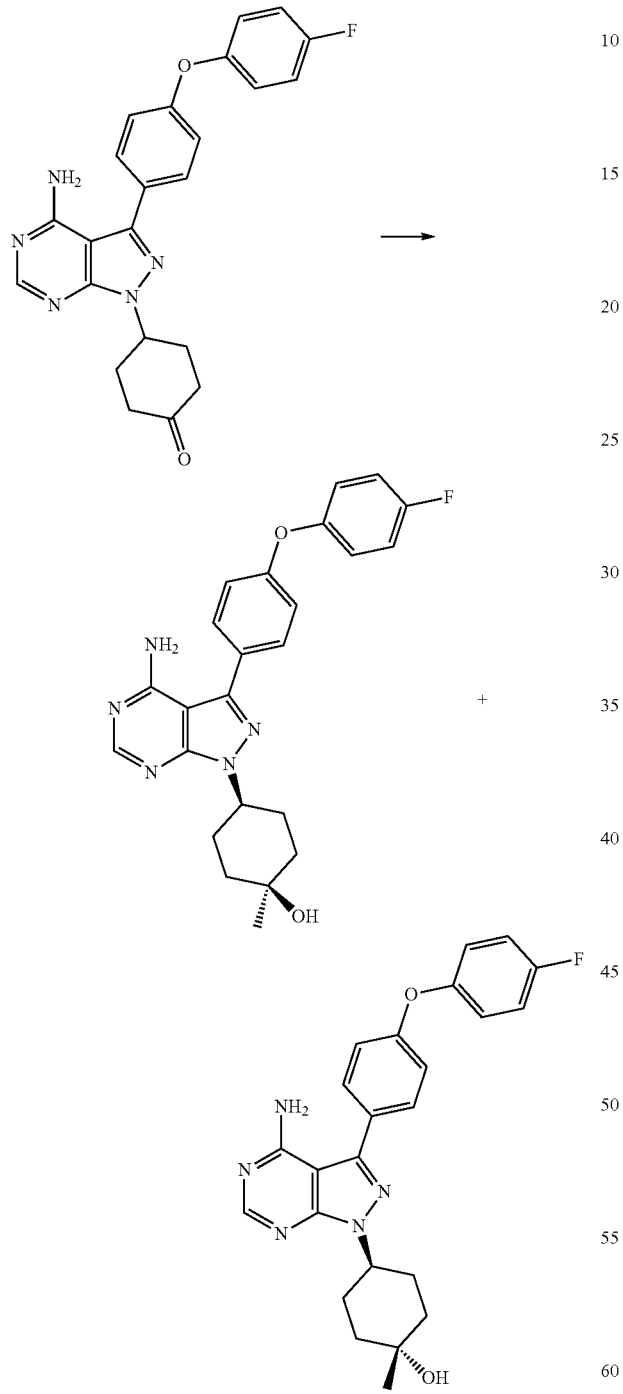

To a dried 25 mL two-necked-flask was added anhydrous cerium chloride (0.29 g, 1.18 mmol) and 3 mL anhydrous THF under Ar. The mixture was stirred for 1 h at room temperature, and placed in dry ice-ethanol bath to cool to about −70° C. 1.6M Ether solution of methyl lithium (1.18 mL, 1.18 mmol) was added dropwise, and the resulting solution was stirred at the temperature for 1 h. 3 mL of 4-(4-amino-3-(4-(4-fluorophenoxy) phenyl)-1H-pyrazolo[3,4-d]pyrimidin-1-yl)cyclohex-1-one (0.10 g, 0.24 mmol) in THF was added dropwise into the solution, and then continued to stir for 1.5 h. TLC showed that the reaction was finished. The reaction was quenched by 3 mL saturated ammonium chloride solution, THF was removed, and then extracted with EtOAc (5 mL×3). The combined organic phase was washed with brine (5 mL×2) and then dried with anhydrous sodium sulfate. After filtration, silica gel was added. The residue was purified with silica gel column (DCM:MeOH=100:1.2~100:5~100:10) to afford 25 mg Example 12A: (1s, 4s)-4-(4-amino-3-(4-(4-fluorophenoxy) phenyl)-1H-pyrazolo[3,4-d]pyrimidin-1-yl)-1-methylcyclohex-1-ol, yield 25%; 23 mg Example 12B: (1r, 4r)-4-(4-amino-3-(4-(4-fluorophenoxy) phenyl)-1H-pyrazolo[3,4-d]pyrimidin-1-yl)-1-methylcyclohex-1-ol, yield: 23%.

Example 12A $^1$H NMR (400 MHz, CDCl$_3$): δ 8.34 (s, 1H), 7.66-7.64 (d, 2H), 7.12-7.05 (m, 6H), 5.73 (brs, 2H), 4.79-4.71 (m, 1H), 2.54-2.44 (m, 2H), 1.91-1.84 (m, 4H), 1.72-1.66 (m, 2H), 1.32 (s, 3H).

MS ESI: m/z=434, [M+H]$^+$.

Example 12B $^1$H NMR (400 MHz, CDCl$_3$): δ 8.37 (s, 1H), 7.66-7.64 (d, 2H), 7.13-7.06 (m, 6H), 5.58 (brs, 2H), 4.88-4.80 (m, 1H), 2.30-2.20 (m, 2H), 2.07-2.03 (m, 2H), 1.93-1.90 (m, 2H), 1.79-1.72 (m, 2H), 1.43 (s, 3H).

MS ESI: m/z=434, [M+H]$^+$.

Example 13

(±) Cis-3-(4-amino-3-(4-(4-fluorophenoxy)phenyl)-1H-pyrazolo[3,4-d]pyrimidin-1-yl) cyclopentane-1-ol and (±) Trans-3-(4-amino-3-(4-(4-fluorophenoxy) phenyl)-1H-pyrazolo[3,4-d]pyrimidin-1-yl) cyclopentane-1-ol

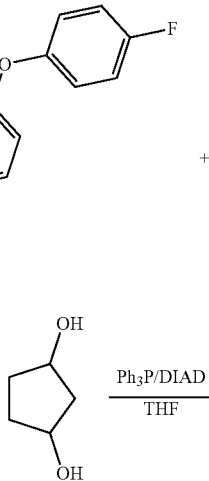

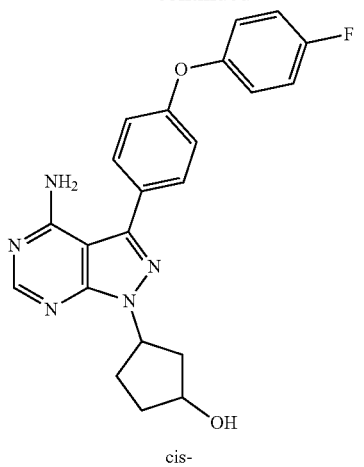

cis-

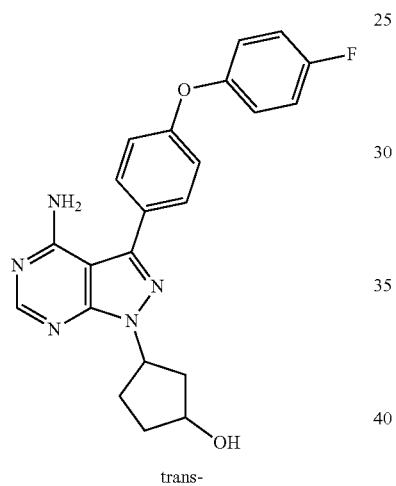

trans-

To a dried 100 mL three-necked-flask was added the intermediates 3-(4-(4-fluorophenoxy) phenyl)-1H-pyrazolo[3,4-d]pyrimidin-4-amine (3.10 g, 9.65 mmol) and PPh₃ (2.56 g, 9.74 mmol) under Ar, and exchanged with Ar for 3 times and then placed in ice-ethanol bath. 10 mL of 1,3-cyclopentanediol (0.99 g, 9.65 mmol) in ultra dry THF was added, and then diisopropyl azodicarboxylate (0.99 g, 9.65 mmol) was slowly added dropwise into the reaction system. The resulting solution was reacted for 3 h, and LCMS showed that the reaction was finished. The solution was poured into 130 mL H₂O and then extracted with EtOAc (100 mL×3). The combined organic phase and washed with brine (200 mL×1) and then dried with anhydrous sodium sulfate. After filtration and concentration, the residue was purified with silica gel column to afford 1.8 g Example 13A: (±) cis-3-(4-amino-3-(4-(4-fluorophenoxy)phenyl)-1H-pyrazolo[3,4-d]pyrimidin-1-yl) cyclopentane-1-ol, yield 46%; 200 mg Example 13B: (±) trans-3-(4-amino-3-(4-(4-fluorophenoxy)phenyl)-1H-pyrazolo[3,4-d]pyrimidin-1-yl) cyclopentane-1-ol, yield: 5%.

Example 13A $^{1}$H NMR (400 MHz, CDCl₃): δ 8.38 (s, 1H), 7.63 (m, 2H), 7.15-6.97 (m, 6H), 5.56 (brs, 2H), 5.47 (m, 1H), 4.44 (s, 1H), 2.52-2.34 (m, 2H), 2.32-2.16 (m, 1H), 2.20 (m, 1H), 2.12-2.00 (m, 1H), 1.92-1.81 (m, 1H).

MS ESI: m/z=406, [M+H]⁺.

Example 13B

MS ESI: m/z=406, [M+H]⁺.

Example 14

(±) cis-3-(4-amino-3-(4-(4-fluorophenoxy)phenyl)-1H-pyrazolo[3,4-d]pyrimidin-1-yl)-1-methylcyclopentan-1-ol and (±) trans-3-(4-amino-3-(4-(4-fluorophenoxy)phenyl)-1H-pyrazolo[3,4-d]pyrimidin-1-yl)-1-methylcyclopentan-1-ol

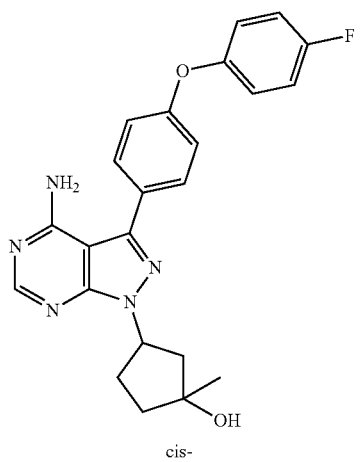

cis-

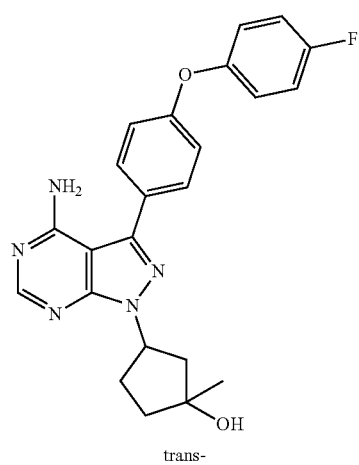

trans-

Step 1: 3-(4-amino-3-(4-(4-fluorophenoxy)phenyl)-1H-pyrazolo[3,4-d]pyrimidin-1-yl)cyclopentane-1-one

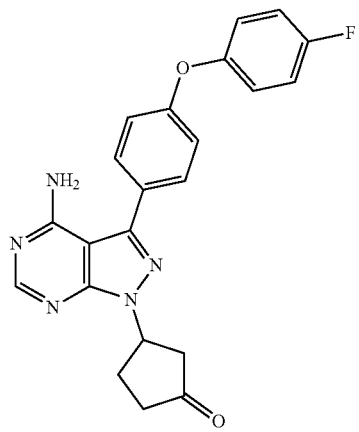 [SMILES: Nc1ncnc2c1c(-c1ccc(Oc3ccc(F)cc3)cc1)nn2C1CCC(=O)C1]

To a dried 50 mL two-necked-flask was added (±) cis-3-(4-amino-3-(4-(4-fluorophenoxy)phenyl)-1H-pyrazolo[3,4-d]pyrimidin-1-yl)cyclopentane-1-ol (0.50 g, 1.23 mmol) and 15 mL of ultra dry DCM under Ar. The flask was cooled in ice ethanol bath. 15 ml DCM solution of Dess-Martin reagent (0.62 g, 1.46 mmol) was added dropwise into the mixture. The resulting solution continued to react, and Monitored by LCMS. After the starting material was consumed, the system was added with 10 mL saturated ammonium chloride and then extracted with DCM (15 mL×3). The combined organic phase and washed with brine (30 mL×1) and then dried with anhydrous sodium sulfate. After filtration, silica gel was added. The residue was purified with silica gel column (DCM:MeOH=100:1.2-100:5) to afford 430 mg product, yield 86%.

$^1$H NMR (400 MHz, CDCl$_3$): δ 8.38 (s, 1H), 7.63 (m, 2H), 7.14-7.01 (m, 6H), 5.69-5.62 (m, 1H), 5.58 (brs, 2H), 3.02-2.96 (m, 1H), 2.82-2.68 (m, 2H), 2.60-2.54 (m, 2H), 2.45-2.32 (m, 1H).

$^{19}$F NMR (376 MHz, CDCl$_3$): δ −118.79 (s).

MS ESI: m/z=404, [M+H]$^+$.

Step 2: (±) cis-3-(4-amino-3-(4-(4-fluorophenoxy)phenyl)-1H-pyrazolo[3,4-d]pyrimidin-1-yl)-1-methylcyclopentan-1-ol and (±) trans-3-(4-amino-3-(4-(4-fluorophenoxy)phenyl)-1H-pyrazolo[3,4-d]pyrimidin-1-yl)-1-methylcyclopentan-1-ol

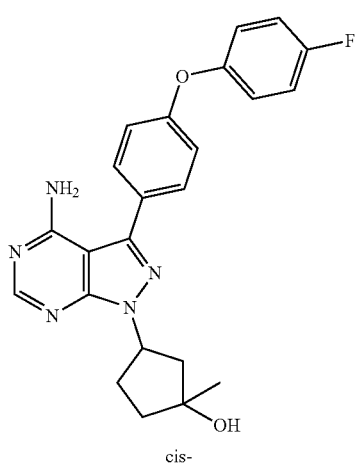
cis-

&

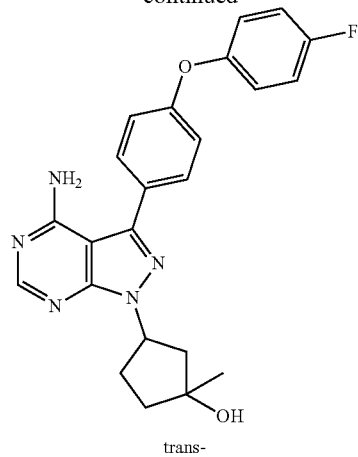
trans-

To a dried 25 mL flask was added anhydrous cerium chloride (0.49 g, 1.98 mmol) and 3 mL anhydrous THF under the protection of Ar, and stirred for 1 h at room temperature. The flask was placed in dry ice-ethanol bath to cool to about −70° C., then 1.6M ether solution of methyl lithium (1.24 mL, 1.98 mmol) was slowly added dropwise. After reacting for 1 h at the same temperature, 3 mL of intermediate 3-(4-amino-3-(4-fluorophenoxy) phenyl)-1H-pyrazolo[3,4-d]pyrimidin-1-yl) cyclopentane-1-one (0.20 g, 0.50 mmol) in THF was added dropwise, and then continued to react for 1.5 h. TLC showed that the reaction was finished. The reacting solution was quenched by 3 mL saturated ammonium chloride aqueous solution, most THF was removed, and extracted with EtOAc (5 mL×3). The combined organic phase was washed with brine (5 mL×3) and then dried with anhydrous sodium sulfate. After filtration, silica gel was added. The residue was purified with silica gel column (DCM:MeOH=100:1.2-100:10) to afford 80 mg Example 14A: (±) cis-3-(4-amino-3-(4-(4-fluorophenoxy)phenyl)-1H-pyrazolo[3,4-d]pyrimidin-1-yl)-1-methylcyclopentan-1-ol, yield 40%; 70 mg Example 14B: (±) trans-3-(4-amino-3-(4-(4-fluorophenoxy) phenyl)-1H-pyrazolo[3,4-d]pyrimidin-1-yl)-1-methylcyclopentan-1-ol, yield: 35%.

Example 14A $^1$H NMR (400 MHz, CDCl$_3$): δ 8.39 (s, 1H), 7.67-7.65 (m, 2H), 7.13-7.05 (m, 6H), 5.64 (brs, 2H), 5.54-5.48 (m, 1H), 2.49-2.41 (m, 1H), 2.39-2.33 (m, 2H), 2.22-2.18 (m, 1H), 2.08-2.02 (m, 1H), 1.80-1.69 (m, 1H), 1.45 (s, 3H).

$^{19}$F NMR (376 MHz, CDCl$_3$): δ −118.82 (s).

MS ESI: m/z=420, [M+H]$^+$.

Example 14B $^1$H NMR (400 MHz, CDCl$_3$): δ 8.37 (s, 1H), 7.66-7.64 (m, 2H), 7.13-7.03 (m, 6H), 5.71-5.63 (m, 1H), 5.49 (brs, 2H), 2.52-2.37 (m, 1H), 2.29-2.26 (m, 1H), 2.25-2.13 (m, 3H), 1.88-1.83 (m, 1H), 1.52 (s, 3H).

$^{19}$F NMR (376 MHz, CDCl$_3$): δ −118.90 (s).

MS ESI: m/z=420, [M+H]$^+$.

Example 15

(1R,3R)-3-(4-amino-3-(4-(3-fluorophenoxy)-1H-pyrazolo[3,4-d]pyrimidin-1-yl) cyclohex-1-ol

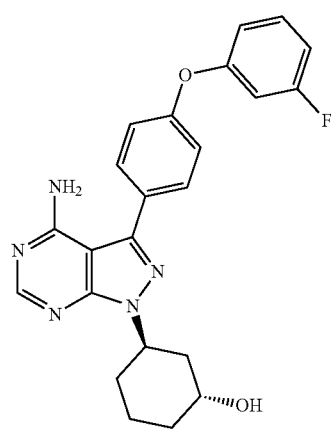 [SMILES: Nc1ncnc2c1c(-c1ccc(Oc3cccc(F)c3)cc1)nn2[C@@H]1CCC[C@@H](O)C1]

Step 1: (1R, 3R)-3-(3-iodo-4-((triphenyl-5-phosphorylidene) amino)-1H-pyrazolo[3,4-d]pyrimidin-1-yl] cyclohexyl acetate

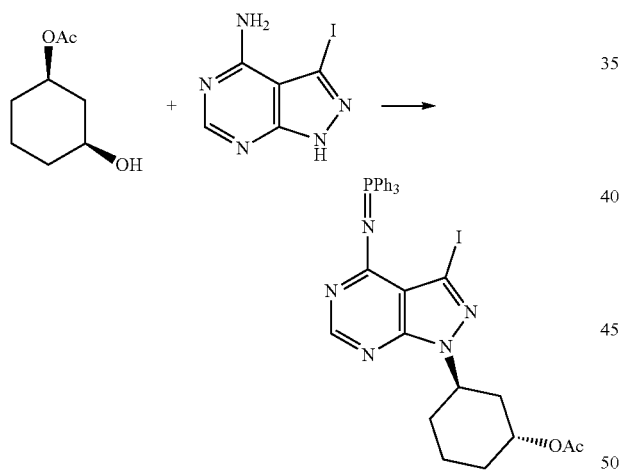

To a dried 250 mL three-necked-flask was added (1R, 3S)-3-hydroxycyclohexyl acetate (1.00 g, 6.32 mmol), 3-iodo-1H-pyrazolo[3,4-d]pyrimidin-4-amine (3.30 g, 12.64 mmol), Ph3P (4.97 g, 18.96 mmol) and 100 mL ultra dry THF in cold ethanol bath. The mixture was added dropwise with DIAD (3.84 g, 18.96 mmol) and continued to stir for 5 h at such temperature. TLC showed that the reaction was finished. 100 mL H₂O was added to the solution, and extracted with EtOAc (100 mL×2). The combined organic phase and washed with brine (100 mL×1) and then dried with anhydrous sodium sulfate. After filtration and concentration, the residue was purified with silica gel column (petroleum ether:ethyl acetate=5:1) to afford 1.20 g product, yield 60%.

MS ESI: m/z=662, [M+H]$^+$.

Step 2: (1R, 3R)-3-(4-amino-3-iodo-1H-pyrazolo[3,4-d]pyrimidin-1-yl) cyclohexyl acetate

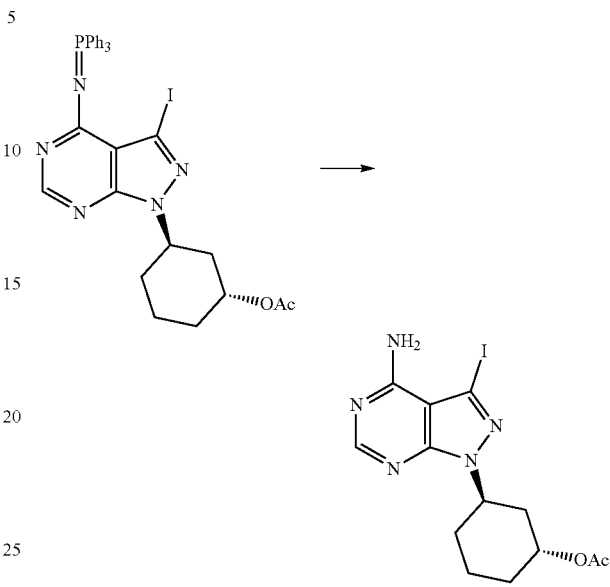

To a 25 mL round-bottom flask was added (1R,3R)-3-(3-iodo-4-((triphenyl-5-phosphorylidene)amino)-1H-pyrazolo[3,4-d]pyrimidin-1-yl]cyclohexyl acetate (100 mg, 0.15 mmol), 15 mL acetic acid and 15 mL H₂O under Ar. The mixture was heated to reflux for 2 h. LCMS showed that the reaction was completed. 50 mL saturated sodium bicarbonate aqueous solution was used to neutralize the system, and extracted with EtOAc (20 mL×3). The combined organic phase and washed with brine (30 mL×1), and then dried with anhydrous sodium sulfate. After filtration and concentration, the residue was purified with silica gel column (DCM: MeOH=100: 1-100:2) to afford 58 mg product, yield 99%.

$^1$H NMR (400 MHz, DMSO-d$_6$): δ 8.20 (s, 1H), 6.57 (s, 2H), 5.17 (s, 1H), 4.97-4.79 (m, 1H), 2.28-2.17 (m, 1H), 2.07 (s, 3H), 1.99 (d, J=13.6 Hz, 1H), 1.89 (dd, J=13.4, 8.4 Hz, 2H), 1.79 (d, J=13.3 Hz, 1H), 1.70 (d, J=3.3 Hz, 2H), 1.64-1.55 (m, 1H).

MS ESI: m/z=402, [M+H]$^+$.

Step 3: 1-(4-bromophenoxy)-3-fluorobenzene

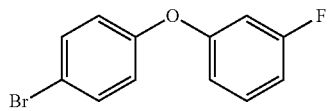 [SMILES: Fc1cccc(Oc2ccc(Br)cc2)c1]

To a dried 1000 mL three-necked-flask was added p-bromoiodobenzene (36.80 g, 130.08 mmol), m-fluorophenol (15.31 g, 136.58 mmol), N,N-bis([1,1'-biphenyl]-2-yl)oxamide (2.55 g, 6.50 mmol), cuprous iodide (1.24 g, 6.50 mmol), potassium phosphate (55.22 g, 260.15 mmol) and 500 mL ultra dry dimethyl sulfoxide. The mixture was exchanged 3 times with Ar, then warmed to 100° C. to react for 10 h. TLC showed that the reaction was completed. The reaction system was added into 1000 mL H₂O and extracted with EtOAc (1000 mL×3). The combined organic phase and filtrated with silica gel, washed with petroleum ether and brine (200 mL×1), and dried with anhydrous sodium sulfate. After filtration and concentration, the residue was purified with silica gel column (petroleum ether) to afford 18.00 g product, yield 60%.

¹H NMR (400 MHz, CDCl₃): δ 7.65 (d, J=8.9 Hz, 0.4H), 7.46 (d, J=8.9 Hz, 1.6H), 7.28 (td, J=8.3, 6.7 Hz, 1H), 6.92 (d, J=8.9 Hz, 1.6H), 6.85-6.74 (m, 2.4H), 6.70 (dt, J=10.1, 2.3 Hz, 1H).

Step 4: (4-(3-fluorophenoxy)phenyl)boric Acid

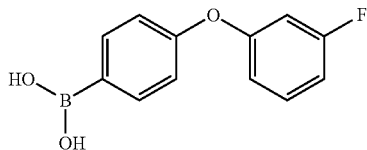 [SMILES: OB(O)c1ccc(Oc2cccc(F)c2)cc1]

To a dried 25 mL three-necked-flask was added 100 mL ultra dry THF and 1-(4-bromophenoxy)-3-fluorobenzene (2.00 g, 7.49 mmol). The flask was then cooled to −70° C. in dry ice-ethanol bath. N-butyl lithium ether solution (1.6 M, 9.73 mmol) was slowly added into the mixture, and the resulting solution was continued to react at the same temperature. The reacting solution was added with triisopropyl boron oxide (1.69 g, 8.99 mmol) and continued to react for 5 h. TLC showed that almost all raw material turned into product. 100 mL 1 N HCl was added into the system, and extracted with DCM (100 mL×3). The combined organic phase was washed with brine (50 mL×1) and then dried with anhydrous sodium sulfate. After filtration and concentration, the residue was purified with silica gel column (petroleum ether:ethyl acetate=3:1) to afford 700 mg product, yield 50%.

¹H NMR (400 MHz, CDCl₃): δ 8.21 (d, J=8.6 Hz, 2H), 7.33 (td, J=8.3, 6.7 Hz, 1H), 7.13 (d, J=8.6 Hz, 2H), 6.87 (dtd, J=7.6, 5.0, 2.5 Hz, 2H), 6.80 (dt, J=10.0, 2.3 Hz, 1H).

Step 5: (1R, 3R)-3-(4-amino-3-(4-(3-fluorophenoxy)phenyl)-1H-pyrazolo[3,4-d]pyrimidin-1-yl) cyclohexyl acetate

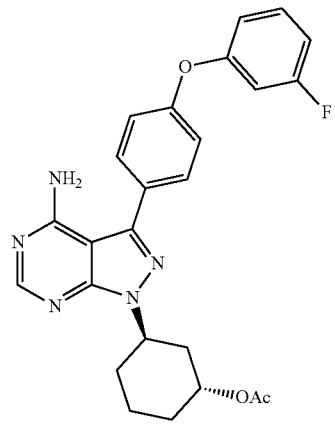 [SMILES: CC(=O)O[C@@H]1CCC[C@@H](n2nc(-c3ccc(Oc4cccc(F)c4)cc3)c3c(N)ncnc32)C1]

To a dried 25 mL two-necked-flask was added successively (1R, 3R)-3-(4-amino-3-iodo-1h-pyrazolo[3,4-d]pyrimidin-1-yl)cyclohexyl acetate (0.10 g, 0.25 mmol), (4-(3-fluorophenoxy) phenyl)boric acid (0.12 g, 0.50 mmol), potassium phosphate (0.16 g, 0.75 mmol), 10 mL of 1,4-dioxane and 5 mL of water. The mixture was exchanged 3 times with Ar and then heated to reflux. The resulting solution was added rapidly with tetratriphenylphosphine palladium (0.10 g, 0.05 mmol) and then reacted for 2 h. LCMS showed that the reaction was completed. The reaction system was cooled and then mixed with 10 mL H₂O, and extracted with DCM (8 mL×3). The combined organic phase was washed with brine (8 mL×3) and dried with anhydrous sodium sulfate. After filtration and concentration, the residue was purified with silica gel column (DCM:MeOH=100:1~100:2) to afford 50 mg product, yield 40%.

MS ESI: m/z=462, [M+H]⁺.

Step 6: (1R,3R)-3-(4-amino-3-(4-(3-fluorophenoxy)-1H-pyrazolo[3,4-d]pyrimidin-1-yl) cyclohex-1-ol

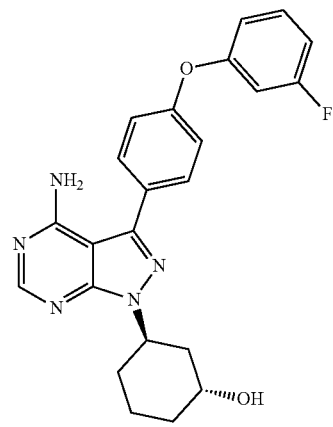 [SMILES: Nc1ncnc2c1c(-c1ccc(Oc3cccc(F)c3)cc1)nn2[C@@H]1CCC[C@@H](O)C1]

To a 25 mL flask was added (1R, 3R)-3-(4-amino-3-(3-fluorophenoxy) phenyl)-1H-pyrazolo[3,4-d]pyrimidin-1-yl) cyclohexyl acetate (50 mg, 0.11 mmol), LiOH (13 mg, 0.54 mmol) and 5 mL MeOH. The mixture was stirred at room temperature overnight. LCMS showed that the reaction was completed. The reacting solution was filtrated to remove LiOH. The filtrate was purified with silica gel column to afford 48 mg product, yield 99%.

¹H NMR (400 MHz, CDCl₃): δ 8.30 (s, 1H), 7.62 (d, J=8.6 Hz, 2H), 7.25 (td, J=8.3, 6.7 Hz, 1H), 7.11 (d, J=8.6 Hz, 2H), 6.79 (ddd, J=8.3, 6.3, 2.2 Hz, 2H), 6.70 (dt, J=10.1, 2.3 Hz, 1H), 5.54 (brs, 2H), 5.28-5.08 (m, 1H), 4.34 (m, 1H), 2.37-2.23 (m, 1H), 2.18-1.85 (m, 4H), 1.76-1.66 (m, 2H), 1.61-1.54 (m, 1H).

MS ESI: m/z=420, [M+H]⁺.

Example 16

(1R, 3R)-3-(4-amino-3-(2-fluoro-4-phenoxyphenyl)-1H-pyrazolo[3,4-d]pyrimidin-1-yl)cyclohex-1-ol

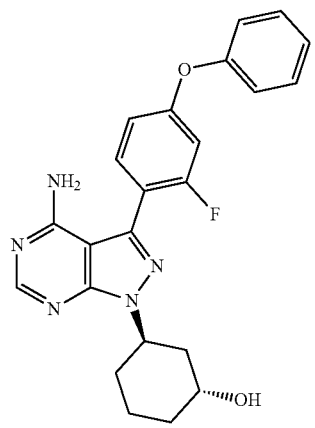 [SMILES: Nc1ncnc2c1c(-c1ccc(Oc3ccccc3)cc1F)nn2[C@@H]1CCC[C@@H](O)C1]

Step 1: 1-bromo-2-fluoro-4-phenoxybenzene

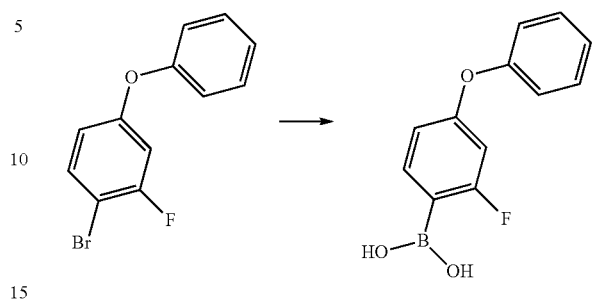

To a 500 mL three-necked-flask was added 4-bromo-3-fluorophenol (10.00 g, 52.36 mmol), phenylboronic acid (12.77 g, 104.71 mmol), triethylamine (10.60 g, 104.71 mmol), anhydrous copper acetate (4.754 g, 52.356 mmol) 20 g 4 Å molecular sieve and 300 mL DCM. The mixture was reacted overnight at oxygen atmosphere. TLC showed that the reaction was completed. The reacting solution was filtrated through diatomite and washed with 500 mL DCM. After concentration, the residue was purified with silica gel column (petroleum ether) to afford 6.00 g product, yield 50%.

$^1$H NMR (400 MHz, CDCl$_3$): δ 7.45 (dd, J=8.7, 8.0 Hz, 1H), 7.38 (dd, J=8.5, 7.5 Hz, 2H), 7.18 (t, J=7.4 Hz, 1H), 7.03 (dd, J=8.6, 1.0 Hz, 2H), 6.76 (dd, J=9.8, 2.7 Hz, 1H), 6.69 (ddd, J=8.8, 2.7, 1.1 Hz, 1H).

Step 2: (2-fluoro-4-phenoxyphenyl) boric Acid

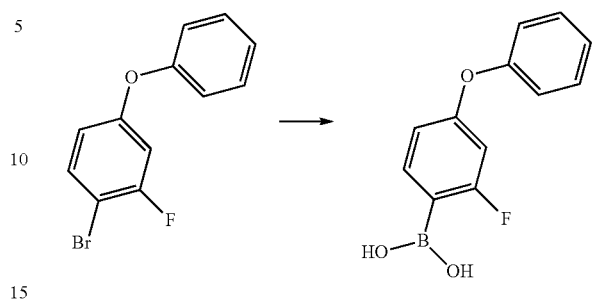

To a dried 100 mL flask was added 1-(4-bromophenoxy)-3-fluorobenzene (1.00 g, 3.74 mmol) and 50 ml ultra dry THF. The flask was cooled to −70° C. in dry ice-ethanol bath. Hexane solution of n-butyl lithium (1.6 M, 4.87 mmol) was added dropwise, and continued to react for 2 h at same temperature. Triisopropoxyboron (0.85 g, 4.49 mmol) was added into the solution. TLC showed that the reaction was completed. The reaction system was mixed slowly with 100 mL 0.5 N HCl aqueous solution and extracted with DCM (30 mL×3). The combined organic phase and washed with brine (50 mL×1) and then dried with anhydrous sodium sulfate. After filtration and concentration, the crude product was used directly in the next step.

Step 3: (1R, 3R)-3-(4-amino-3-(2-fluoro-4-phenoxyphenyl)-1H-pyrazolo[3,4-d]pyrimidin-1-yl) cyclohexyl acetate

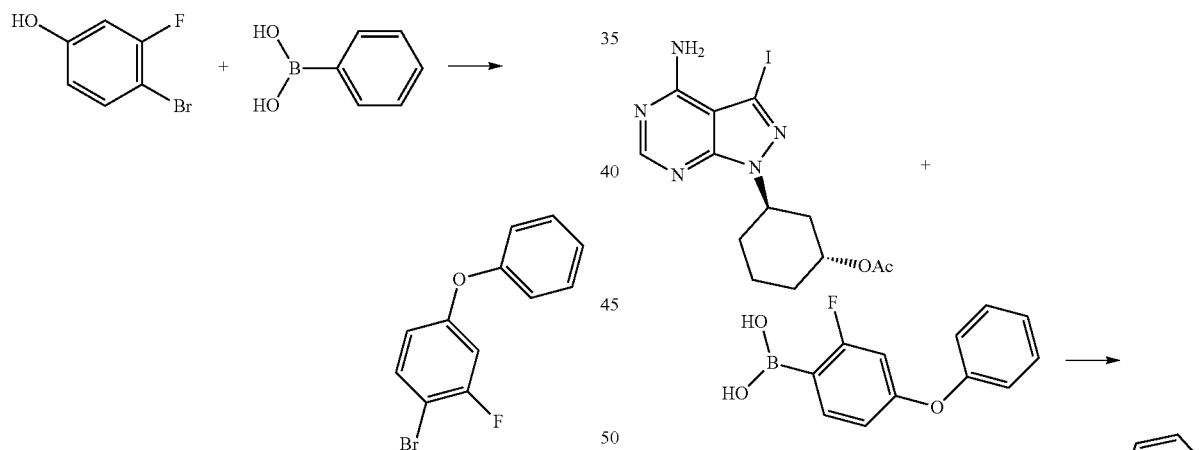

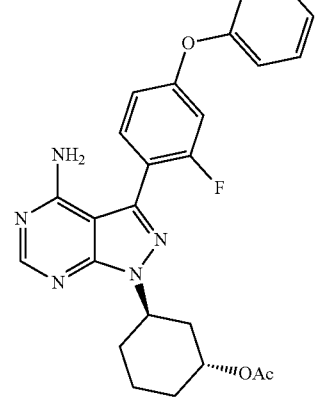

To a 25 mL two-necked-flask was added (1R, 3R)-3-(4-amino-3-iodo-1h-pyrazolo[3,4-d]pyrimidin-1-yl) cyclohexyl acetate (0.25 g, 0.62 mmol), (2-fluoro-4-phenoxyphenyl) boric acid (0.19 g, 0.81 mmol) and potassium phosphate (0.30 g, 1.87 mmol), 10 mL of 1,4-dioxane and 5 mL of H₂O. The mixture was exchanged with Ar for 3 times. The resulting solution was mixed with tetratriphenylphosphine palladium (144 mg, 0.13 mmol), heated and refluxed. The reaction was finished 2 hours later. The reaction system was mixed with 15 mL H₂O and then extracted with DCM (20 mL×3). The combined organic phase was washed with brine (20 mL×3) and then dried with anhydrous sodium sulfate. After filtration and concentration, the residue was purified with silica gel column (DCM:MeOH=100:1) to afford 150 mg product, yield 52%.

¹H NMR (400 MHz, CDCl₃): δ 8.38 (s, 1H), 7.52 (t, J=8.5 Hz, 1H), 7.42 (dd, J=8.4, 7.6 Hz, 2H), 7.22 (t, J=7.4 Hz, 1H), 7.10 (d, J=7.6 Hz, 2H), 6.94 (dd, J=8.5, 2.3 Hz, 1H), 6.86 (dd, J=11.2, 2.4 Hz, 1H), 5.35 (brs, 3H), 5.15 (ddd, J=16.0, 11.3, 4.4 Hz, 1H), 2.51-2.40 (m, 1H), 2.22 (d, J=13.7 Hz, 1H), 2.13 (s, 3H), 2.11-2.08 (m, 1H), 2.08-1.99 (m, 1H), 1.99-1.71 (m, 4H).

MS ESI: m/z=462, [M+H]⁺.

Step 4: (1R, 3R)-3-(4-amino-3-(2-fluoro-4-phenoxyphenyl)-1H-pyrazolo[3,4-d]pyrimidin-1-yl) cyclohex-1-ol

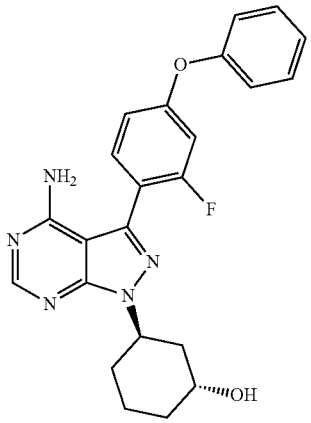 [SMILES: Nc1ncnc2c1c(-c1ccc(Oc3ccccc3)cc1F)nn2[C@@H]1CCC[C@@H](O)C1]

To a 25 mL flask was added (1R, 3R)-3-(4-amino3-(2-fluoro-4-phenoxyphenyl)-1h-pyrazo-3,4-d-pyrimidine-1-yl) cyclohexyl acetate (100 mg, 0.22 mmol), LiOH (20 mg, 0.87 mmol) and 5 mL of methanol. The mixture was stirred overnight at room temperature. TLC showed that the reaction was completed. Silica gel column (DCM:MeOH=100:1100:2) was used to purify to afford 80 mg product, yield 80%.

¹H NMR (400 MHz, CDCl₃): δ 8.33 (s, 1H), 7.51 (t, J=8.5 Hz, 1H), 7.41 (t, J=7.9 Hz, 2H), 7.21 (t, J=7.4 Hz, 1H), 7.09 (d, J=7.9 Hz, 2H), 6.92 (dd, J=8.5, 2.0 Hz, 1H), 6.88-6.80 (m, 1H), 5.60 (brs, 2H), 5.33-5.19 (m, 1H), 4.39 (m, 1H), 2.35-2.28 (m, 1H), 2.17-2.12 (m, 1H), 2.10-2.03 (m, 2H), 2.03-1.93 (m, 1H), 1.89-1.70 (m, 2H), 1.65-1.58 (m, 1H).

MS ESI: m/z=420, [M+H]⁺.

Example 17

(1R,3R)-3-(4-amino-3-(4-(2-fluorophenoxy)phenyl)-1H-pyrazolo[3,4-d]pyrimidin-1-yl)cyclohex-1-ol

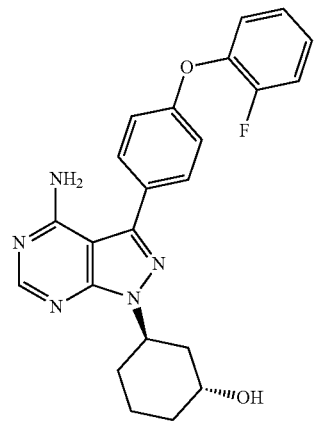 [SMILES: Nc1ncnc2c1c(-c1ccc(Oc3ccccc3F)cc1)nn2[C@@H]1CCC[C@@H](O)C1]

Step 1: 1-(4-bromophenoxy)-2-fluorobenzene

To a 250 mL flask was added o-fluorophenol (2.00 g, 17.84 mmol), p-bromophenylboric acid (7.17 g, 35.68 mmol), copper acetate (4.75 g, 17.84 mmol), 150 mL ultra dry dichloromethane and 20 g 4 A molecular sieve. The mixture was placed at oxygen atmosphere, and triethylamine (3.61 g, 35.68 mmol) was added dropwise to the reaction system under room temperature stirring. 10 hours later, TLC showed that the reaction was completed. The reacting solution was filtrated directly through diatomite and then washed with 150 mL petroleum ether. After concentration, the residue was purified with silica gel column (petroleum ether) to afford 2.30 g product, yield 48%.

¹H NMR (400 MHz, CDCl₃): δ 7.41 (d, J=8.9 Hz, 2H), 7.22-7.01 (m, 4H), 6.85 (d, J=8.9 Hz, 2H).

Step 2

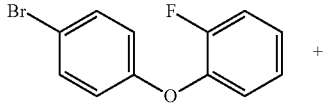

-continued

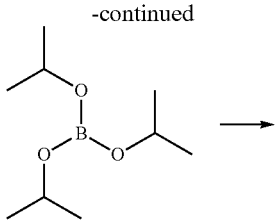

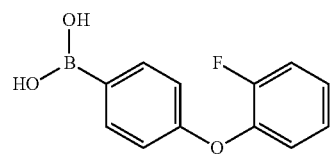

To a dried 50 mL two-necked-flask was added 1-(4-bromophenoxy)-2-fluorobenzene (0.50 g, 1.87 mmol) and 20 mL ultra dry THF under Ar. the mixture was cooled in dry ice-ethanol bath and added dropwise with hexane solution of n-butyl lithium (1.6 M, 1.52 mL, 2.43 mmol). The resulting solution was stirred for 30 min and mixed with triisopropoxyborate (0.42 g, 2.25 mmol). 2 hours later, TLC showed that the reaction was completed. The reacting solution was mixed with 15 mL saturated ammonium chloride aqueous solution and extracted with EtOAc (15 mL×3). The combined organic phase and washed with brine (20 mL×1) and then dried with anhydrous sodium sulfate. After filtration and concentration, the residue was purified with silica gel column (petroleum ether:ethyl acetate=3:1) to afford 200 mg product, yield 46%.

Step 3: (1R, 3R)-3-(4-amino-3-(4-(2-fluorophenoxy)phenyl)-1H-pyrazolo[3,4-d]pyrimidin-1-yl) cyclohexyl acetate

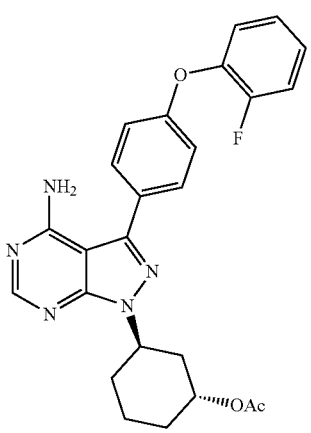 [SMILES: CC(=O)O[C@@H]1CCC[C@@H](n2nc(-c3ccc(Oc4ccccc4F)cc3)c3c(N)ncnc32)C1]

To a 25 mL two-necked-flask was added (1R, 3R)-3-(4-amino-3-iodo-1h-pyrazolo[3,4-d]pyrimidin-1-yl)cyclohexyl acetate (0.50 g, 1.25 mmol), (4-(2-fluorophenoxy) phenyl) boric acid (0.38 g, 1.62 mmol), potassium phosphate (0.79 g, 3.74 mmol), tetratriphenylphosphine palladium (0.29 g, 0.25 mmol), 20 mL of 1,4-dioxane and 10 mL of H$_2$O under Ar. The mixture was heated to reflux for 1.5 h. TLC showed that the reaction was completed. The reaction system was added with 15 mL H$_2$O and extracted with DCM (10 mL×3). The combined organic phase was washed with brine (20 mL×1) and then dried with anhydrous sodium sulfate. After filtration and concentration, the residue was purified with silica gel column (DCM:methanol=100:1) to afford 390 mg product, yield 69%.

MS ESI: m/z=462, [M+H]$^+$.

Step 4: (1R, 3R)-3-(4-amino-3-(4-(2-fluorophenoxy)phenyl)-1H-pyrazolo[3,4-d]pyrimidin-1-yl) cyclohex-1-ol

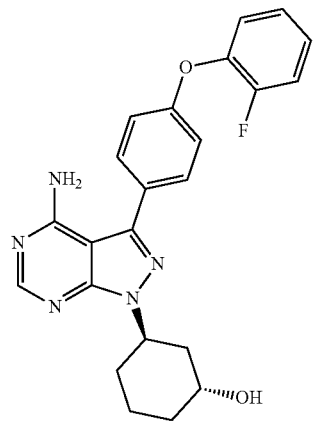 [SMILES: Nc1ncnc2c1c(-c1ccc(Oc3ccccc3F)cc1)nn2[C@@H]1CCC[C@@H](O)C1]

To a 25 mL two-necked-flask was added (1R, 3R)-3-(4-amino-3-(4-(2-fluorophenoxy) phenyl)-1H-pyrazolo[3,4-d] pyrimidin-1-yl) cyclohexyl acetate (0.30 g, 0.65 mmol), LiOH (0.05 g, 1.95 mmol), 3 mL MeOH. The mixture was stirred overnight at room temperature. TLC showed that the reaction was completed. The reaction system was mixed with 5 mL H$_2$O and extracted with DCM (5 mL×3). The combined organic phase and then dried with anhydrous sodium sulfate. After filtration and concentration, the residue was purified with silica gel column (DCM:MeOH=100:2) to afford 250 mg product, yield 90%.

$^1$H NMR (400 MHz, CDCl$_3$): δ 8.36 (s, 1H), 7.64 (d, J=8.7 Hz, 1H), 7.40-7.32 (m, 0.5H), 7.23 (m, 1H), 7.21-7.14 (m, 3H), 7.13-7.10 (m, 2H), 7.05 (d, J=7.7 Hz, 0.5H), 5.59 (brs, 2H), 5.29-5.22 (m, 1H), 4.40 (m, 1H), 2.39-2.32 (m, 1H), 2.21-1.97 (m, 4H), 1.81-1.73 (m, 2H), 1.68-1.61 (m, 1H).

$^{19}$F NMR (376 MHz, CDCl$_3$): δ -130.18 (s).

MS ESI: m/z=420, [M+H]$^+$.

Example 18

(1R, 3R)-3-(4-amino-3-(4-(2,6-difluorophenoxy)phenyl)-1H-pyrazolo[3,4-d]pyrimidin-1-yl)cyclohex-1-ol

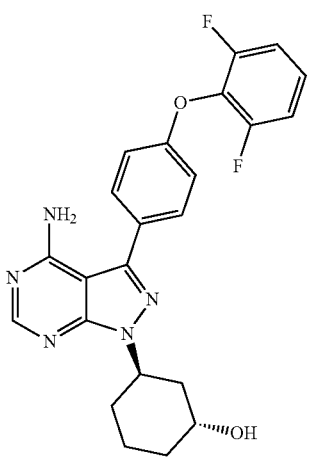 [SMILES: Nc1ncnc2c1c(-c1ccc(Oc3c(F)cccc3F)cc1)nn2[C@@H]1CCC[C@@H](O)C1]

Step 1: 2-(4-bromophenoxy)-1,3-difluorobenzene

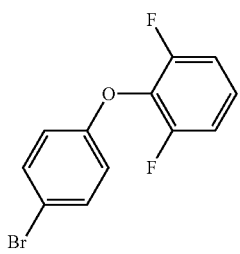 [SMILES: Fc1cccc(F)c1Oc1ccc(Br)cc1]

To a 250 mL flask was added 2,6-difluorophenol (2.00 g, 15.37 mmol), p-bromophenylboronic acid (6.18 g, 30.75 mmol), 20 g 4 Å molecular sieve, copper acetate (4.75 g, 15.37 mmol) and 150 mL ultra dry DCM. The mixture was placed at oxygen atmosphere. Triethylamine (3.11 g, 30.75 mmol) was added dropwise to the reaction system by stirring under room temperature. 3 hours later, TLC showed that the reaction was completed. The reacting solution was filtrated directly through diatomite. After concentration, the residue was purified with silica gel column (petroleum ether) to afford 2.40 g product, yield 55%.

Step 2: (4-(2,6-difluorophenyl)phenyl)boric Acid

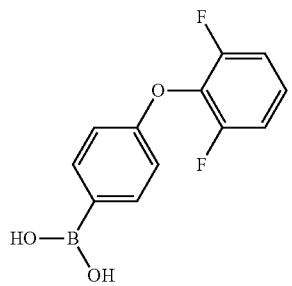 [SMILES: OB(O)c1ccc(Oc2c(F)cccc2F)cc1]

To a dried 25 mL two-necked-flask was added 2-(4-bromophenoxy)-1,3-difluorobenzene (0.50 g, 1.75 mmol) and 15 mL ultra dry THF. The flask was cooled to 70° C. in dry ice-ethanol bath. The mixture was added dropwise with hexane solution of n-butyl lithium (1.6 M, 1.43 mL, 2.28 mmol) and reacted for 30 min. Triisopropoxyborate (0.40 g, 2.11 mmol) was added into the solution to react 2 hours, TLC showed that the reaction was completed. The reacting solution was mixed with 15 mL saturated ammonium chloride aqueous solution and extracted with EtOAc (15 mL×3). The combined organic phase and washed with brine (20 mL×3) and then dried with anhydrous sodium sulfate. After filtration and concentration, the residue was purified with silica gel column (petroleum ether:ethyl acetate=3:1) to afford 350 mg product, yield 80%.

$^1$H NMR (400 MHz, CDCl$_3$): δ 7.40 (d, J=9.1 Hz, 2H), 7.21-7.10 (m, 1H), 7.08-6.95 (m, 2H), 6.83 (d, J=9.0 Hz, 2H).

Step 3: (1R, 3R)-3-(4-amino-3-(4-(2,6-difluorophenoxy)phenyl)-1H-pyrazolo[3,4-d]pyrimidin-1-yl)cyclohexyl acetate

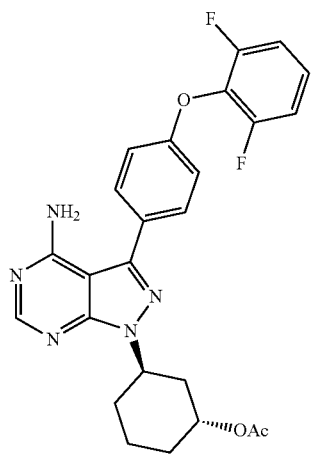 [SMILES: CC(=O)O[C@@H]1CCC[C@@H](n2nc(-c3ccc(Oc4c(F)cccc4F)cc3)c3c(N)ncnc32)C1]

To a dried 50 mL flask was added cyclohexyl (1R, 3R)-3-(4-amino-3-iodo-1H-pyrazolo[3,4-d]pyrimidin-1-yl)acetate (0.25 g, 0.62 mmol), (4-(2,6-difluorophenyloxy)phenyl)boric acid (0.20 g, 0.81 mmol), potassium phosphate (0.40 g, 1.87 mmol), tetratriphenylphosphine palladium (144 mg, 0.13 mmol), 20 mL 1,4-dioxane and 10 mL H₂O under Ar. The mixture was warmed to 100° C. to react for 1.5 h. LCMS showed that the reaction was completed. The reaction system was mixed slowly with 15 mL 0.1 N HCl aqueous solution and extracted with EtOAc (15 mL×3). The combined organic phase was washed with brine (15 mL×3) and then dried with anhydrous sodium sulfate. After filtration and concentration, the residue was purified with silica gel column (DCM:MeOH=100:1) to afford 240 mg product, yield 80%.

MS ESI: m/z=480, [M+H]⁺.

Step 4: (1R, 3R)-3-(4-amino-3-(4-(2,6-difluorophenoxy)phenyl)-1H-pyrazolo[3,4-d]pyrimidin-1-yl)cyclohex-1-ol

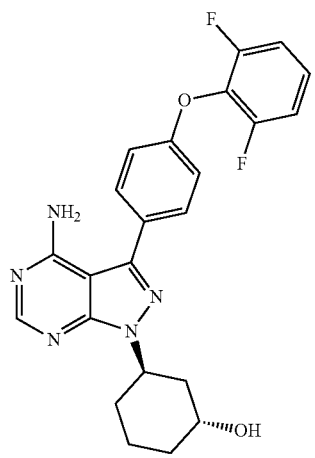 [SMILES: Nc1ncnc2c1c(-c1ccc(Oc3c(F)cccc3F)cc1)nn2[C@@H]1CCC[C@@H](O)C1]

To a 25 mL flask was added cyclohexyl (1R, 3R)-3-(4-amino-3-(4-(2,6-difluorophenoxy)phenyl)-1H-pyrazolo[3,4-d]pyrimidin-1-yl)acetate (0.20 g, 0.42 mmol), LiOH (30 mg, 1.25 mmol) and 3 mL MeOH. The mixture was stirred overnight at room temperature. TLC showed that the reaction was completed. The reaction system was mixed with 10 mL H₂O and extracted with EtOAc (10 mL×3). The organic phase was combined, washed with brine (10 mL×3) and then dried with anhydrous sodium sulfate. After filtration and concentration, the residue was purified with silica gel column (DCM:MeOH=100:1~ 100:2) to afford 170 mg product, yield 93%.

¹H NMR (400 MHz, CDCl₃): δ 8.37 (d, J=1.5 Hz, 1H), 7.63 (d, J=8.6 Hz, 1H), 7.49-7.38 (m, 1H), 7.34-7.29 (m, 1H), 7.23-7.14 (m, 1H), 7.11-6.99 (m, 3H), 5.51 (brs, 1H), 5.35 (brs, 1H), 5.31-5.20 (m, 1H), 4.40 (s, 1H), 2.50-2.24 (m, 1H), 2.14-1.97 (m, 4H), 1.82 (m, 2H), 1.68-1.54 (m, 1H).

MS ESI: m/z=438, [M+H]⁺.

Example 19

(1R, 3R)-3-(4-amino-3-(4-(2-fluoro-3-methoxyphenoxy)phenyl)-1H-pyrazolo[3,4-d]pyrimidin-1-yl)cyclohex-1-ol

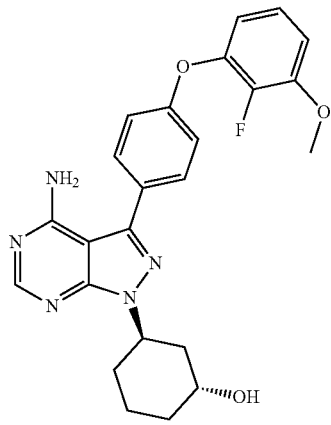

Step 1:
1-(4-iodophenoxy)-2-fluoro-3-methoxybenzene

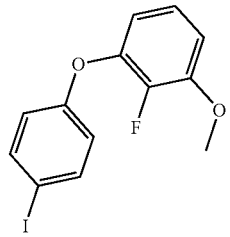 [SMILES: COc1cccc(Oc2ccc(I)cc2)c1F]

To a dried 100 mL flask was added 2-fluoro-3-methoxyphenol (1.00 g, 7.04 mmol), 4-iodobenzoic acid (3.49 g, 14.07 mmol), copper acetate (4.75 g, 7.04 mmol), 10 g 4 A molecular sieve and 50 mL ultra dry DCM, and triethylamine (3.11 g, 30.75 mmol) was added dropwise. The mixture was stirred to reacted overnight at oxygen atmosphere under room temperature. TLC showed that the reaction was completed. The reacting solution was filtrated directly through diatomite. silica gel column (petroleum ether:ethyl acetate=9:1) was used to purify to afford 1.50 g product, yield 62%.

¹H NMR (400 MHz, CDCl₃): δ 7.59 (d, J=8.9 Hz, 2H), 7.02 (td, J=8.4, 2.2 Hz, 1H), 6.80 (dd, J=11.5, 4.3 Hz, 1H), 6.75 (d, J=8.8 Hz, 2H), 6.64 (ddd, J=8.3, 6.9, 1.4 Hz, 1H), 3.92 (s, 3H).

Step 2: 2-(4-(2-fluoro-3-methoxyphenoxy) phenyl)-4,4,5,5-tetramethyl-1,3,2-dioxaborane

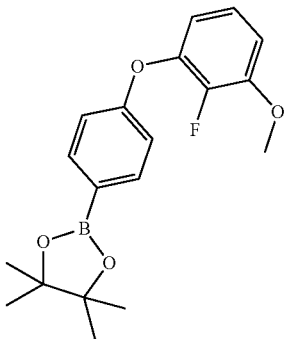 [SMILES: COc1cccc(Oc2ccc(B3OC(C)(C)C(C)(C)O3)cc2)c1F]

To a dried 25 mL two-necked-flask was added successively PdCl$_2$(dppf) (6 mg, 0.01 mmol), potassium acetate (85 mg, 0.87 mmol) and pinaconazole (148 mg, 0.58 mmol), 1-(4-iodophenoxy)-2-fluoro-3-methoxybenzene (100 mg, 0.29 mmol) and 10 mL DMSO under N$_2$. The mixture was heated to 85° C. and reacted for 1.5 h. TLC showed that the reaction was completed. After cooled to room temperature, the reaction system was mixed with 15 mL H$_2$O and extracted with DCM (10 mL×3). The combined organic phase was washed with brine (15 mL×3) and dried with anhydrous sodium sulfate. After filtration and concentration, the residue was purified with silica gel column (petroleum ether:ethyl acetate=3:1) to afford 44 mg product, yield 45%.

$^1$H NMR (400 MHz, CDCl$_3$): δ 7.81-7.70 (m, 2H), 7.01 (td, J=8.4, 2.2 Hz, 1H), 6.96 (d, J=8.5 Hz, 2H), 6.81-6.76 (m, 1H), 6.66 (ddd, J=8.3, 6.9, 1.4 Hz, 1H), 3.92 (s, 3H), 1.33 (s, 12H).

Step 3: (1R, 3R)-3-(4-amino-3-(4-(2-fluoro-3-methoxyphenoxy)phenyl)-1H-pyrazolo[3,4-d]pyrimidin-1-yl)cyclohexyl acetate

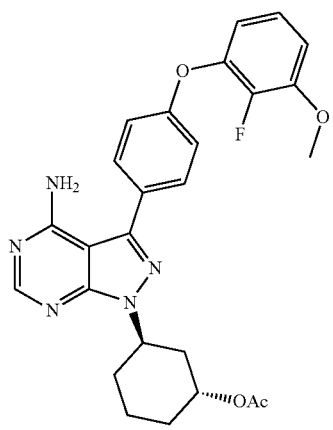 [SMILES: COc1cccc(Oc2ccc(-c3nn([C@@H]4CCC[C@@H](OC(C)=O)C4)c4ncnc(N)c34)cc2)c1F]

To a 50 mL two-necked-flask was added cyclohexyl (1R, 3R)-3-(4-amino-3-iodo-1h-pyrazolo[3,4-d]pyrimidin-1-yl) acetate (0.30 g, 0.75 mmol), 2-(4-(2-fluoro-3-methoxyphenoxy) phenyl)-4,4,5,5-tetramethyl-1,3,2-dioxaborane (0.30 g, 0.90 mmol), potassium carbonate (0.40 g, 2.24 mmol) and tetratriphenylphosphine palladium (173 mg, 0.15 mmol). The mixture was exchanged 3 times with Ar, and 20 mL 1,4-dioxane and 10 mL H$_2$O were added. The resulting solution was heated to reflux for an hour, and LCMS showed that the reaction was completed. After cooled to room temperature, the reaction system was added with 10 mL H$_2$O and extracted with DCM (10 mL×3). The combined organic phase was washed with brine (15 mL×3) and then dried with anhydrous sodium sulfate. After filtration and concentration, the residue was purified with silica gel column (DCM:MeOH=100:1) to afford 250 mg product, yield 70%.

MS ESI: m/z=492, [M+H]$^+$.

Step 4: (1R, 3R)-3-(4-amino-3-(4-(2-fluoro-3-methoxyphenoxy)phenyl)-1H-pyrazolo[3,4-d]pyrimidin-1-yl) cyclohex-1-ol

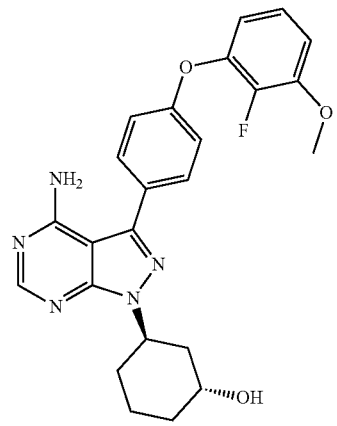 [SMILES: COc1cccc(Oc2ccc(-c3nn([C@@H]4CCC[C@@H](O)C4)c4ncnc(N)c34)cc2)c1F]

To a 25 mL flask was added cyclohexyl (1R, 3R)-3-(4-amino-3-(4-(2-fluoro-3-methoxyphenoxy)phenyl)-1H-pyrazolo[3,4-d]pyrimidin-1-yl)acetate (0.25 g, 0.51 mmol), LiOH (37 mg, 1.53 mmol) and 5 mL MeOH. The mixture was stirred overnight at room temperature. TLC showed that the reaction was completed. The reaction system was mixed with 5 mL H$_2$O and extracted with DCM (5 mL×3). The combined organic phase was washed with brine (10 mL×1) and dried with anhydrous sodium sulfate. After filtration and concentration, the residue was purified with silica gel column (DCM:MeOH=100:1~ 100:2) to afford 200 mg product, yield 88%.

$^1$H NMR (400 MHz, CDCl$_3$): δ 8.35 (s, 1H), 7.63 (d, J=8.7 Hz, 2H), 7.13 (d, J=8.6 Hz, 2H), 7.07 (td, J=8.4, 2.1 Hz, 1H), 6.89-6.81 (m, 1H), 6.73 (ddd, J=8.3, 6.9, 1.5 Hz, 1H), 5.60 (brs, 2H), 5.26 (m, 1H), 4.44-4.36 (m, 1H), 3.94 (s, 3H), 2.52-2.24 (m, 1H), 2.29-1.95 (m, 5H), 1.84-1.80 (m, 1H), 1.65-1.60 (m, 1H).

$^{19}$F NMR (376 MHz, CDCl$_3$): δ −152.86 (s).

MS ESI: m/z=450, [M+H]$^+$.

Example 20

(1s,4s)-4-(4-amino-3-(4-(2-fluoro-3-methoxyphenoxy)phenyl)-1H-pyrazolo[3,4-d]pyrimidin-1-yl)cyclohex-1-ol b Step 1: (1s,4s)-4-(4-amino-3-iodo-1H-pyrazolo[3,4-d]pyrimidin-1-yl)cyclohex-1-ol

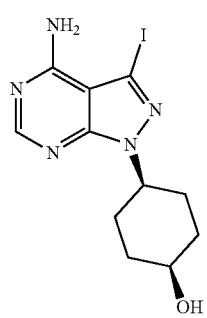 [SMILES: Nc1ncnc2c1c(I)nn2[C@H]1CC[C@@H](O)CC1]

To a dried 500 mL two-necked-flask was added 3-iodo-1H-pyrazolo[3,4-d]pyrimidin-4-amine (5.00 g, 19.16 mmol), 1,4-cyclohexanediol (cis:trans=1:0.7, NMR content) (4.45 g, 38.3 mmol), triphenylphosphine (10.05 g, 38.31 mmol) and 200 mL ultra dry THF under Ar. The flask was cooled in dry ice-ethanol bath. Diisopropyl azodicarboxylate (7.75 g, 38.31 mmol) was added into the mixture, and reacted for 5 hours. LCMS showed that the reaction was completed. The resulting solution was filtrated to obtain 4.50 g light yellow solid. The mother liquor was concentrated and purified with silica gel column (DCM:MeOH=100:1) to afford 0.8 g product, yield 73%.

MS ESI: m/z=360, [M+H]$^+$.

Step 2: (1s, 4s)-4-(4-amino-3-(4-(2-fluoro-3-methoxyphenoxy)phenyl)-1H-pyrazolo[3,4-d]pyrimidin-1-yl)cyclohex-1-ol

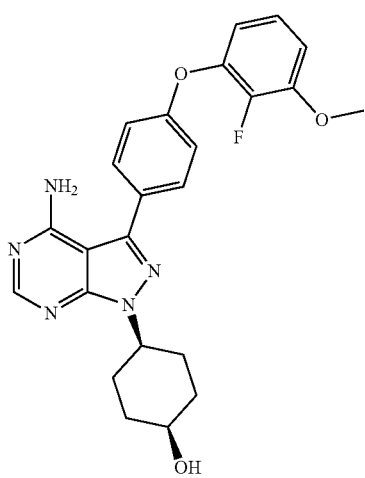 [SMILES: COc1cccc(Oc2ccc(-c3nn([C@H]4CC[C@@H](O)CC4)c4ncnc(N)c34)cc2)c1F]

To a 50 mL two-necked-flask was added (1s, 4s)-4-(4-amino-3-iodo-1H-pyrazolo[3,4-d]pyrimidin-1-yl)cyclohex-1-ol (80 mg, 0.22 mmol), 2-(4-(2-fluoro-3-methoxyphenoxy)phenyl)-4,4,5,5-tetramethyl-1,3,2-dioxaborane (97 mg, 0.29 mmol), potassium carbonate (118 mg, 0.67 mmol) and tetratriphenylphosphine palladium (51 mg, 0.05 mmol). The mixture was exchanged for 3 times with Ar, and 5 mL 1,4-dioxane and 2.5 mL H$_2$O was added successively. The resulting solution was heated to reflux for an hour, and LCMS showed that the reaction was completed. After cooled to room temperature, 5 mL H$_2$O was added, and extracted with DCM (5 mL×3). The combined organic phase was washed with brine (5 mL×3) and then dried with anhydrous sodium sulfate. After filtration and concentration, the residue was purified with silica gel column (DCM:MeOH=100:1) to afford 65 mg product, yield 65%.

$^1$H NMR (400 MHz, CDCl$_3$): δ 8.37 (s, 1H), 7.63 (d, J=8.7 Hz, 2H), 7.13 (d, J=8.6 Hz, 2H), 7.07 (td, J=8.4, 2.1 Hz, 1H), 6.84 (t, J=7.2 Hz, 1H), 6.77-6.69 (m, 1H), 5.44 (brs, 2H), 4.87-4.74 (m, 1H), 3.94 (s, 3H), 3.82 (m, 1H), 2.30-1.96 (m, 6H), 1.55 (m, 2H).

$^{19}$F NMR (376 MHz, CDCl$_3$): δ −152.83 (s).

MS ESI: m/z=450, [M+H]$^+$.

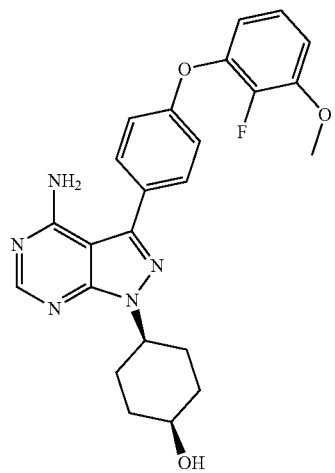

Example 21

(1r, 4r)-4-(4-amino-3-(4-(2-fluoro-3-methoxyphenoxy)phenyl)-1H-pyrazolo[3,4-d]pyrimidin-1-yl)cyclohex-1-ol

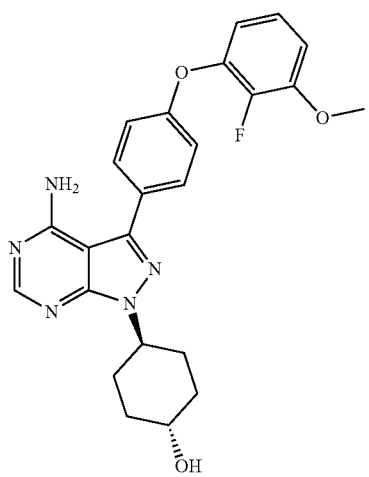 [SMILES: COc1cccc(Oc2ccc(-c3nn([C@H]4CC[C@H](O)CC4)c4ncnc(N)c34)cc2)c1F]

Step 1: (1R, 4R)-4-(4-amino-3-(4-(2-fluoro-3-methoxyphenoxy)phenyl)-1H-pyrazolo[3,4-d]pyrimidin-1-yl) cyclohexyl 4-nitrobenzoate

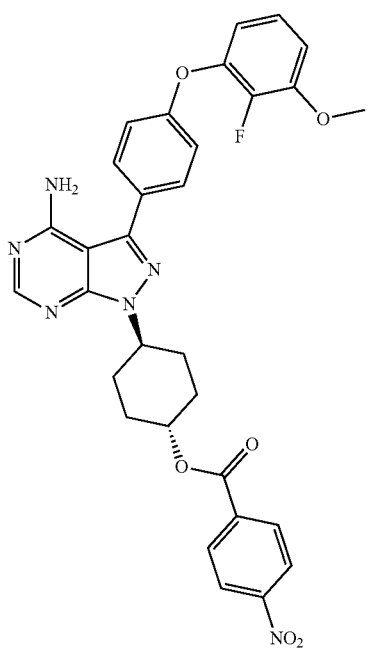 [SMILES: COc1cccc(Oc2ccc(-c3nn([C@H]4CC[C@H](OC(=O)c5ccc([N+](=O)[O-])cc5)CC4)c4ncnc(N)c34)cc2)c1F]

To a dried 25 mL two-necked-flask was added (1s, 4s)-4-(4-amino-3-(4-(2-fluoro-3-methoxyphenoxy)phenyl)-1H-pyrazolo[3,4-d]pyrimidin-1-yl)cyclohex-1-ol (80 mg, 0.18 mmol), 4-nitrobenzoic acid (59 mg, 0.36 mmol), PPh$_3$ (93 mg, 0.36 mmol) and 5 mL ultra dry THF. The mixture was cooled in ice-ethanol bath and diisopropyl azodicarboxylate (72 mg, 0.36 mmol) was added dropwise, and reacted for 3 h. LCMS showed that the reaction was completed. The reaction system was added with 5 mL H$_2$O and extracted with DCM (5 mL×3). The combined organic phase was dried with anhydrous sodium sulfate. After filtration and concentration, the residue was purified with silica gel column (DCM:MeOH=100:1) to afford 80 mg product, yield 78%.

MS ESI: m/z=599, [M+H]$^+$.

Step 2: (1R, 4R)-4-(4-amino-3-(4-(2-fluoro-3-methoxyphenoxy)phenyl)-1H-pyrazolo[3,4-d]pyrimidin-1-yl)cyclohex-1-ol

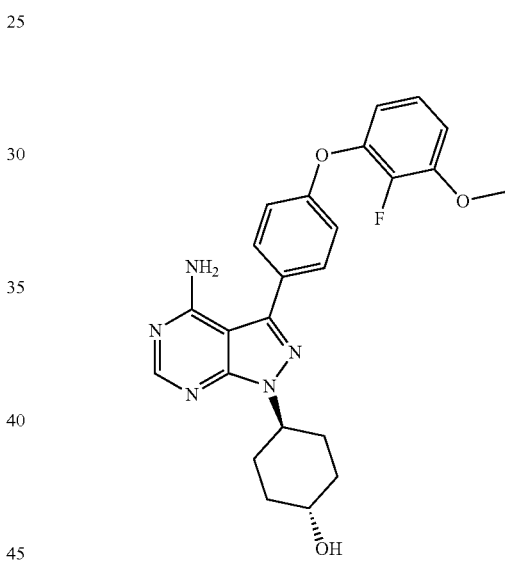

To a 25 mL flask was added (1R, 4R)-4-(4-amino-3-(4-(2-fluoro-3-methoxyphenoxy)phenyl)-1H-pyrazolo[3,4-d]pyrimidin-1-yl)cyclohexyl 4-nitrobenzoate (80 mg, 0.13 mmol), LiOH (13 mg, 0.54 mmol) and 5 mL MeOH. The mixture was reacted for 3 hour at room temperature. TLC and LCMS showed that the reaction was completed. The reaction system was added with 5 mL H$_2$O and extracted with DCM (5 mL×3). The combined organic phase was dried with anhydrous sodium sulfate. After filtration and concentration, the residue was purified with silica gel column (DCM:MeOH=100:1~ 100:2) to afford 50 mg product, yield 83%.

$^1$H NMR (400 MHz, CDCl$_3$): δ 8.29 (s, 1H), 7.57 (d, J=8.5 Hz, 2H), 7.05 (d, J=8.5 Hz, 2H), 6.99 (td, J=8.4, 2.0 Hz, 1H), 6.76 (t, J=7.9 Hz, 1H), 6.66 (dd, J=8.2, 7.0 Hz, 1H), 5.52 (brs, 2H), 4.76-4.70 (m, 1H), 4.07-4.05 (m, 1H), 3.86 (s, 3H), 2.45 (qd, J=12.8, 3.5 Hz, 2H), 1.94 (d, J=9.8 Hz, 2H), 1.81-1.76 (m, 2H), 1.74-1.68 (m, 2H).

MS ESI: m/z=450, [M+H]$^+$.

Example 22

3-(4-amino-3-(4-(2-fluoro-3-methoxyphenoxy)phenyl)-1H-pyrazolo[3,4-d]pyrimidin-1-yl)cyclopentane-1-ol

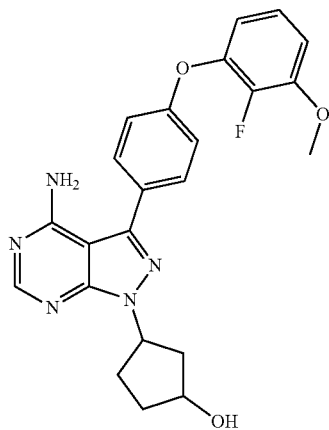 [SMILES: COc1cccc(Oc2ccc(-c3nn(C4CCC(O)C4)c4ncnc(N)c34)cc2)c1F]

Step 1: 3-(4-amino-3-iodo-1H-pyrazolo[3,4-d]pyrimidin-1-yl)cyclopentane-1-ol

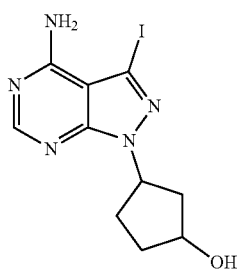 [SMILES: Nc1ncnc2c1c(I)nn2C1CCC(O)C1]

To a dried 500 mL two-necked-flask was added 3-iodo-1H-pyrazolo[3,4-d]pyrimidin-4-amine (5.00 g, 19.16 mmol), 1,3-cyclopentanediol (mixture of cis and trans) (3.91 g, 38.10 mmol), PPh₃ (10.05 g, 38.31 mmol) and 200 mL ultra dry THF under Ar. The flask was cooled in dry ice-ethanol bath. Then, diisopropyl azodicarboxylate (7.75 g, 38.31 mmol) was added dropwise into the mixture and reacted for 5 hours. LCMS showed that the reaction was completed. The resulting solution was filtrated to obtain 3.80 g light yellow solid. The filtrate was concentrated and purified with silica gel column (DCM:MeOH=100:1~100:2) to afford 200 mg product, total yield 60%.

MS ESI: m/z=346, [M+H]⁺.

Step 2: 3-(4-amino-3-(4-(2-fluoro-3-methoxyphenoxy)phenyl)-1H-pyrazolo[3,4-d]pyrimidin-1-yl)cyclopentane-1-ol

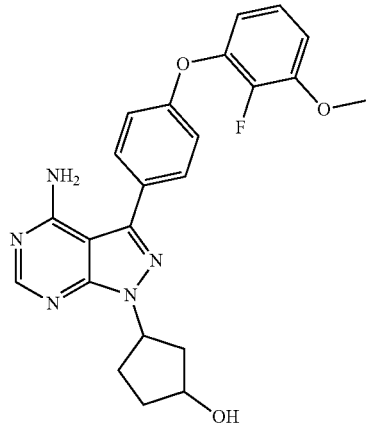

To a 50 mL two-necked-flask was added 3-(4-amino-3-iodo-1H-pyrazolo[3,4-d]pyrimidin-1-yl)cyclopentane-1-ol (0.25 g, 0.72 mmol), 2-(4-(2-fluoro-3-methoxyphenoxy)phenyl)-4,4,5,5-tetramethyl-1,3,2-dioxaborane (0.32 g, 0.94 mmol), potassium carbonate (0.30 g, 2.17 mmol), tetratriphenylphosphine palladium (0.17 g, 0.15 mmol), 20 mL 1,4-dioxane and 10 mL H₂O. The resulting solution was heated to reflux to react for an hour. LCMS showed that the reaction was completed. After cooled to room temperature, the reaction system was added with 10 mL H₂O and extracted with DCM (10 mL×3). The combined organic phase was washed with brine (10 mL×3) and dried with anhydrous sodium sulfate. After filtration and concentration, the residue was purified with silica gel column (DCM:MeOH=100:1) to afford 200 mg product, yield 63%.

¹H NMR (400 MHz, CDCl₃): δ 8.38 (s, 1H), 7.62 (d, J=8.8 Hz, 2H), 7.12 (d, J=8.6 Hz, 2H), 7.08 (td, J=8.4, 2.1 Hz, 1H), 6.84 (ddd, J=8.3, 6.9, 1.4 Hz, 1H), 6.74 (ddd, J=8.3, 6.9, 1.4 Hz, 1H), 5.75 (d, J=10.2 Hz, 1H), 5.55 (brs, 2H), 5.46 (dd, J=14.2, 8.4 Hz, 1H), 4.46-4.45 (m, 1H), 3.94 (s, 3H), 2.50-2.35 (m, 2H), 2.32-2.23 (m, 1H), 2.24-2.17 (m, 1H), 2.10-2.01 (m, 1H), 1.94-1.78 (m, 1H).

¹⁹F NMR (376 MHz, CDCl₃): δ −152.82 (s).

MS ESI: m/z=436, [M+H]⁺.

Example 23

(±) trans-3-(4-amino-3-(4-(2-fluoro-3-methoxyphenoxy)phenyl)-1Hpyrazolo[3,4-d]pyrimidin-1-yl)cyclopentane-1-ol

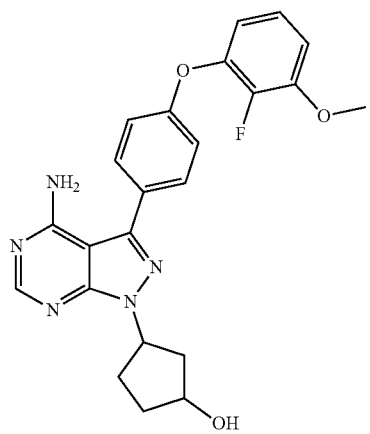 [SMILES: COc1cccc(Oc2ccc(-c3nn(C4CCC(O)C4)c4ncnc(N)c34)cc2)c1F]

Step 1: 3-(4-amino-3-(4-(2-fluoro-3-methoxyphenoxy)phenyl)-1H-pyrazolo[3,4-d]pyrimidin-1-yl)cyclopentyl 4-nitrobenzoate

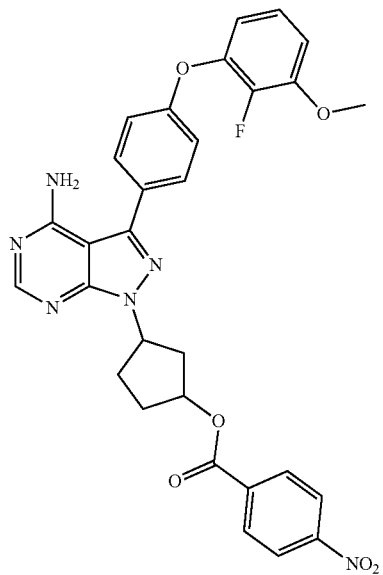 [SMILES: COc1cccc(Oc2ccc(-c3nn(C4CCC(OC(=O)c5ccc([N+](=O)[O-])cc5)C4)c4ncnc(N)c34)cc2)c1F]

To a dried 25 mL two-necked-flask was added (±) cis-3-(4-amino-3-(4-(2-fluoro-3-methoxyphenoxy)phenyl)-1H-pyrazolo[3,4-d]pyrimidin-1-yl)cyclopentane-1-ol (50 mg, 0.12 mmol), 4-nitrobenzoic acid (38 mg, 0.23 mmol), triphenylphosphine (60 mg, 0.23 mmol) and 5 mL ultra dry THF. The flask was cooled in ice-ethanol bath, and diisopropyl azodicarboxylate (46 mg, 0.23 mmol) was added dropwise into the mixture. 3 hours later, LCMS showed that the reaction was completed. The reaction system was mixed with 5 mL H₂O and extracted with DCM (5 mL×3). The combined organic phase was dried with anhydrous sodium sulfate. After filtration and concentration, the residue was purified with silica gel column (DCM:MeOH=100:1) to afford 56 mg product, yield 80%.
MS ESI: m/z=585, [M+H]⁺.

Step 2: (±) trans-3-(4-amino-3-(4-(2-fluoro-3-methoxyphenoxy)phenyl)-1H-pyrazolo[3,4-d]pyrimidin-1-yl)cyclopentane-1-ol

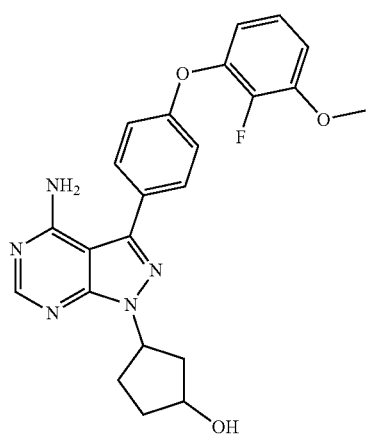 [SMILES: COc1cccc(Oc2ccc(-c3nn(C4CCC(O)C4)c4ncnc(N)c34)cc2)c1F]

To a 25 mL flask was added 3-(4-amino-3-(4-(2-fluoro-3-methoxyphenoxy)phenyl)-1H pyrazolo[3,4-d]pyrimidin-1-yl)cyclopentyl 4-nitrobenzoate (56 mg, 0.10 mmol), LiOH (7 mg, 0.29 mmol) and 3 mL MeOH. The mixture was reacted for 3 hour at room temperature. TLC and LCMS showed that the reaction was completed, and 3 mL H₂O was added and extracted with DCM (3 mL×3). The combined organic phase was dried with anhydrous sodium sulfate. After filtration and concentration, the residue was purified with silica gel column (DCM:MeOH=100:1~ 100:2) to afford 30 mg product, yield 90%.
¹H NMR (400 MHz, CDCl₃): δ 8.34 (s, 1H), 7.62 (d, J=8.6 Hz, 2H), 7.12 (d, J=8.6 Hz, 2H), 7.07 (td, J=8.4, 2.0 Hz, 1H), 6.84 (t, J=7.4 Hz, 1H), 6.74 (t, J=7.6 Hz, 1H), 5.82 (brs, 2H), 5.65-5.57 (m, 1H), 4.76-4.63 (m, 1H), 3.94 (s, 3H), 2.56-2.09 (m, 6H).
¹⁹F NMR (376 MHz, CDCl₃): δ −152.83 (s).
MS ESI: m/z=436, [M+H]⁺.

Example 24

5-(4-amino-3-(4-phenoxyphenyl)-1H-pyrazolo[3,4-d]pyrimidin-1-yl)tetrahydro-2H-pyran-3,4-diol

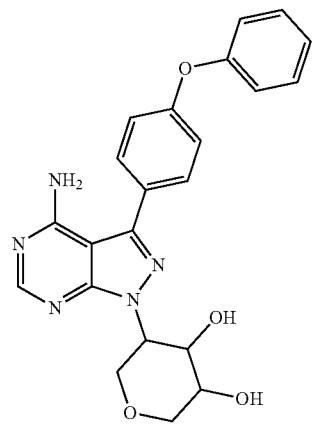 [SMILES: Nc1ncnc2c1c(-c1ccc(Oc3ccccc3)cc1)nn2C1COCC(O)C1O]

Step 1: 2-(allyloxy)acetaldehyde

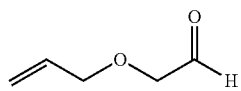

To a dried 100 mL flask was added 3-(allyloxy)propane-1,2-diol (1.00 g, 7.57 mmol), 30 mL DCM and 15 mL H₂O. The resulting solution was mixed with sodium periodate (1.94 g, 9.08 mmol) and stirred at room temperature. TLC showed that the reaction was completed. The mixture was added with 20 mL H₂O and then separated and extracted with DCM (50 mL×3). The combined organic phase was dried with anhydrous sodium sulfate. After filtration and concentration, the residue was used directly in the next step.

Step 2: 1-(allyloxy)butyl-3-ene-2-ol

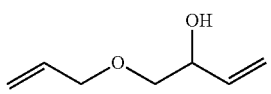

To a dried 2000 mL three-necked-flask was added 2-(allyloxy)acetaldehyde (15.00 g, crude product) and 1000 mL ultra dry THF, and cooled in ice-ethanol bath. THF solution of vinyl magnesium bromide (1 M, 179.78 mL, 179.78 mmol) was added within an hour. The reacting solution was continued to stir for 4 h. TLC showed that the reaction was completed. The reaction system was quenched with 100 mL H$_2$O and most THF was removed. The resulting solution was mixed with 300 mL DCM and 100 mL H$_2$O and separated, and extracted with DCM (150 mL×3). The combined organic phase was dried with anhydrous sodium sulfate. After filtration and concentration, the residue was purified with silica gel column (petroleum ether:ethyl acetate=7:3) to afford 7.20 g, yield 35%.

$^1$H NMR (400 MHz, CDCl$_3$): δ 5.99-5.74 (m, 2H), 5.41-5.24 (m, 2H), 5.20 (dd, J=10.7, 1.3 Hz, 2H), 4.39-4.27 (m, 1H), 4.04 (dt, J=5.7, 1.3 Hz, 2H), 3.51 (dd, J=9.7, 3.4 Hz, 1H), 3.34 (dd, J=9.6, 8.0 Hz, 1H), 2.49 (d, J=3.4 Hz, 1H).

Step 3: 3,6-dihydro-2H-pyran-3-ol

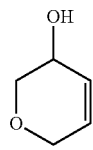

To a dried 500 mL three-necked-flask was added 1-(allyloxy)butan-3-en-2-ol (7.20 g, 56.18 mmol), 350 mL ultra dry DCM and second generation Grubbs catalyst (1.19 g, 1.40 mmol) under Ar. The mixture was reacted for 9 h at room temperature. TLC showed that the reaction was completed. The reacting solution was purified with silica gel column (petroleum ether:ethyl acetate=4:1) to afford 5.00 g product, yield 90%.

$^1$H NMR (400 MHz, CDCl$_3$): δ 6.04-5.96 (m, 1H), 5.96-5.90 (m, 1H), 4.28-4.04 (m, 2H), 3.98 (dd, J=5.5, 2.5 Hz, 1H), 3.85 (ddd, J=11.8, 2.8, 0.7 Hz, 1H), 3.75 (dd, J=11.8, 3.0 Hz, 1H), 1.97 (d, J=9.3 Hz, 1H).

Step 4: 1-(3,6-dihydro-2 h-pyran-3-yl)-3-(4-phenoxyphenyl)-1H-pyrazolo[3,4-d]pyrimidin-4-amine

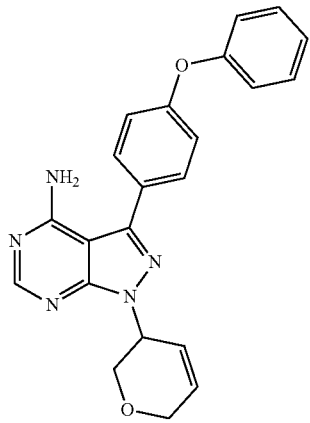 [SMILES: Nc1ncnc2c1c(-c1ccc(Oc3ccccc3)cc1)nn2C1C=CCOC1]

To a dried 25 mL two-necked-flask was added 3,6-dihydro-2H-pyran-3-ol (0.14 g, 1.40 mmol), 3-(4-phenoxyphenyl)-1H-pyrazolo[3,4-d]pyrimidin-4-amine (0.42 g, 1.40 mmol), PPh$_3$ (0.73 g, 2.80 mmol) and 10 mL ultra dry THF. The flask was cooled in dry-ice and ethanol bath, and diisopropyl azodicarboxylate (0.57 g, 2.80 mmol) was added into the mixture. After reacted for 1 hour, LCMS showed that the reaction was completed. The resulting solution was mixed with 10 mL H$_2$O and extracted with DCM (20 mL×3). The combined organic phase and washed with brine (30 mL×1) and dried with anhydrous sodium sulfate. After filtration and concentration, the residue was purified with silica gel column (DCM:MeOH=40:1) to afford 50 mg, yield 95%.

$^1$H NMR (400 MHz, CDCl$_3$): δ 8.39 (s, 1H), 7.64 (d, J=8.7 Hz, 2H), 7.39 (dd, J=8.5, 7.5 Hz, 2H), 7.22-7.10 (m, 3H), 7.09-7.04 (m, 2H), 6.13 (ddd, J=10.4, 4.8, 2.2 Hz, 1H), 6.05 (dd, J=10.4, 2.1 Hz, 1H), 5.63 (ddd, J=10.1, 5.1, 2.5 Hz, 1H), 5.52 (brs, 2H), 4.36 (ddd, J=16.8, 5.2, 2.4 Hz, 1H), 4.29-4.15 (m, 2H), 4.08 (dd, J=11.0, 7.4 Hz, 1H).

MS ESI: m/z=386, [M+H]$^+$.

Step 5: 5-(4-amino-3-(4-phenoxyphenyl)-1H-pyrazolo[3,4-d]pyrimidin-1-yl)tetrahydro-2 h-pyran-3,4-diol

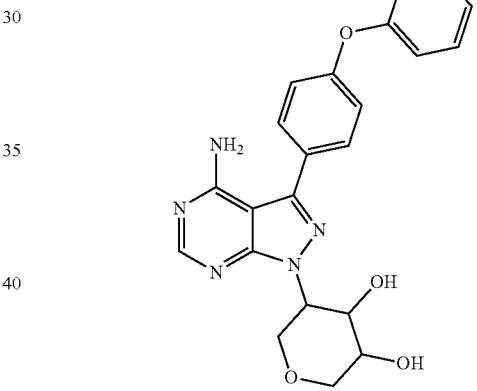

To a 25 mL two-necked-flask was added 5 mL deionized water, 5 mL tert butyl alcohol, K$_3$Fe(CN)$_6$ (0.13 g, 0.39 mmol), K$_2$CO$_3$ (54 mg, 0.39 mmol), K$_2$OsO$_2$(OH)$_4$ (24 mg, 0.07 mmol) and 1-(3,6-dihydro-2H-pyran-3-yl)-3-(4-phenoxyphenyl)-1H-pyrazo[3,4-d]pyrimidin-4-amine (50 mg, 0.13 mmol). The mixture was stirred vigorously. After reacted for 4 hours, LCMS showed that the reaction was completed. The reaction system was mixed with 10 mL EtOAc. After filtration, 15 mL H$_2$O was added into the filtrate and separated. The resulting solution was extracted with EtOAc (15 mL×2). The combined organic phase was dried with anhydrous sodium sulfate. After filtration and concentration, the residue was purified with silica gel column (DCM:MeOH=20:1) to afford 18 mg product, yield 36%.

$^1$H NMR (400 MHz, DMSO-d$_6$): δ 8.24 (s, 1H), 7.66 (d, J=8.7 Hz, 2H), 7.51-7.37 (m, 2H), 7.15 (ddd, J=11.1, 9.7, 4.2 Hz, 5H), 5.00 (td, J=10.6, 4.8 Hz, 1H), 4.90 (d, J=3.8 Hz, 1H), 4.85 (d, J=6.6 Hz, 1H), 4.33-4.20 (m, 1H), 3.86 (d, J=8.5 Hz, 3H), 3.65 (t, J=11.0 Hz, 1H), 3.57 (d, J=11.8 Hz, 1H).

MS ESI: m/z=420, [M+H]$^+$.

Example 25

3-(4-amino-3-(4-(3-fluorophenoxy) phenyl)-1H-pyrazolo[3,4-d]pyrimidin-1-yl) cyclopentane-1-ol

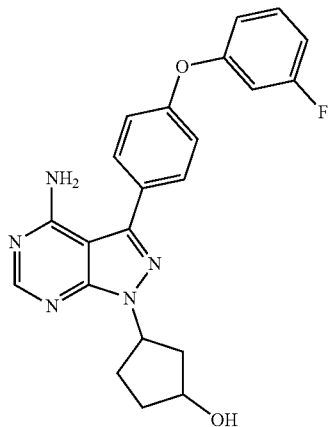 [SMILES: Nc1ncnc2c1c(-c1ccc(Oc3cccc(F)c3)cc1)nn2C1CCC(O)C1]

To a 25 mL two-necked-flask was added successively 3-(4-amino-3-iodo-1H-pyrazolo[3,4-d]pyrimidin-1-yl)cyclopentane-1-ol (0.50 g, 1.45 mmol), (4-(3-fluorophenoxy)phenyl)boric acid (0.40 g, 1.74 mmol), potassium phosphate (0.92 g, 4.35 mmol), tetratriphenylphosphine palladium (72 mg, 0.22 mmol), 10 mL 1,4-dioxane and 5 mL H$_2$O under the protection of Ar. The mixture was heated to reflux for an hour. LCMS showed that the reaction was completed. The reaction system was mixed with 10 mL H$_2$O and extracted with DCM (10 mL×3). The combined organic phase was dried with anhydrous sodium sulfate. After filtration and concentration, the residue was purified with silica gel column (DCM:MeOH=100:1) to afford 360 mg product, yield 62%.

$^1$H NMR (400 MHz, CDCl$_3$): δ 8.39 (s, 1H), 7.68 (d, J=8.7 Hz, 2H), 7.33 (td, J=8.3, 6.7 Hz, 1H), 7.21-7.14 (m, 2H), 6.87 (td, J=8.4, 2.4 Hz, 2H), 6.79 (dt, J=10.0, 2.4 Hz, 1H), 5.75 (d, J=10.2 Hz, 1H), 5.56 (s, 2H), 5.47 (ddd, J=16.4, 7.3, 3.1 Hz, 1H), 4.52-4.39 (m, 1H), 2.58-2.35 (m, 2H), 2.32-2.19 (m, 2H), 2.09-2.04 (m, 1H), 1.95-1.82 (m, 1H).

$^{19}$F NMR (376 MHz, CDCl$_3$): δ −110.43 (s).

MS ESI: m/z=406, [M+H]$^+$.

Example 26

Cis-3-(4-amino-3-(4-(2-fluoro-3-methoxyphenoxy)phenyl)-1H-pyrazolo[3,4-d]pyrimidin-1-yl) cyclohex-1-ol

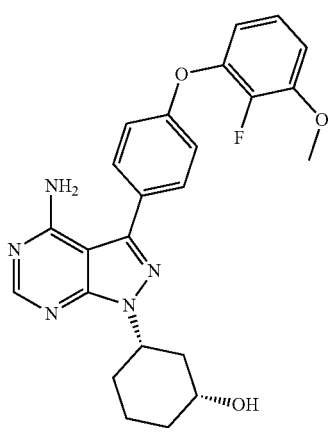 [SMILES: COc1cccc(Oc2ccc(-c3nn([C@H]4CCC[C@@H](O)C4)c4ncnc(N)c34)cc2)c1F]

Step 1: cyclohexyl 3-hydroxyacetate

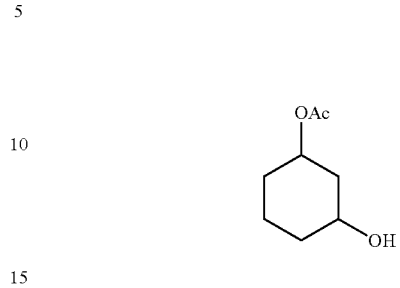

A solution of 4-chlorophenyl acetate (84.2 g, 495 mmol) in anhydrous toluene (800 ml) was exchanged 3 times with N$_2$. Cyclohexane-1,3-diol (38.3 g, 330 mmol) and *Candida antarctica* lipase B (CALB) (7.6 g) were added, and the mixture was further exchanged and stirred at room temperature for 16 h. The resulting solution was filtrated to remove solid, and filtrate was vacuum concentrated, and residue was purified with silica gel column (ethyl acetate:petroleum ether=0-100%) to afford 47.2 g, yield 91%.

$^1$H NMR (400 MHz, CDCl$_3$) 5.14-4.72 (m, 1H), 4.03-3.67 (m, 1H), 2.25-2.20 (m, 1H), 2.02 (s, 3H), 1.91-1.59 (m, 4H), 1.44-1.25 (m, 3H).

Step 2: 3-(3-iodo-4-((triphenylphosphino)amino)-1H-pyrazolo[3,4-d]pyrimidin-1-yl)cyclohexyl acetate

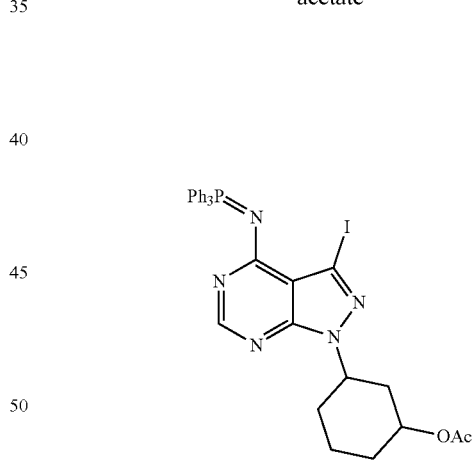

Under the protection of N$_2$, 3-iodo-1H-pyrazolo[3,4-d]pyrimidin-4-amine (22.8 g, 27.5 mmol), cyclohexyl 3-hydroxyacetate (15.2 g, 96.2 mmol) and PPh$_3$ (45.8 g, 174.9 mmol) were dissolved in anhydrous THF (300 mL). Diisopropyl azodicarboxylate (35.3 g, 174.9 mmol) was added dropwise in ice bath. The temperature of system was kept under 10° C. by controlling speed of addition. After addition, the reacting solution was stirred at room temperature for 16 h. The resulting solution was vacuum concentrated, and the residue was purified with silica gel column (ethyl acetate:petroleum ether=0-100%) to afford 35.8 g crude product.

Step 3: 3-(4-amino-3-iodo-1H-pyrazolo[3,4-d]pyrimidin-1-yl) cyclohexyl acetate

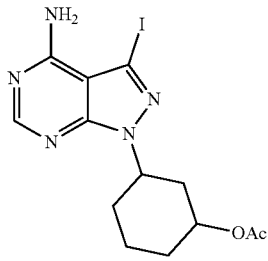 [SMILES: CC(=O)OC1CCCC(n2nc(I)c3c(N)ncnc32)C1]

3-(3-Iodo-4-((triphenylphosphino)amino)-1H-pyrazolo[3,4-d]pyrimidin-1-yl)cyclohexyl acetate (74.1 g, 27.4 mmol) was dissolved in 100 mL acetic acid and mixed with 100 mL water. The mixture was refluxed at 130° C. for 1 h. The solution was concentrated to remove most acetic acid and then diluted with 100 mL H₂O. The resulting solution was extracted with 80 mL DCM for twice. The combined organic phase was dried with anhydrous sodium sulfate. After filtration and concentration, the residue was purified with 100 mL toluene for 3 times to afford 44.5 g crude product.

MS ESI: m/z=402, [M+H]⁺.

Step 4: 3-(4-amino-3-iodo-1h-pyrazolo 3,4-d]pyrimidin-1-yl) cyclohexanol

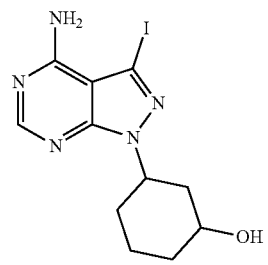 [SMILES: Nc1ncnc2c1c(I)nn2C1CCCC(O)C1]

To a solution of crude (1R)-3-(4-amino-3-iodo-1H-pyrazolo[3,4-d]pyrimidin-1-yl)cyclohexyl acetate (44.5 g, 27.4 mmol) in the mixture of 150 mL methanol and 150 mL THF was added lithium hydroxide monohydrate (13.9 g, 331 mmol). The mixture was stirred at room temperature for 16 h. The resulting solution was suction filtrated to remove solid. The filtrate was concentrated. The residue was purified with silica gel column (DCM:MeOH=1-100%) to afford 8.4 g product, three steps yield 27%.

MS ESI: m/z=360, [M+H]⁺.

Step 5: 3-(4-amino-3-(4-(2-fluoro-3-methoxyphenoxy)phenyl)-1H-pyrazolo[3,4-d]pyrimidin-1-yl) cyclohexanol

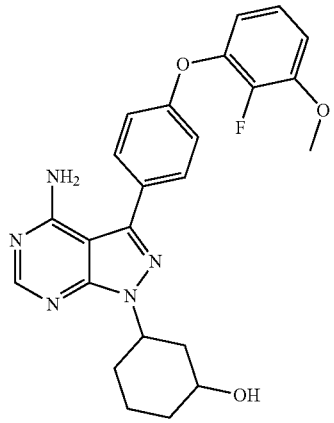 [SMILES: COc1cccc(Oc2ccc(-c3nn(C4CCCC(O)C4)c4ncnc(N)c34)cc2)c1F]

3-(4-amino-3-iodo-1H-pyrazolo[3,4-d]pyrimidin-1-yl) cyclohexanol (8.4 g, 23.4 mmol), 2-(4-(2-fluoro-3-methoxyphenoxy)phenyl)-4,4,5,5-tetramethyl-1,3,2-dioxaborane (9.7 g, 28.8 mmol), tetratriphenylphosphine palladium (2.6 g, 2.3 mmol) and potassium carbonate (8.1 g, 58.5 mmol) were suspended in a mixed solvent of 150 mL 1,4-dioxane and 80 mL H₂O, exchanged 3 times with N₂ and reacted at 120° C. for 16 h. The reaction solution turned clean, and the organic solvent was removed by concentration. The aqueous phase was extracted 3 times with 100 mL DCM. The combined organic phase was dried with anhydrous sodium sulfate. The residue was purified with silica gel column (DCM:MeOH=1-100%) to afford 10.3 g product, yield 81%.

MS ESI: m/z=450, [M+H]⁺.

Step 6: cis-3-(4-amino-3-(4-(2-fluoro-3-methoxyphenoxy)phenyl)-1H-pyrazolin-[3,4-d]pyrimidin-1-yl) cyclohexanol

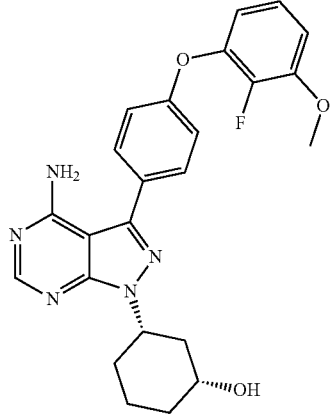 [SMILES: COc1cccc(Oc2ccc(-c3nn([C@H]4CCC[C@@H](O)C4)c4ncnc(N)c34)cc2)c1F]

(1R)-3-(4-amino-3-(4-(2-fluoro-3-methoxyphenoxy)phenyl)-1H-pyrazolo[3,4-d]pyrimidin-1-yl)cyclohexanol (18.1 g, 40 mmol) was purified with Pre-HPLC to afford 9.3 g, yield 51%.

¹H NMR (400 MHz, CDCl₃) δ 8.36 (s, 1H), 7.65-7.61 (m, 2H), 7.13-7.04 (m, 3H), 6.86-6.81 (m, 1H), 6.75-6.71 (m,

1H), 5.29 (brs, 2H), 4.91-4.86 (m, 1H), 3.93 (s, 3H), 3.89-3.84 (m, 1H), 2.35-2.32 (m, 1H), 2.19-2.11 (m, 1H), 2.20-1.91 (m, 4H), 1.50-1.47 (m, 2H).

MS ESI: m/z=450, [M+H]$^+$.

Example 27

3-(4-amino-3-(4-(2-fluoro-3-methoxyphenoxy) phenyl)-1H-pyrazolo[3,4-d]pyrimidin-1-yl)cyclohexane-1,2-diol

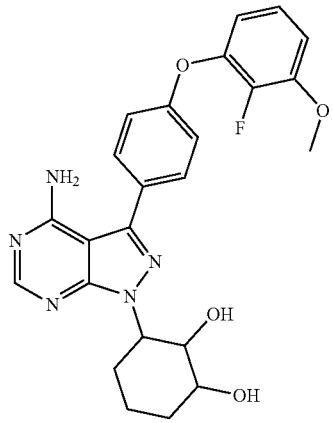 [SMILES: COc1cccc(Oc2ccc(-c3nn(C4CCCC(O)C4O)c4ncnc(N)c34)cc2)c1F]

Step 1: 3-(4-(2-fluoro-3-methoxyphenoxy)phenyl)-1H-pyrazolo[3,4-d]pyrimidin-4-amine

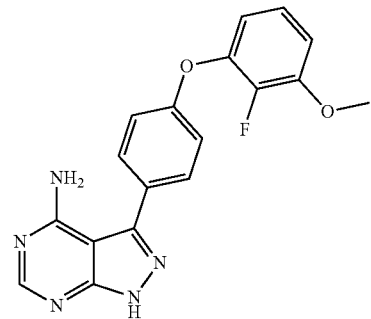 [SMILES: COc1cccc(Oc2ccc(-c3n[nH]c4ncnc(N)c34)cc2)c1F]

3-Iodo-1H-pyrazolo[3,4-d]pyrimidin-4-amine (5.0 g, 19.2 mmol), 2-(4-(2-fluoro-3-methoxyphenoxy)phenyl)-4,4,5,5-tetramethyl-1,3,2-dioxaborane (7.7 g, 23.0 mmol), PdCl$_2$(dppf) (1.4 g, 1.9 mmol) and potassium phosphate (8.1 g, 38.3 mmol) were dispersed in the mixture of 36 mL N,N-dimethylformamide and 18 mL H$_2$O, and exchanged with N$_2$ for three times, and warmed to 120° C. to react for 16 h. The solution was mixed with 50 mL H$_2$O and filtrated, and residue was washed with MeOH (20 mL×1) and dried under reduced pressure to afford 2.5 g product, yield 37%.

MS ESI: m/z=352, [M+H]$^+$.

Step 2: 1-(cyclohex-2-en-1-yl)-3-(4-(2-fluoro-3-methoxyphenoxy)phenyl)-1H-pyrazolo[3,4-d]pyrimidin-4-amine

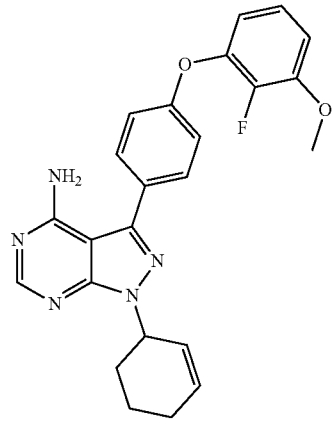 [SMILES: COc1cccc(Oc2ccc(-c3nn(C4C=CCCC4)c4ncnc(N)c34)cc2)c1F]

Under the protection of N$_2$, 3-(4-(2-fluoro-3-methoxyphenoxy)phenyl)-1H-pyrazolo[3,4-d]pyrimidin-4-amine (351 mg, 1 mmol), cyclohex-2-enol (118 mg, 1.2 mmol) and PPh$_3$ (655 mg, 2.5 mmol) were dissolved in anhydrous THF (20 mL). The mixture was added dropwise with diisopropyl azodicarboxylate (606 mg, 3 mmol) in ice bath. The temperature was kept under 10° C. by controlling addition speed. The resulting solution was stirred at room temperature for 16 h. After vacuum concentration, the residue was purified with silica gel column (MeOH:DCM=0-100%) to afford 220 mg product, yield 51%.

MS ESI: m/z=432, [M+H]$^+$.

Step 3: 3-(4-amino-3-(4-(2-fluoro-3-methoxyphenoxy)phenyl)-1H-pyrazolo[3,4-d]pyrimidin-1-yl)cyclohexane-1,2-diol

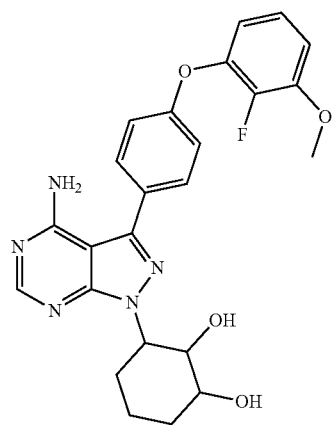 [SMILES: COc1cccc(Oc2ccc(-c3nn(C4CCCC(O)C4O)c4ncnc(N)c34)cc2)c1F]

Under the protection of N$_2$, 1-(cyclohex-2-en-1-yl)-3-(4-(2-fluoro-3-methoxyphenoxy) phenyl)-1H-pyrazolo[3,4-d]pyrimidin-4-amine (200 mg, 0.46 mmol) and N-methylmorpholine-N-oxide (108 mg, 0.92 mmol) were dissolved in the mixture of 10 mL tert butyl alcohol and 5 mL H$_2$O. The mixing solution was mixed with potassium osmate (0.5 mg, 0.0014 mmol) in ice bath. The reacting solution was stirred at room temperature for 16 h and then mixed with 10 mL saturated sulphuric acid and then extracted with EtOAc (10 mL×2). The combined organic phase was dried with anhydrous sodium sulfate. After vacuum concentration, the residue was purified with pre-HPLC to afford 110 mg product, yield 52%.

$^1$H NMR (400 MHz, DMSO-d$_6$): δ 8.19 (s, 1H), 7.64-7.66 (m, 2H), 7.2-7.0 (m, 6H), 4.9-4.87 (m, 1H), 4.60 (s, 1H), 4.45-4.43 (m, 2H), 3.99-3.97 (m, 2H), 3.89 (s, 3H), 1.94-1.90 (m, 1H), 1.81-1.76 (m, 3H), 1.55-1.49 (m, 2H).

MS ESI: m/z=466, [M+H]$^+$.

Example 28

4-(4-amino-3-(4-(2-fluoro-3-methoxyphenoxy)phenyl)-1H-pyrazolo[3,4-d]pyrimidin-1-yl)cyclohexane-1,2-diol

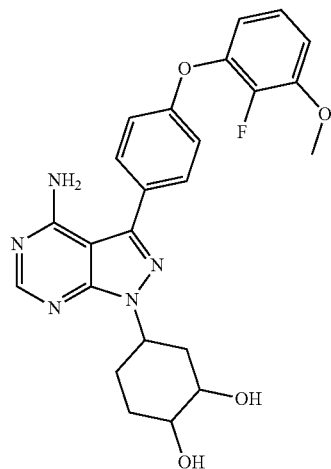 [SMILES: COc1cccc(Oc2ccc(-c3nn(C4CCC(O)C(O)C4)c4ncnc(N)c34)cc2)c1F]

Step 1: 1-(cyclohex-2-en-1-yl)-3-(4-(2-fluoro-3-methoxyphenoxy)phenyl)-1H-pyrazolo[3,4-d]pyrimidin-4-amine

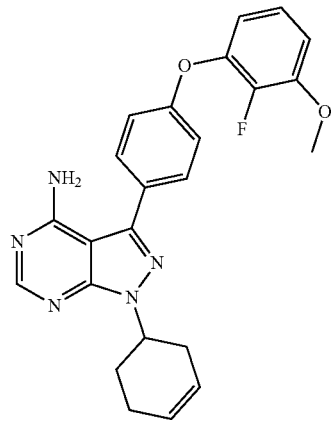 [SMILES: COc1cccc(Oc2ccc(-c3nn(C4CC=CCC4)c4ncnc(N)c34)cc2)c1F]

Under the protection of N$_2$, 3-(4-(2-fluoro-3-methoxyphenoxy)phenyl)-1H-pyrazolo[3,4-d]pyrimidin-4-amine (50 mg, 0.14 mmol), cyclohex-3-enol (17 mg, 0.17 mmol) and PPh$_3$ (74 mg, 0.28 mmol) were dissolved in anhydrous THF (3 mL). The mixture was added dropwise with diisopropyl azodicarboxylate (57 mg, 0.28 mmol) in ice bath. The temperature was kept under 10° C. by controlling addition speed. The resulting solution was stirred at room temperature for 16 h. After vacuum concentration, the residue was purified with silica gel column (MeOH:DCM=0-100%) to afford 30 mg product, yield 50%.

MS ESI: m/z=432, [M+H]$^+$.

Step 2: 4-(4-amino-3-(4-(2-fluoro-3-methoxyphenoxy)phenyl)-1H-pyrazolo[3,4-d]pyrimidin-1-yl)cyclohexane-1,2-diol

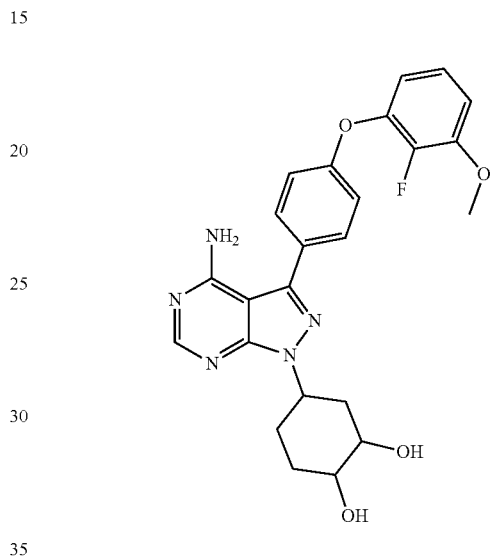

Under the protection of N$_2$, 1-(cyclohex-2-en-1-yl)-3-(4-(2-fluoro-3-methoxyphenoxy)phenyl)-1H pyrazolo[3,4-d]pyrimidin-4-amine (30 mg, 0.070 mmol) and N-methylmorpholine-N-oxide (10 mg, 0.084 mmol) were dissolved in the mixture of 2 mL tert butyl alcohol and 0.5 mL H$_2$O. Potassium osmate (0.5 mg, 0.0014 mmol) was added to the solution in ice bath. The solution was stirred at room temperature for 16 h, 10 mL saturated sulphuric acid was added, and then extracted with EtOAc (10 mL×2). The combined organic phase was dried with anhydrous sodium sulfate. After vacuum concentration, the residue was purified with pre-HPLC to afford 3 mg peak 1 product, yield 9% and 3 mg peak 2 product, yield 9%.

Peak 1:

$^1$H NMR (400 MHz, CDCl$_3$) δ 8.38 (s, 1H), 7.65-7.61 (m, 2H), 7.14-7.11 (m, 2H), 7.09-7.05 (m, 1H), 6.86-6.82 (m, 1H), 6.76-6.72 (m, 1H), 5.52 (s, 2H), 5.14-4.97 (m, 1H), 4.44 (brs, 1H), 3.96-3.94 (m, 4H), 3.86-3.80 (m, 1H), 2.67-2.61 (m, 1H) 2.57-2.48 (m, 1H), 2.25-2.19 (m, 2H), 1.94-1.84 (m, 2H), 1.73-1.66 (m, 1H).

MS ESI: m/z=466, [M+H]$^+$.

Peak 2:

$^1$H NMR (400 MHz, CDCl$_3$) δ 8.37 (s, 1H), 7.64-7.60 (m, 2H), 7.14-7.10 (m, 2H), 7.08-7.04 (m, 1H), 6.86-6.82 (m, 1H), 6.76-6.71 (m, 1H), 5.39 (s, 2H), 5.26-5.20 (m, 1H), 4.22 (brs, 1H), 3.99 (m, 3H), 3.87-3.84 (m, 1H), 2.42-2.36 (m, 1H), 2.31-2.35 (m, 2H), 2.17-2.06 (m, 2H), 1.96-1.88 (m, 2H).

MS ESI: m/z=466, [M+H]$^+$.

Example 29 (Reference Compound)

1-cyclohexyl-3-(4-(2-fluoro-3-methoxyphenoxy)phenyl)-1H-pyrazolo[3,4-d]pyrimidin-4-amine

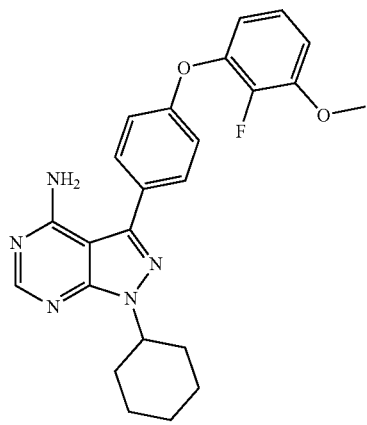 [SMILES: COc1cccc(Oc2ccc(-c3nn(C4CCCCC4)c4ncnc(N)c34)cc2)c1F]

Step 1: 1-cyclohexyl-3-(4-(2-fluoro-3-methoxyphenoxy)phenyl)-1H-pyrazolo[3,4-d]pyrimidin-4-amine

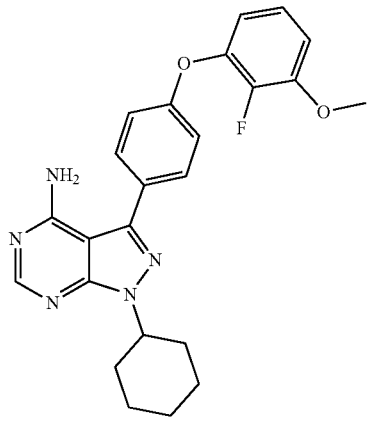 [SMILES: COc1cccc(Oc2ccc(-c3nn(C4CCCCC4)c4ncnc(N)c34)cc2)c1F]

To a solution of 1-(cyclohex-2-en-1-yl)-3-(4-(2-fluoro-3-methoxyphenoxy)phenyl)-1H-pyrazolo[3,4-d]pyrimidin-4-amine (190 mg, 0.44 mmol) in 20 mL MeOH was added 10% wet Pd/C (20 mg). The mixture was exchanged 3 times with H₂ (15 psi) and then reacted overnight at room temperature. The resulting solution was filtrated with diatomite. The filtrate was concentrated. The residue was purified with pre-HPLC to afford 130 mg product, yield 68%.

¹H NMR (400 MHz, CDCl₃) δ 8.37 (s, 1H), 7.65-7.63 (m, 2H), 7.14-7.06 (m, 2H), 7.04 (m, 1H), 6.85-6.81 (m, 1H), 6.75-6.70 (m, 1H), 5.43 (s, 2H), 4.78-7.75 (m, 1H), 3.99 (s, 3H), 2.11-2.02 (m, 4H), 1.95-1.91 (m, 2H), 1.77-1.74 (m, 1H), 1.54-1.49 (m, 2H), 1.34-1.31 (m, 1H).

MS ESI: m/z=434, [M+H]⁺.

Example 30

(5-(4-amino-3-(4-(2-fluoro-3-methoxyphenoxy)phenyl)-1H-pyrazolo[3,4-d]pyrimidin-1-yl)tetrahydro-2h-pyran-2-yl)methanol

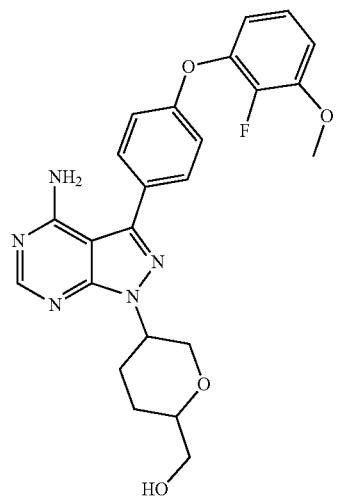 [SMILES: COc1cccc(Oc2ccc(-c3nn(C4CCC(CO)OC4)c4ncnc(N)c34)cc2)c1F]

Step 1: tert-butyl ((3,4-dihydro-2H-pyran-2-yl)methoxy)diphenylsilane

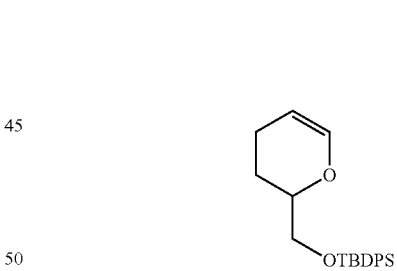

To a solution of (3,4-dihydro-2H-pyran-2-yl)methanol (1.0 g, 8.7 mmol) in dichloromethane (20 mL) was added successively tert-butyl diphenylchlorosilane (3.35 g, 12.2 mmol) and imidazole (1.43 g, 20.3 mmol), and stirred overnight at room temperature. 50 mL DCM was added to the solution, and washed with H₂O (100 mL×1). The organic phase was dried with anhydrous sodium sulfate. After filtration and concentration, the residue was purified with silica gel column (ethyl acetate:petroleum ether=0-100%) to afford 2.3 g product, yield 75%.

¹H NMR (400 MHz, CDCl₃): δ 7.71-7.68 (m, 4H), 7.45-7.37 (m, 6H), 6.37-6.35 (d, J=8 Hz, 1H), 4.68-4.65 (m, 1H), 3.96-3.93 (m, 1H), 3.83-3.77 (m, 1H), 3.71-3.67 (m, 1H), 2.08-2.00 (m, 1H), 1.99-1.92 (m, 2H), 1.74-1.71 (m, 1H), 1.02 (s, 9H).

Step 2: 6-((tert-butyl diphenylsilyl)oxy)methyl)tetrahydro-2H-pyran-3-ol

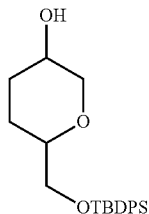

Under nitrogen protection, tert-butyl((3,4-dihydro-2H-pyran-2-yl)methoxy)diphenylsilane (1.3 g, 3.7 mmol) was added to tetrahydrofuran (20 mL). After cooled to −78° C., borane dimethyl sulfide complex (1.8 mL, 10 M, 18.0 mmol) was added dropwise to the solution. The resulting solution was naturally warmed to room temperature and stirred overnight. 1N Sodium hydroxide aqueous solution was slowly added dropwise to the system until no borane gas was released, then 30% hydrogen peroxide (5 mL) was added, and the reaction solution was stirred at 45° C. for 2 hours. The reacting solution was mixed with 50 mL $H_2O$ and then extracted with EtOAc (50 mL×1). The organic phase was dried with anhydrous sodium sulfate. After filtration and vacuum concentration, the residue was purified with reversed phase column chromatography (acetonitrile:$H_2O$=5-95%) to afford 1.0 g product, yield 73%.

Step 3: 1-(6-((tert-butyl diphenylsilyl)oxy)methyl) tetrahydro-2H-pyran-3-yl)-3-iodo-1H-pyrazolo[3,4-d]pyrimidin-4-amine

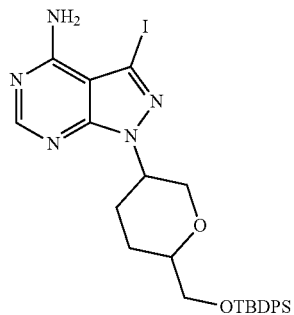

3-Iodo-1H-pyrazolo[3,4-d]pyrimidin-4-amine (0.3 g, 1.15 mmol) was added to THF (20 mL). Under nitrogen protection, 6-((tert butyl diphenylsilyl)oxy)methyl)tetrahydro-2H-pyran-3-ol (555 mg, 1.50 mmol) and $PPh_3$ (753 mg, 2.87 mmol) were added. Diisopropyl azodicarboxylate (697 mg, 3.45 mmol) was added dropwise to the solution at 0° C. The resulting solution was stirred overnight at room temperature and concentrated under reduced pressure. The residue was purified with reversed phase column chromatography (acetonitrile:$H_2O$=5-95%) to afford 330 mg product, yield 47%.
MS ESI: m/z=614, [M+H]$^+$.

Step 4: 1-(6-((tert-butyl diphenylsilyl)oxy)methyl) tetrahydro-2H-pyran-3-yl)-3-(4-(2-fluoro-3-methoxyphenoxy)phenyl)-1H-pyrazolo[3,4-d]pyrimidin-4-amine

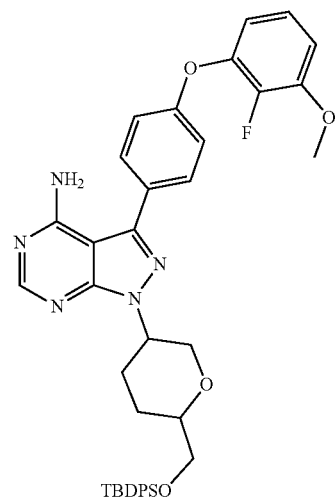

1-(6-((Tert-butyl diphenylsilyl)oxy)methyl)tetrahydro-2H-pyran-3-yl)-3-iodo-1H-pyrazolo[3,4-d]pyrimidin-4-amine (16.4 g, 26.8 mmol) was added into the mixed solvent of 1,4-dioxane (160 mL) and $H_2O$ (40 mL). 2-(4-(2-fluoro-3-methoxyphenoxy)phenyl)-4,4,5,5-tetramethyl-1,3,2-dioxaborane (8.95 g, 26.8 mmol) and potassium carbonate (11.1 g, 80.4 mmol) were added into the reaction system. Tetra (triphenylphosphine)palladium (1.55 g, 1.34 mmol) was added into the reacting solution under the protection of $N_2$. The resulting solution was stirred overnight at 100° C. After concentration, the residue was purified with column chromatography (MeOH:DCM=0-100%) to afford 1.4 g peak 1 product, yield 7% and 1.0 g peak 2 product, yield 5%.

Peak 1:
$^1$H NMR (400 MHz, CDCl$_3$): δ 8.34 (s, 1H), 7.68-7.65 (m, 4H), 7.62-7.60 (m, 2H), 7.41-7.32 (m, 6H), 7.11-7.09 (m, 2H), 7.07-7.04 (m, 1H), 6.86-6.82 (m, 1H), 6.76-6.72 (m, 1H), 5.57 (brs, 2H), 4.83-4.82 (m, 1H), 4.49-4.45 (m, 1H), 3.94 (s, 3H), 3.87-3.82 (m, 2H), 3.71-3.69 (m, 2H), 2.62-2.57 (m, 1H), 2.28-2.22 (m, 1H), 2.14-2.08 (m, 1H), 1.82 (m, 1H), 1.03 (s, 9H).
MS ESI: m/z=704, [M+H]$^+$.

Peak 2:
$^1$H NMR (400 MHz, CDCl$_3$): δ 8.36 (s, 1H), 7.71-7.68 (m, 4H), 7.64-7.61 (m, 2H), 7.44-7.37 (m, 6H), 7.14-7.12 (m, 2H), 7.09-7.04 (m, 1H), 6.86-6.81 (m, 1H), 6.76-6.72 (m, 1H), 5.51 (brs, 2H), 4.97-4.92 (m, 1H), 4.16-4.11 (m, 1H), 4.00-3.94 (m, 1H), 3.93 (s, 3H), 3.81-3.77 (m, 1H), 3.66-3.60 (m, 2H), 2.46-2.36 (m, 1H), 2.26-2.23 (m, 1H), 1.95 (m, 1H), 1.70-1.60 (m, 1H), 1.07 (s, 9H).
MS ESI: m/z=704, [M+H]$^+$.

Step 5: (5-(4-amino-3-(4-(2-fluoro-3-methoxyphenoxy)phenyl)-1H-pyrazolo[3,4-d]pyrimidin-1-yl)tetrahydro-2H-pyran-2-yl)methanol

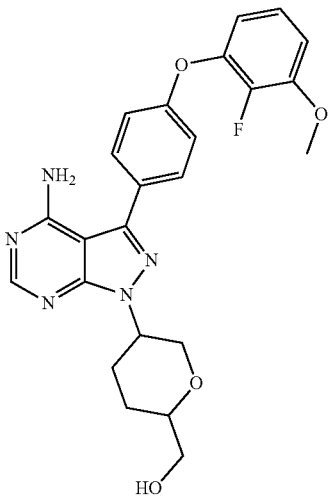 [SMILES: COc1cccc(Oc2ccc(-c3nn(C4CCC(CO)OC4)c4ncnc(N)c34)cc2)c1F]

1-(6-((Tert-butyl diphenylsilyl)oxy)methyl)tetrahydro-2H-pyran-3-yl)-3-(4-(2-fluoro-3-methoxyphenoxy)phenyl)-1H-pyrazolo[3,4-d]pyrimidin-4-amine (peak 1) (1.4 g, 2.0 mmol) was added into THF (20 mL), then was added the THF solution of tetrabutylammonium fluoride (2.6 mL, 1M, 2.6 mmol). The mixture was stirred overnight at room temperature. The resulting solution was concentrated under reduced pressure. The residue was purified with reversed phase column chromatography (acetonitrile:H$_2$O=5-95%) and then purified with chiral SFC to afford 400 mg Peak 1-1 product, yield 43% and 400 mg Peak 1-2, yield 43%.

Peak 1-1:
$^1$H NMR (400 MHz, CDCl$_3$): δ 8.35 (s, 1H), 7.65-7.63 (m, 2H), 7.13-7.05 (m, 3H), 6.86-6.82 (m, 1H), 6.77-6.72 (m, 1H), 5.73 (s, 2H), 4.89 (s, 1H), 4.57-4.54 (m, 1H), 3.97-3.93 (m, 1H), 3.93 (s, 3H), 3.74-3.66 (m, 3H), 2.61-2.56 (m, 1H), 2.33-2.30 (m, 1H), 2.20-2.00 (m, 1H), 1.57-1.59 (m, 1H).
MS ESI: m/z=466, [M+H]$^+$.

Peak 1-2:
$^1$H NMR (400 MHz, CDCl$_3$): δ 8.37 (s, 1H), 7.65-7.63 (m, 2H), 7.13-7.05 (m, 3H), 6.86-6.82 (m, 1H), 6.77-6.72 (m, 1H), 5.73 (s, 2H), 4.89 (s, 1H), 4.57-4.54 (m, 1H), 3.97-3.93 (m, 1H), 3.93 (s, 3H), 3.74-3.66 (m, 3H), 2.61-2.56 (m, 1H), 2.33-2.30 (m, 1H), 2.20-2.00 (m, 1H), 1.57-1.59 (m, 1H).
MS ESI: m/z=466, [M+H]$^+$.

1-(6-((T-butyldiphenylsilyl)oxy)methyl)tetrahydro-2H-pyran-3-yl)-3-(4-(2-fluoro-3-methoxyphenoxy)phenyl)-1H-pyrazolo[3,4-d]pyrimidin-4-amine peak 2 (1.0 g, 1.4 mmol) was added to THF (20 mL), and THF solution of tetrabutylammonium fluoride (1.8 mL, 1M, 1.8 mmol) was added. The mixture was stirred overnight at room temperature. The resulting solution was concentrated under reduced pressure. The residue was purified with reversed phase column chromatography (acetonitrile:H$_2$O=5-95%) and then purified with chiral SFC to afford 200 mg Peak 2-1 product, yield 30% and 200 mg Peak 2-2, yield 30%.

Peak 2-1
$^1$H NMR (400 MHz, CDCl$_3$): δ 8.35 (s, 1H), 7.63-7.60 (m, 2H), 7.14-7.05 (m, 3H), 6.87-6.83 (m, 1H), 6.74-6.72 (m, 1H), 5.74 (s, 2H), 4.89-4.63 (m, 1H), 4.20-4.16 (m, 1H), 4.03-3.97 (m, 1H), 3.97 (s, 3H), 3.71-3.58 (m, 3H), 2.46-2.42 (m, 1H), 2.27-2.24 (m, 1H), 1.83-1.80 (m, 1H), 1.73-1.72 (m, 1H).
MS ESI: m/z=466, [M+H]$^+$.

Peak 2-2:
$^1$H NMR (400 MHz, CDCl$_3$): δ 8.35 (s, 1H), 7.63-7.60 (m, 2H), 7.14-7.05 (m, 3H), 6.87-6.83 (m, 1H), 6.74-6.72 (m, 1H), 5.74 (s, 2H), 4.89-4.63 (m, 1H), 4.20-4.16 (m, 1H), 4.03-3.97 (m, 1H), 3.97 (s, 3H), 3.71-3.58 (m, 3H), 2.46-2.42 (m, 1H), 2.27-2.24 (m, 1H), 1.83-1.80 (m, 1H), 1.73-1.72 (m, 1H).
MS ESI: m/z=466, [M+H]$^+$.

Example 31

(1R,3R)-3-(4-amino-3-(4-(2-fluoro-3-(methoxy-d3)phenoxy)phenyl)-1H-pyrazolo[3,4-d]pyrimidin-1-yl)cyclohexanol

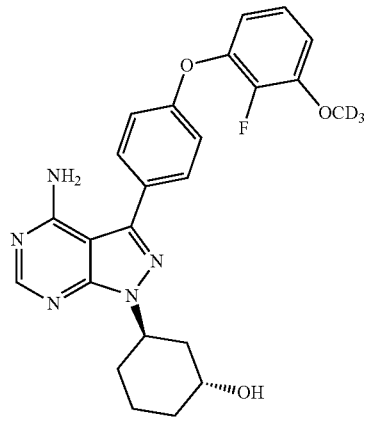

Step 1: 1-fluoro-2-(methoxy-d3)benzene

2-Fluorophenol (2.0 g, 17.9 mmol), PPh$_3$ (7.2 g, 35.8 mmol) and deuterated methanol-d4 (946 mg, 26.8 mmol) in anhydrous THF (20 mL) was added dropwise diisopropyl azodicarboxylate (7.2 g, 35.8 mmol) under N$_2$. The mixture was reacted overnight at room temperature. The reaction system was concentrated under reduced pressure. The residue was purified with column chromatography (ethyl acetate:petroleum ether=0-100%) to afford 1.1 g product, yield 35%.

$^1$H NMR (400 MHz, CDCl$_3$) δ 7.16-7.04 (m, 2H), 7.03-6.90 (m, 2H).

Step 2: 2-fluoro-3-(methoxy-d3) phenol

Under the protection of $N_2$, 1-fluoro-2-(methoxy-d3) benzene (1.3 g, 10.3 mmol) and pentamethyldiethylenetriamine (2.6 mL, 12.4 mmol) were dissolved in anhydrous THF (15 mL). The reaction system was cooled to −78° C. and then added dropwise with N-butyl lithium in n-hexane (5.0 mL, 2.5M, 12.4 mmol). The mixture was continued to react for 2 h and then added with triisopropyl borate (2.9 mL, 12.4 mmol) at the same temperature. The resulting solution was naturally warmed to room temperature and continued to react for 16 h. Acetic acid (0.9 mL, 10.5 mmol) was used to quench the reaction. After the addition, the flask was cooled in ice bath and 30% $H_2O_2$ (1.6 mL, 2.4 mmol) was added. A large amount of viscous solid was precipitated. The reacting solution was stirred at room temperature for 30 min and then diluted with 20 mL $H_2O$, and extracted with EtOAc (20 mL×2). The combined organic phase was washed with saturated sodium bisulfite solution (30 mL×1) and dried with anhydrous sodium sulfate. After concentration, the residue was purified with column chromatography (petroleum ether:ethyl acetate=0-100%) to afford 636 mg, yield 48%.

$^1$H NMR (400 MHz, CDCl$_3$) δ 7.02-6.96 (m, 1H), 6.71-6.65 (m, 1H), 6.61-6.56 (m, 1H), 5.36 (brs, 1H).

Step 3: 1-(4-bromophenoxy)-2-fluoro-3-(methoxy-d3)benzene

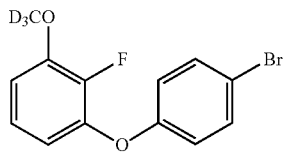

2-Fluoro-3-(methoxy-d3)phenol (636 mg, 4.4 mmol), 4-bromophenylboric acid (1.3 g, 6.6 mmol), anhydrous copper acetate (798 mg, 4.4 mmol) and dried powdered 4 A molecular sieve (3.0 g) were dispersed in DCM (10 mL). Triethylamine (887 mg, 8.8 mmol) was added dropwise into the mixture. The reacting solution was reacted for 16 h at room temperature and filtrated through diatomite to remove insoluble matter. After vacuum concentration, the residue was purified with column chromatography (petroleum ether:ethyl acetate=0-100%) to afford 1.0 g product, yield 77%.

$^1$H NMR (400 MHz, CDCl$_3$) δ 7.47-7.44 (m, 2H), 7.09-7.07 (m, 1H), 6.92-6.90 (m, 2H), 6.86-6.71 (m, 1H), 6.68-6.66 (m, 1H).

Step 4: 2-(4-(2-fluoro-3-(methoxy-d3)phenoxy)phenyl)-4,4,5,5-tetramethyl-1,3,2-dioxane

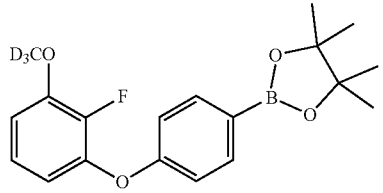

1-(4-Bromophenoxy)-2-fluoro-3-(methoxy-d3)benzene (1.0 g, 3.3 mmol), pinacol diboride (1.0 g, 4.0 mmol), PdCl$_2$(dppf) (219 mg, 0.3 mmol) and potassium acetate (655 mg, 6.7 mmol) were dispersed in 1,4-dioxane (15 mL). The mixture was exchanged with $N_2$ for 3 times and reacted for 16 h at 110° C. After cooled to room temperature, the reaction system was filtrated by kieselguhr to remove insoluble matter. The filtrate was concentrated under reduced pressure. The residue was purified with column chromatography (ethyl acetate:petroleum ether=0-100%) to afford 940 mg product, yield 78%.

$^1$H NMR (300 MHz, CDCl$_3$) δ 7.83 (d, J=8.4 Hz, 2H), 7.09-6.99 (m, 3H), 6.85-6.80 (m, 1H), 6.73-6.67 (m, 1H), 1.38 (s, 12H).

Step 5: (1R,3R)-3-(4-amino-3-iodo-1H-pyrazolo[3,4-d]pyrimidin-1-yl)cyclohexanol

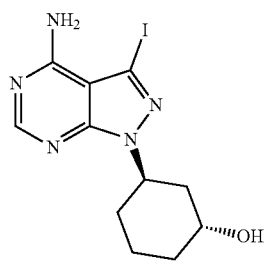 [SMILES: Nc1ncnc2c1c(I)nn2[C@@H]1CCC[C@@H](O)C1]

The (1R, 3R)-3-(4-amino-3-iodo-1H-pyrazolo[3,4-d]pyrimidin-1-yl)cyclohexyl acetate crude product was dissolved in the mixture of MeOH (40 mL) and THF (40 mL).

Hydrate LiOH (1.6 g, 39.2 mmol) was added, and the reacting solution was stirred at room temperature for 16 h and then vacuum filtrated to remove solid. The filtrate was concentrated under reduced pressure. The residue was purified with column chromatography (DCM:MeOH=0-100%) to afford 910 mg product.

MS ESI: m/z=360, [M+H]$^+$.

Step 6: (1R, 3S)-3-(4-amino-3-(4-(2-fluoro-3-(methoxy-d3)phenoxy)phenyl)-1H-pyrazolo[3,4-d]pyrimidin-1-yl)cyclohexanol

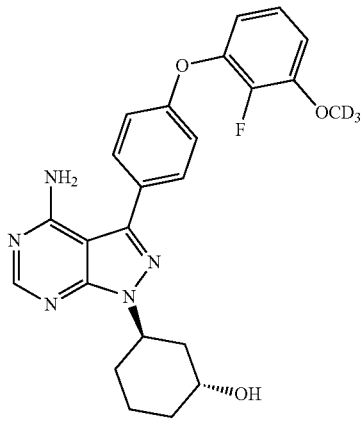

(1R,3R)-3-(4-amino-3-iodo-1H-pyrazolo[3,4-d]pyrimidin-1-yl)cyclohexanol (300 mg, 0.84 mmol), 2-(4-(2-fluoro-3-(methoxy-d3)phenoxy)phenyl)-4,4,5,5-tetramethyl-1,3,2-dioxane (347 mg, 1.0 mmol), tetratriphenylphosphine palladium (92 mg, 0.08 mmol) and potassium carbonate (231 mg, 1.68 mmol) were dispersed in the mixture of 1,4-dioxane (15 mL) and H₂O (1 mL). The mixture was exchanged with N₂ for 3 times and reacted for 16 h at 120° C. After cooled to room temperature, the reaction system was concentrated to remove organic solvent. The aqueous phase was extracted with DCM (20 mL×2). The combined organic phase was dried with anhydrous sodium sulfate. After filtration and concentration, the residue was purified with pre-HPLC to afford 110 mg product, yield 29%.

$^1$H NMR (400 MHz, CDCl₃) δ 8.36 (s, 1H), 7.64 (d, J=8.8 Hz, 2H), 7.13 (d, J=8.8 Hz, 2H), 7.09-7.03 (m, 1H), 6.85-6.80 (m, 1H), 6.74-6.70 (m, 1H), 5.58 (brs, 2H), 5.29-5.23 (m, 1H), 4.40 (s, 1H), 2.39-2.32 (m, 1H), 2.15-2.05 (m, 3H), 1.98-1.73 (m, 3H), 1.67-1.60 (m, 1H).

MS ESI: m/z=453, [M+H]⁺.

Example 32

(1S,3S)-3-(4-amino-3-(4-(2-fluoro-3-methoxyphenoxy)phenyl)-1H-pyrazolin[3,4-d]pyrimidin-1-yl)cyclohexanol

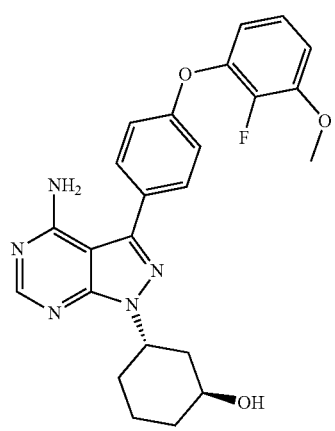 [SMILES: COc1cccc(Oc2ccc(-c3nn([C@H]4CCC[C@H](O)C4)c4ncnc(N)c34)cc2)c1F]

Step 1: trans-3-(3-(4-(2-fluoro-3-methoxyphenoxy)phenyl)-4-((triphenyl-l5-phosphinylidene)amino)-1H-pyrazolo[3,4-d]pyrimidin-1-yl)cyclohexyl 4-nitrobenzoate

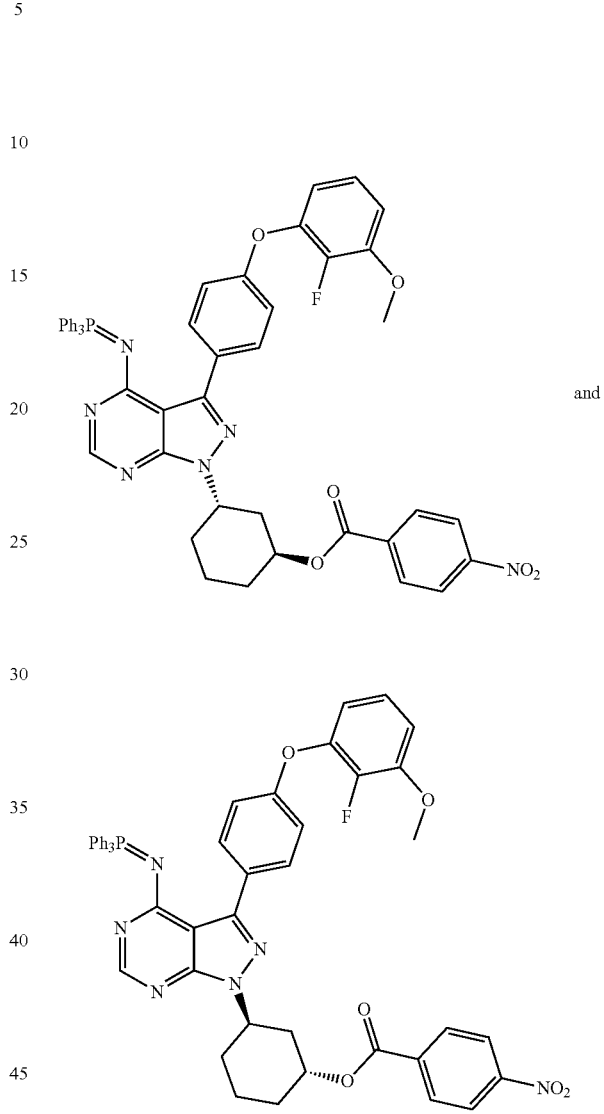

and

Cis-3-(4-amino-3-(4-(2-fluoro-3-methoxyphenoxy)phenyl)-1H-pyrazolo[3,4-d]pyrimidin-1-yl)cyclohex-1-ol (3.3 g, 9.55 mmol) was dissolved in THF (60 mL), and p-nitrobenzoic acid (1.60 g, 9.55 mmol) and PPh₃ (4.81 g, 18.38 mmol) were added successively. The mixture was cooled to 0° C., and diisopropyl azodicarboxylate (4.45 g, 22.05 mmol) was added dropwise under N₂. After addition, the reacting solution was allowed to warm to room temperature and reacted for 2 h. The reaction system was quenched by 100 mL brine and extracted with DCM (50 mL×3). The combined organic phase was dried with anhydrous sodium sulfate. After filtration and concentration, the residue was purified with column chromatography (petroleum ether: ethyl acetate=0-100%) to afford 6.8 g crude product.

MS ESI: m/z=859, [M+H]⁺.

Step 2: trans-3-(4-amino-3-(4-(2-fluoro-3-methoxyphenoxy)phenyl)-1H-pyrazolo[3,4-d]pyrimidin-1-yl)cyclohexyl 4-nitrobenzoate

Step 3: trans-3-(4-amino-3-(4-(2-fluoro-3-methoxyphenoxy)phenyl)-1H-pyrazolin[3,4-d]pyrimidin-1-yl)cyclohexanol

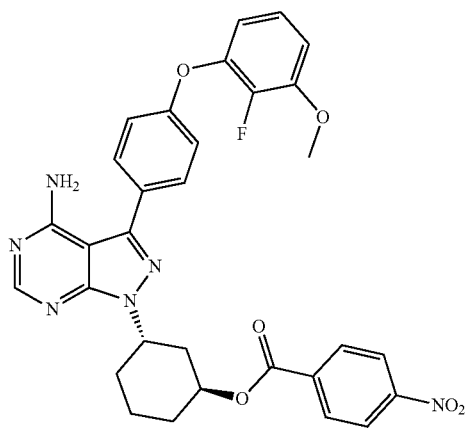 and 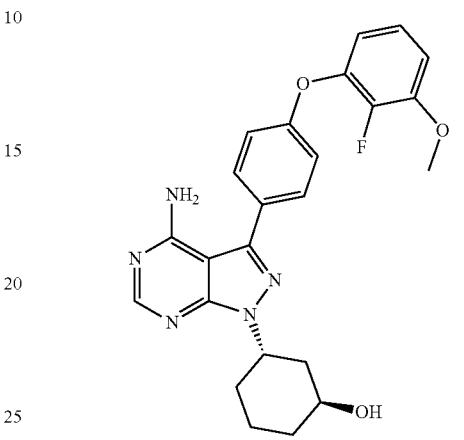 and

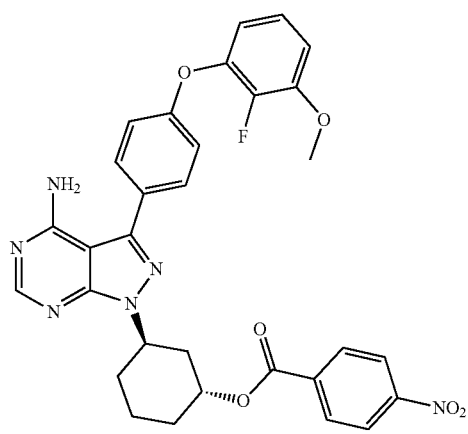

The crude product of trans-3-(3-(4-(2-fluoro-3-methoxyphenoxy)phenyl)-4-((triphenyl-15-phosphinylidene)amino)-1H-pyrazolo[3,4-d]pyrimidin-1-yl)cyclohexyl 4-nitrobenzoate (5.6 g) was dissolved in acetic acid (20 mL). The mixture was diluted with H₂O. The resulting solution was warmed to 130° C. to reflux for 12 h. The reacting solution was vacuum concentrated to remove most solvent, added with H₂O, and extracted with DCM (50 mL×3). The combined organic phase was dried with anhydrous sodium sulfate. After concentration, the residue was purified with toluene (100 mL×3) to remove residual acetic acid to afford 6.8 g crude product.

MS ESI: m/z=599, [M+H]⁺.

6.8 g Crude product of trans-3-(4-amino-3-(4-(2-fluoro-3-methoxyphenoxy)phenyl)-1H-pyrazolo[3,4-d]pyrimidin-1-yl)cyclohexyl 4-nitrobenzoate was dissolved in the mixture of THF (40 mL) and H₂O (10 mL). LiOH monohydrate (1.0 g, 23.8 mmol) was added into the resulting solution. After reacted at room temperature for 2 h, the solution was mixed with brine (100 mL) and extracted with DCM (100 mL×3). The combined organic phase was dried with anhydrous sodium sulfate. After filtration and concentration, the residue was purified with column chromatography (DCM:MeOH=0-100%) to afford 1.6 g product, three steps yield 48.5%.

MS ESI: m/z=450, [M+H]⁺.

Step 4: (1S, 3S)-3-(4-amino-3-(4-(2-fluoro-3-methoxyphenoxy)phenyl)-1H-pyrazolin[3,4-d]pyrimidin-1-yl)cyclohexanol

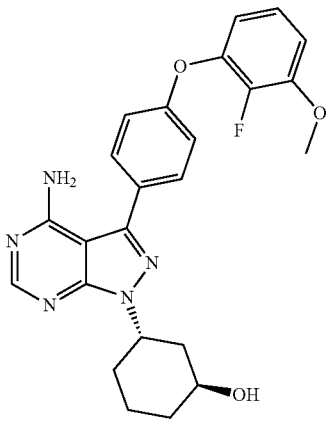 [SMILES: COc1cccc(Oc2ccc(-c3nn([C@H]4CCC[C@H](O)C4)c4ncnc(N)c34)cc2)c1F]

Trans-3-(4-amino-3-(4-(2-fluoro-3-methoxyphenoxy)phenyl)-1H-pyrazolin[3,4-d]pyrimidin-1-yl)cyclohexanol (1.6 g, 3.56 mmol) was purified with chiral SFC to afford 640 mg product, yield 80%.

$^1$H NMR (400 MHz, CDCl$_3$) δ 8.37 (s, 1H), 7.65-7.62 (m, 2H), 7.14-7.04 (m, 3H), 6.85-6.81 (m, 1H), 6.75-6.71 (m, 1H), 5.41 (brs, 2H), 5.25 (m, 1H), 4.40 (m, 1H), 3.94 (s, 3H), 2.36-2.33 (m, 1H), 2.14-2.01 (m, 4H), 1.80-1.77 (m, 2H), 1.66 (m, 1H).

MS ESI: m/z=450, [M+H]$^+$.

Example 33

(1R,3R)-3-(4-(4-amino-1-(3-hydroxycyclohexyl)-1H-pyrazolo[3,4-d]pyrimidin-3-yl)phenoxy)-2-fluorophenol

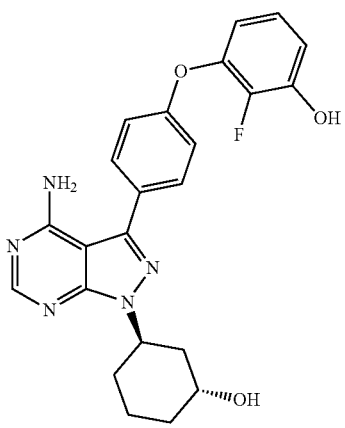 [SMILES: Nc1ncnc2c1c(-c1ccc(Oc3cccc(O)c3F)cc1)nn2[C@@H]1CCC[C@@H](O)C1]

(1R, 3R)-3-(4-amino-3-(4-(2-fluoro-3-methoxyphenoxy)phenyl)-1H-pyrazolo[3,4-d]pyrimidin-1-yl)cyclohexanol (450 mg, 1.0 mmol) was dissolved in DCM (10 mL), and cooled to 0° C. 1N Boron tribromide in DCM (1.5 mL, 1.5 mmol) was added dropwise. The mixture was naturally warmed to room temperature and reacted for 1 h. The reaction system was diluted with DCM (50 mL) and then washed with saturated sodium bicarbonate solution (100 mL×3). The organic phase was dried with anhydrous sodium sulfate. After filtration and concentration, the residue was purified with pre-HPLC to afford 240 mg product, yield 55%.

$^1$H NMR (400 MHz, DMSO-d6): 11.12 (brs, 1H), 8.22 (s, 1H), 7.64 (d, J=8.4 Hz, 2H), 7.11 (d, J=8.4 Hz, 2H), 7.03-6.99 (m, 1H), 6.86-6.81 (m, 1H), 6.67-6.63 (m, 1H), 7.21-6.33 (m, 2H), 5.12-5.06 (m, 1H), 4.64 (brs, 1H), 4.14 (brs, 1H), 2.18-2.07 (m, 1H), 1.92-1.83 (m, 4H), 1.69-1.59 (m, 2H), 1.51-1.45 (m, 1H).

MS ESI: m/z=436, [M+H]+

Biochemical Evaluation

The BTK/BTK (C481S) inhibitory activity of compound of formula A was determined in Reaction Biology Corporation, One Great Valley Parkway, Malvern, PA, USA. Full-length human BTK/BTK (C481S) enzyme and 20 μM peptide substrate [KVEKIGEGTYGVVYK] were used. The concentration of tested ATP was 10 μM. Starsporin was used as standard, of which IC$_{50}$ was 3.94 nM.

Table 1 represented BTK/BTK (C481S) inhibitory activity of compounds according to examples.

TABLE 1

| Compound | Concentration of inhibitor was 5 nM, concentration of ATP was 10 uM | |
|---|---|---|
| | BTK inhibitory rate(%) | BTK(C481S) inhibitory rate(%) |
| Example 1 | 60 | — |
| Example 2 | 50 | — |
| Example 5 | 62 | 53 |
| Example 6 | 70 | 63 |
| Example 8A | 82 | 66 |
| Example 8B | — | — |
| Example 9A | 57 | 77 |
| Example 9B | 46 | 63 |
| Example 10 | 63 | 72 |
| Example 15 | 55 | — |

Wherein, the IC$_{50}$ value of some examples on BTK/BTK (C481S) enzyme were as shown below in table 2.

TABLE 2

| Compound | IC$_{50}$(nM) | |
|---|---|---|
| | BTK | BTK(C481S) |
| Example 1 | 8.1$^b$ | 3.4$^b$ |
| Example 8A | 2.5$^c$ | 0.7$^c$ |
| Example 15 | 3.8$^c$ | 1.7$^c$ |
| Example 16 | 18.8$^a$ | — |
| Example 17 | 24.1$^a$ | — |
| Example 18 | 49.1$^a$ | — |
| Example 19 | 24.9$^a$ | — |
| Example 20 | 5$^b$ | 0.9$^b$ |
| Example 21 | 16.0$^a$ | — |
| Example 22 | 3.5$^b$ | 1$^b$ |
| Example 23 | 14.3$^a$ | — |
| Example 24 | — | — |
| Example 25 | 26.9$^a$ | — |
| Example 26 | — | — |
| Example 27 | — | — |
| Example 28 | 1.7$^d$ | 0.6$^d$ |
| Example 29(reference compound) | 64.1$^a$ | — |
| Example 30 Peak1-1 | 3.8$^d$ | 3.7$^d$ |
| Example 30 Peak1-2 | 8.5$^d$ | 6.7$^d$ |
| Example 30 Peak2-1 | 1.8$^d$ | 1.1$^d$ |
| Example 30 Peak2-2 | 5.0$^d$ | 2.8$^d$ |

TABLE 2-continued

| Compound | IC$_{50}$(nM) | |
| --- | --- | --- |
| | BTK | BTK(C481S) |
| Example 31 | — | — |
| Example 32 | 2.6$^d$ | 0.9$^d$ |
| Example 33 | 19.2$^a$ | — |

In examples labeled with (a), ATP concentration was 30 μM; in examples labeled with (b), ATP concentration was 100 μM; In examples labeled with (c), ATP concentration was 10 μM; In examples labeled with (d), ATP concentration was 50 μM; "-" meant not tested.

The results showed that compared with the control compound 29 without hydroxyl substituent on the ring, the compounds of the present application showed better inhibitory activity to BTK (wild type and mutant type).

CellTiter-Glo kit was used to test the TMD8 inhibitory activity of compounds of examples on Human diffuse large B lymphoma cells cultured in vitro. IC$_{50}$ values were shown below.

Table 3 has shown the inhibitory activity of the compounds of the examples on TMD8 cells

TABLE 3

| Compound | IC$_{50}$ (nM) |
| --- | --- |
| Example 1 | 20 |
| Example 3A | 208 |
| Example 3B | 200 |
| Example 5 | 29 |
| Example 6 | 17 |
| Example 7 | 504 |
| Example 8A | 90 |
| Example 9A | 72 |
| Example 9B | 37 |
| Example 10 | 145 |
| Example 16 | 41 |
| Example 17 | 33 |
| Example 18 | 183 |
| Example 19 | 0.5 |
| Example 20 | 8.6 |
| Example 22 | 8 |

In Vivo Efficacy Assessment

In the subcutaneous transplantation tumor model of human diffuse large B lymphoma TMD8 cells in NOD/SCID mice, the inhibitory effect of example 1 on tumor growth was tested. Tumor growth and animal body weight were presented in FIG. 1 and FIG. 2 as followed. Example 1 was administered orally once a day at 30 mg/kg, or twice a day at 10→5 mg/kg, which had obvious inhibitory effect on the growth of subcutaneous transplanted TMD8 tumor. The tumor growth inhibition rate (TGI) after 22 days of administration was 49.6% and 52.7% respectively. Example 1 had no significant effect on animal body weight at 30 mg/kg dose when administered orally once a day. Animal body weight decreased slightly at 10 mg/kg dose administered orally twice a day for 8 successive days. Therefore, the dose was adjusted to 5 mg/kg and continued to administrate for 14 days.

FIG. 1 showed the volumes of subcutaneous xenograft TMD8 tumor (mean SD) of the solvent control group and each treatment group during administration. The results showed that 22 days after the initial administration, the compound of the invention showed significant therapeutic effect, and the therapeutic effect was equivalent to that of the positive drug ibrutinib.

Figure 2:
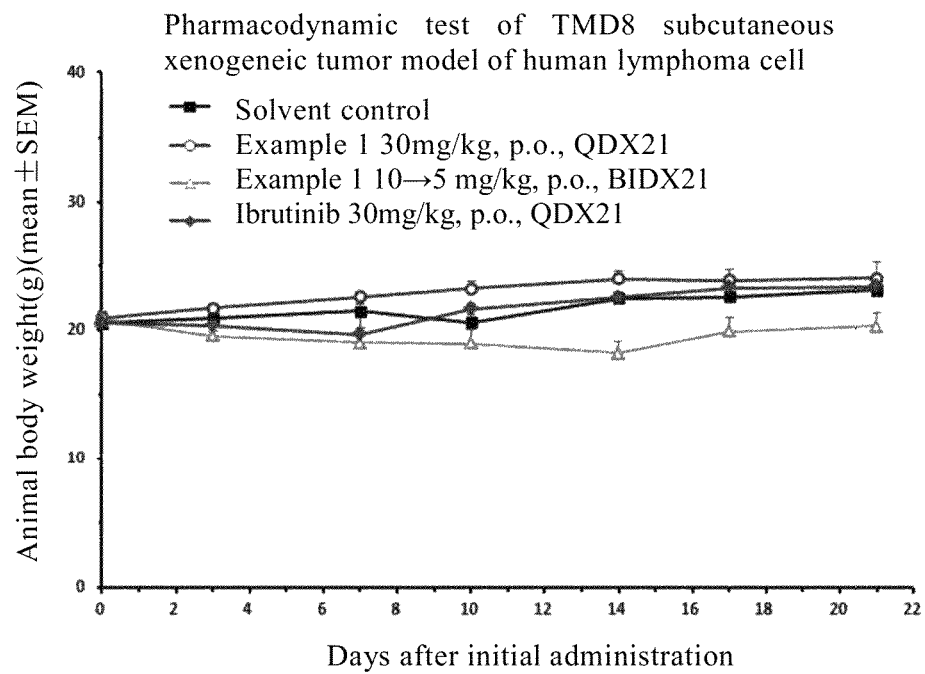
FIG. 2: the body weight (mean SD) of the solvent control group and the animals in each treatment group during administration.

FIG. 2 showed the changes in the body weight (mean SD) of the solvent control group and the animals in each treatment group during administration. The results showed that the compound of example 1 of the invention showed significant anti-tumor effect without showing obvious influence on the body weight of animals.

According to the experimental results, example 1 of the invention showed significant anti-tumor effect, which significantly inhibited the growth of tumor without showing obvious influence on the body weight of animals.

What we claim is:
1. A compound according to the Formula B:

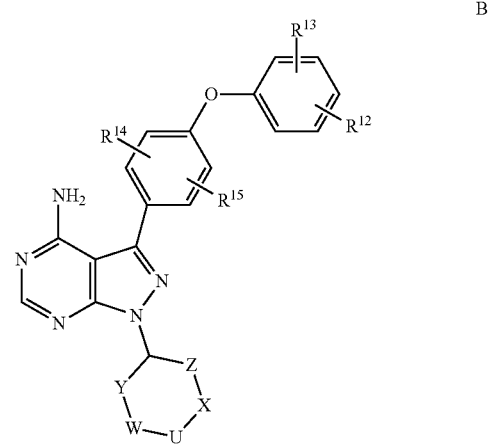

or pharmaceutically acceptable salts thereof,
wherein,
R$^{12}$ and R$^{13}$ are each independently selected from the group consisting of halogen and unsubstituted or halogenated C$_1$-C$_6$ alkoxy;
R$^{14}$ and R$^{15}$ are each independently selected from the group consisting of H, halogen, and unsubstituted or halogenated C$_1$-C$_6$ alkoxy;
Z is (CR$^2$R$^3$)$_n$, in which n is 1 or 2;
Y is (CR$^4$R$^5$)$_m$, in which m is 1 or 2;
U is (CR$^6$R$^7$)$_r$, in which r is 1;
R$^2$, R$^3$, R$^4$, R$^5$, R$^6$ and R$^7$ are selected independently from the group consisting of H, OH, halogen, substituted or unsubstituted C$_1$-C$_6$ alkyl;
wherein in the above groups in R$^2$, R$^3$, R$^4$, R$^5$, R$^6$ and R$^7$, "substituted" refers to being substituted by one or more substituents selected from the group consisting of halogen, C$_1$-C$_6$ alkyl, C$_1$-C$_6$ alkoxy, halogenated C$_1$-C$_6$ alkoxy, C$_3$-C$_8$ cycloalkyl, halogenated C$_3$-C$_8$ cycloalkyl, —CN, and hydroxy;
W is selected from the group consisting of O and a bond;
X is —C(R$^8$R$^9$)—;
ring

is a 5 or 6 membered ring;
R$^8$ is selected from the group consisting of H, substituted or unsubstituted C$_1$-C$_6$ alkyl, and substituted or unsubstituted C$_3$-C$_{10}$ cycloalkyl; wherein the "substituted" in R[8] refers to being substituted by one or more substituents selected from the group consisting of halogen, $C_1$-$C_6$ alkyl, and $C_3$-$C_8$ cycloalkyl;

R[9] is selected from the group consisting of OH and —[CH$_2$]$_k$—OH; and k is 1 or 2.

2. The compound according to claim 1, wherein, the compound has a structure according to following formula B:

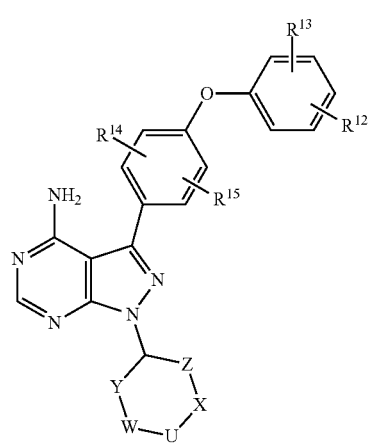

B wherein,

R[14] and R[15] are independently H.

3. The compound according to claim 1, wherein, the compound has a structure according to formula D or E:

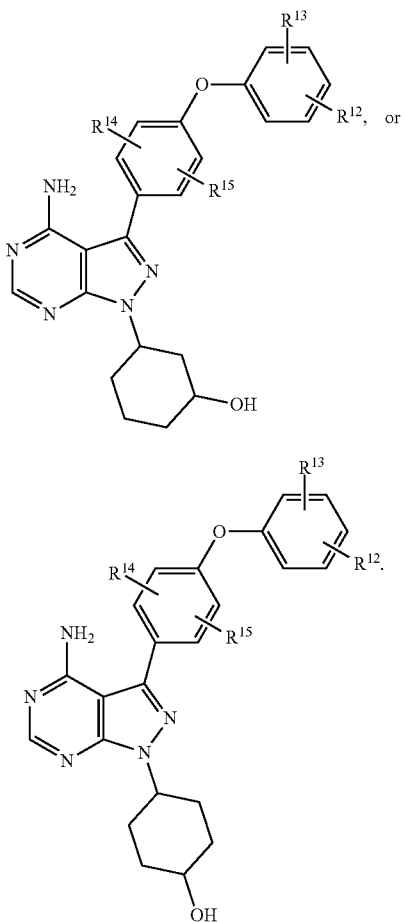

D

E

4. The compound according to claim 1, wherein, the compound is selected from the group consisting of

| 18 | (1R,3R)-3-(4-amino-3-(4-(2,6-difluorophenoxy)phenyl)-1H-pyrazolo[3,4-d]pyrimidin-1-yl)cyclohex-1-ol |

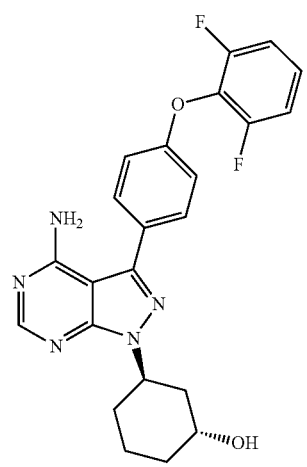 [SMILES: Nc1ncnc2c1c(-c1ccc(Oc3c(F)cccc3F)cc1)nn2[C@@H]1CCC[C@@H](O)C1]

| | | |
|---|---|---|
| 19 | (1R,3R)-3-(4-amino-3-(4-(2-fluoro-3-methoxyphenoxy)phenyl)-1H-pyrazolo[3,4-d]pyrimidin-1-yl)cyclohex-1-ol | 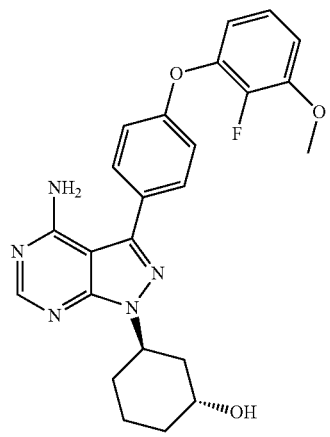 [SMILES: COc1cccc(Oc2ccc(-c3nn([C@@H]4CCC[C@@H](O)C4)c4ncnc(N)c34)cc2)c1F] |
| 20 | (1s,4s)-4-(4-amino-3-(4-(2-fluoro-3-methoxyphenoxy)phenyl)-1H-pyrazolo[3,4-d]pyrimidin-1-yl)cyclohex-1-ol | 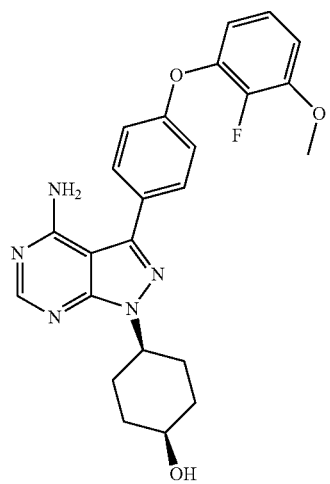 [SMILES: COc1cccc(Oc2ccc(-c3nn([C@H]4CC[C@@H](O)CC4)c4ncnc(N)c34)cc2)c1F] |
| 21 | (1r,4r)-4-(4-amino-3-(4-(2-fluoro-3-methoxyphenoxy)phenyl)-1H-pyrazolo[3,4-d]pyrimidin-1-yl)cyclohex-1-ol | 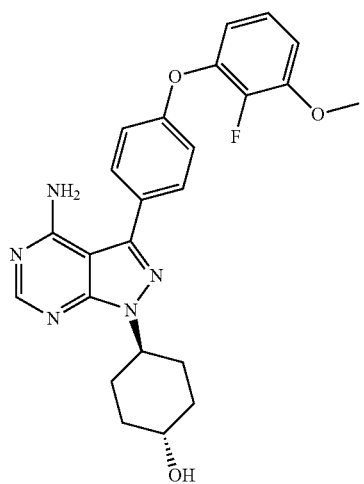 [SMILES: COc1cccc(Oc2ccc(-c3nn([C@H]4CC[C@H](O)CC4)c4ncnc(N)c34)cc2)c1F] |

| | | |
|---|---|---|
| 22 | Cis-3-(4-amino-3-(4-(2-fluoro-3-methoxyphenoxy)phenyl)-1H-pyrazolo[3,4-d]pyrimidin-1-yl)cyclopentane-1-ol | 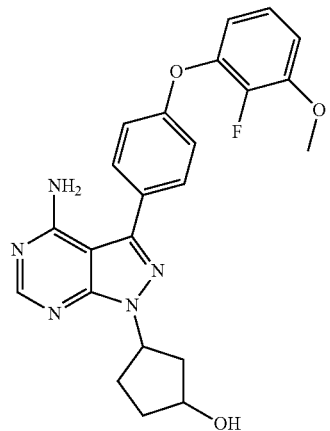 [SMILES: COc1cccc(Oc2ccc(-c3nn(C4CCC(O)C4)c4ncnc(N)c34)cc2)c1F] |
| 23 | Trans-3-(4-amino-3-(4-(2-fluoro-3-methoxyphenoxy)phenyl)-1H-pyrazolo[3,4-d]pyrimidin-1-yl)cyclopentane-1-ol | 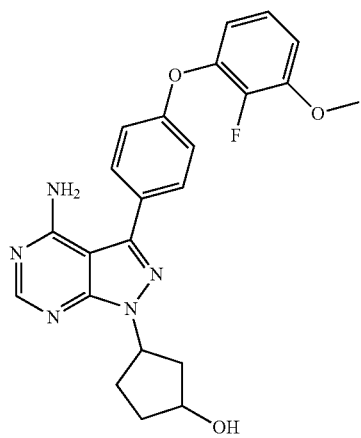 [SMILES: COc1cccc(Oc2ccc(-c3nn(C4CCC(O)C4)c4ncnc(N)c34)cc2)c1F] |
| 26 | Cis-3-(4-amino-3-(4-(2-fluoro-3-methoxyphenoxy)phenyl)-1H-pyrazolo[3,4-d]pyrimidin-1-yl)cyclohex-1-ol | 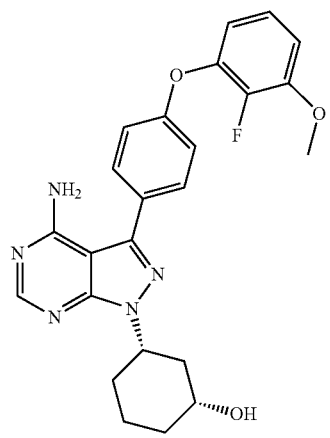 [SMILES: COc1cccc(Oc2ccc(-c3nn([C@H]4CCC[C@@H](O)C4)c4ncnc(N)c34)cc2)c1F] |

| 27 | 3-(4-amino-3-(4-(2-fluoro-3-methoxyphenoxy)phenyl)-1H-pyrazolo[3,4-d]pyrimidin-1-yl)cyclohexane-1,2-diol | 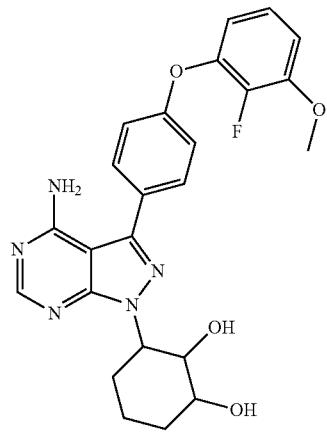 [SMILES: COc1cccc(Oc2ccc(-c3nn(C4CCCC(O)C4O)c4ncnc(N)c34)cc2)c1F] |
| 28 | 4-(4-amino-3-(4-(2-fluoro-3-methoxyphenoxy)phenyl)-1H-pyrazolo[3,4-d]pyrimidin-1-yl)cyclohexane-1,2-diol | 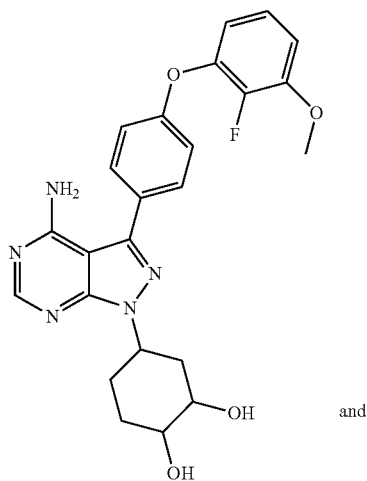 [SMILES: COc1cccc(Oc2ccc(-c3nn(C4CCC(O)C(O)C4)c4ncnc(N)c34)cc2)c1F] and |
| 32 | (1S,3S)-3-(4-amino-3-(4-(2-fluoro-3-methoxyphenoxy)phenyl)-1H-pyrazolo[3,4-d]pyrimidin-1-yl)cyclohexanol | 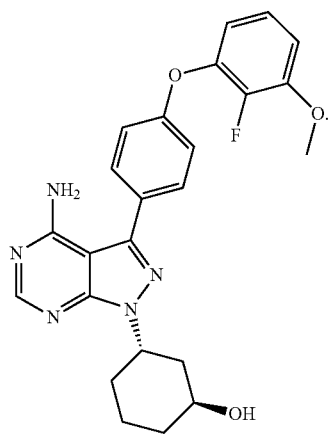 [SMILES: COc1cccc(Oc2ccc(-c3nn([C@H]4CCC[C@H](O)C4)c4ncnc(N)c34)cc2)c1F] |

5. A pharmaceutical composition comprising (1) the compound of claim 1, or stereoisomers or tautomers thereof, or pharmaceutically acceptable salts, hydrates or solvates thereof; and (2) pharmaceutically acceptable carriers.

6. A method for treating a disease or disorder, which relates to a BTK abnormal activity and a BTK mutant abnormal activity; the method comprising administering to a subject in need thereof an effective amount of the compound according to claim 1, or stereoisomers or tautomers thereof, or pharmaceutically acceptable salts, hydrates or solvates thereof; or a pharmaceutical composition comprising such and a pharmaceutically acceptable carrier; wherein the disease or disorder is selected from the group consisting of bladder cancer, brain tumor, breast cancer, uterine cancer, colorectal cancer, esophageal cancer, liver cancer, follicular lymphoma, melanoma, malignant hematologic disease, myeloma, ovarian cancer, non-small cell lung cancer, prostate cancer, small cell lung cancer, and B-cell derived lymphoid malignancy, B cell proliferative disorder: diffuse B cell lymphoma, follicular lymphoma, chronic lymphocytic leukemia, B-cell prolymphocyte leukemia, lymphoplasmacytic lymphoma/Waldenstrom's macroglobulinemia, splenic marginal zone lymphoma, plasmacytic myeloma, plasmacytoma, extranodal marginal zone B-cell lymphoma, intranodal marginal zone B-cell lymphoma, mantle cell lymphoma Mediastinal (thymic) large B-cell lymphoma, intravascular large B-cell lymphoma, primary exudative lymphoma, and Burkitt's lymphoma/leukemia and lymphomatoid granulomatosis.

7. The method according to claim 6, wherein the BTK mutant is C481S.

8. The compound according to claim 1, wherein, the

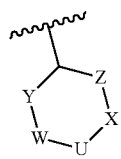

is selected from the group consisting of

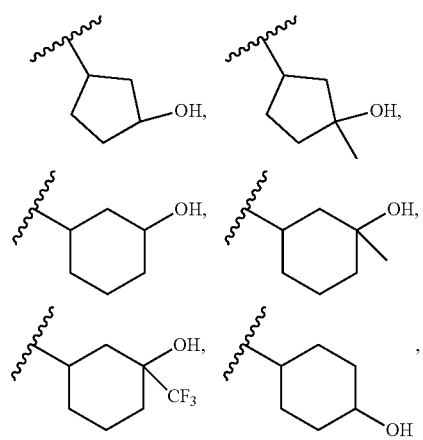

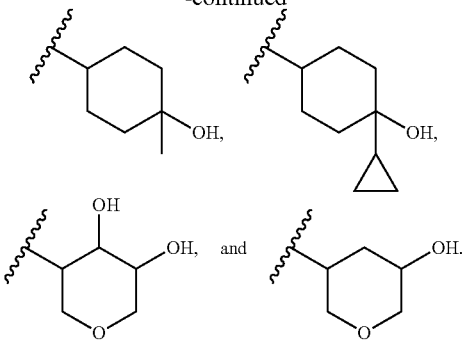

9. The compound according to claim 1, wherein, the

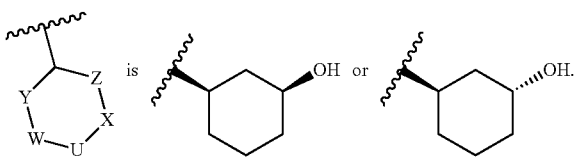

10. The compound according to claim 1, wherein, the

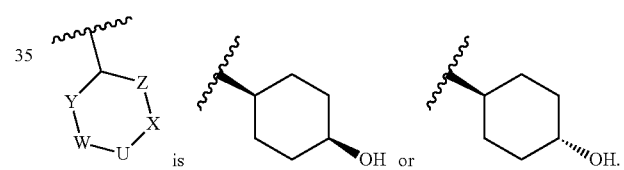

11. A compound selected from the group consisting of 15  (1R, 3R)-3-(4-amino-3-(4-(3-fluorophenoxy) phenyl)-1H-pyrazolo[3,4-d]pyrimidin-1-yl) cyclohex-1-ol

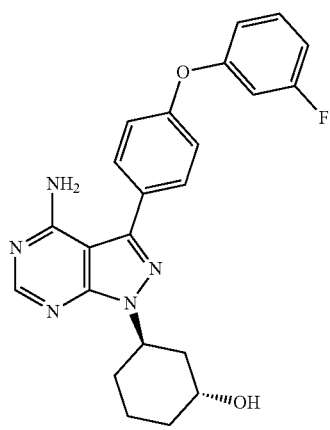 [SMILES: Nc1ncnc2c1c(-c1ccc(Oc3cccc(F)c3)cc1)nn2[C@@H]1CCC[C@@H](O)C1]

-continued
| | |
|---|---|
| 16 | (1R, 3R)-3-(4-amino-3-(2-fluoro-4-phenoxyphenyl)-1H-pyrazolo[3,4-d]pyrimidin-1-yl) cyclohex-1-ol |
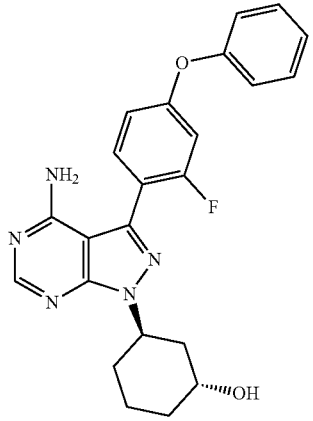
| | |
|---|---|
| 17 | (1R, 3R)-3-(4-amino-3-(4-(3-fluorophenoxy) phenyl)-1H-pyrazolo[3,4-d]pyrimidin-1-yl) cyclohex-1-ol |
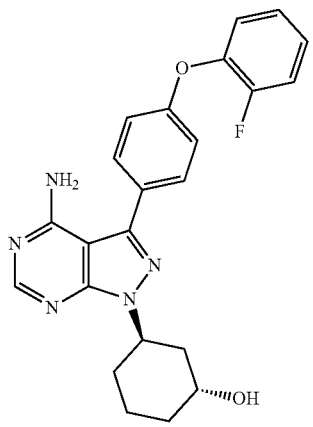 [SMILES: Nc1ncnc2c1c(-c1ccc(Oc3ccccc3F)cc1)nn2[C@@H]1CCC[C@@H](O)C1]
| | |
|---|---|
| 25 | 3-(4-amino-3-(4-(3-fluorophenoxy) phenyl)-1H-pyrazolo[3,4-d]pyrimidin-1-yl)cyclopentane-1-ol |
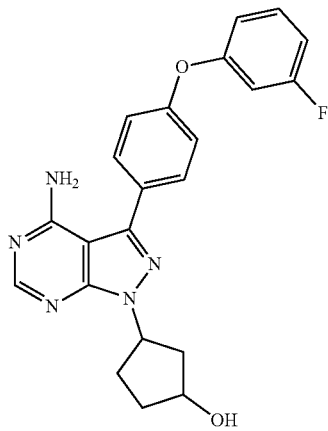 [SMILES: Nc1ncnc2c1c(-c1ccc(Oc3cccc(F)c3)cc1)nn2C1CCC(O)C1]

-continued
| | | |
|---|---|---|
| 30 | (5-(4-amino-3-(4-(2-fluoro-3-methoxyphenoxy)phenyl)-1H-pyrazolo[3,4-d]pyrimidin-1-yl)tetrahydro-2h-pyran-2-yl)methanol | 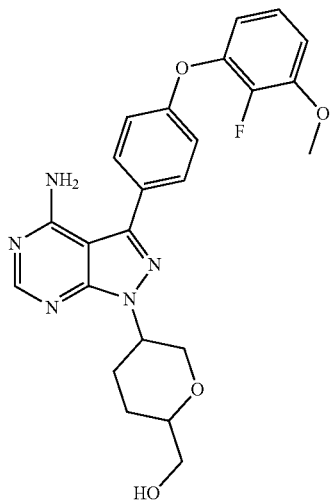 [SMILES: COc1cccc(Oc2ccc(-c3nn(C4CCC(CO)OC4)c4ncnc(N)c34)cc2)c1F] |
| 31 | (1R,3R)-3-(4-amino-3-(4-(2-fluoro-3-(methoxy-d3)phenoxy)phenyl)-1H-pyrazolo[3,4-d]pyrimidin-1-yl)cyclohexanol | 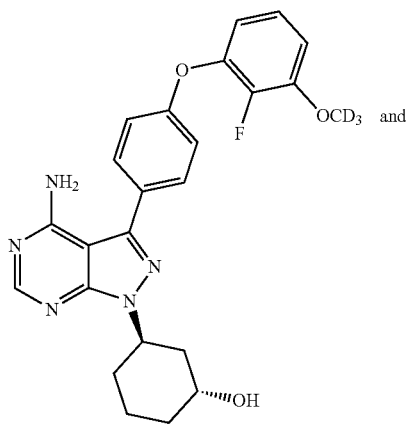 and |
| 33 | 3-(4-(4-amino-1-((1R,3R)-3-hydroxycyclohexyl)-1H-pyrazolo[3,4-d]pyrimidin-3-yl)phenoxy)-2-fluorophenol | 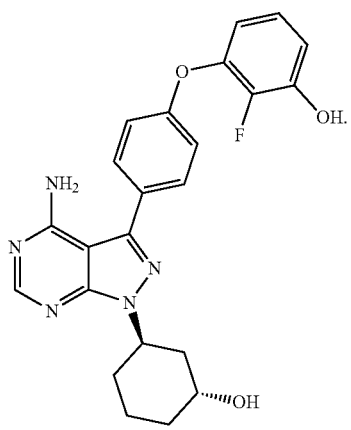 [SMILES: Nc1ncnc2c1c(-c1ccc(Oc3cccc(O)c3F)cc1)nn2[C@@H]1CCC[C@@H](O)C1] |
* * * * *